United States Patent
Kurihara et al.

(10) Patent No.: US 12,043,624 B2
(45) Date of Patent: Jul. 23, 2024

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Miki Kurihara, Kanagawa (JP); Tomoka Hara, Kanagawa (JP); Hideko Yoshizumi, Kanagawa (JP); Satomi Watabe, Kanagawa (JP); Hiromitsu Kido, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 298 days.

(21) Appl. No.: 16/621,070

(22) PCT Filed: Jun. 12, 2018

(86) PCT No.: PCT/IB2018/054222
§ 371 (c)(1),
(2) Date: Dec. 10, 2019

(87) PCT Pub. No.: WO2018/234926
PCT Pub. Date: Dec. 27, 2018

(65) Prior Publication Data
US 2020/0199135 A1 Jun. 25, 2020

(30) Foreign Application Priority Data
Jun. 22, 2017 (JP) .................................. 2017-122567

(51) Int. Cl.
C07D 491/048 (2006.01)
H10K 50/11 (2023.01)
H10K 85/60 (2023.01)
H10K 101/10 (2023.01)

(52) U.S. Cl.
CPC ....... C07D 491/048 (2013.01); H10K 85/622 (2023.02); H10K 85/6576 (2023.02); H10K 50/11 (2023.02); H10K 2101/10 (2023.02)

(58) Field of Classification Search
CPC .............. C07D 491/048; C07D 495/04; H01L 51/0052; H01L 51/0054–0058; H01L 51/0071–0074; H10K 85/615; H10K 85/622; H10K 85/623; H10K 85/624; H10K 85/625; H10K 85/626; H10K 85/657; H10K 85/6572; H10K 85/6574; H10K 85/6576

See application file for complete search history.

(56) References Cited

U.S. PATENT DOCUMENTS

| | | |
|---|---|---|
| 3,634,427 A | 1/1972 | Schweizer et al. |
| 7,326,712 B2 | 2/2008 | Hurley et al. |
| 8,007,927 B2 | 8/2011 | Lin et al. |
| 8,221,905 B2 | 7/2012 | Lin et al. |
| 8,367,850 B2 | 2/2013 | Ma et al. |
| 8,415,031 B2 | 4/2013 | Xia et al. |
| 8,586,204 B2 | 11/2013 | Xia et al. |
| 8,652,652 B2 | 2/2014 | Brooks et al. |
| 8,741,446 B2 | 6/2014 | Lin et al. |
| 8,866,377 B2 | 10/2014 | Adamovich et al. |
| 8,921,549 B2 | 12/2014 | Inoue et al. |
| 8,952,363 B2 | 2/2015 | Lin et al. |
| 8,999,988 B2 | 4/2015 | Hurley et al. |
| 9,067,947 B2 | 6/2015 | Lin et al. |
| 9,276,228 B2 | 3/2016 | Seo et al. |
| 9,905,782 B2 | 2/2018 | Inoue et al. |
| 10,193,086 B2 | 1/2019 | Inoue et al. |
| 10,538,510 B2 | 1/2020 | Lee et al. |
| 10,586,931 B2 | 3/2020 | Kanamoto et al. |
| 10,693,094 B2 | 6/2020 | Seo et al. |
| 10,700,291 B2 | 6/2020 | Inoue et al. |

(Continued)

FOREIGN PATENT DOCUMENTS

| | | |
|---|---|---|
| CN | 105103327 A | 11/2015 |
| CN | 105849112 A | 8/2016 |

(Continued)

OTHER PUBLICATIONS

Katakura, Rie et al., machine translation of JP-2011084531-A (2011) pp. 1-80. (Year: 2011).*
Morinaka et al., machine translation of WO 2015/037675 A1 (2015) pp. 1-52. (Year: 2015).*
European Search Report (Application No. 18820614.8) Dated Nov. 23, 2020.
International Search Report re Application No. PCT/IB2018/054222, dated Sep. 18, 2018.

(Continued)

Primary Examiner — Dylan C Kershner
(74) Attorney, Agent, or Firm — Husch Blackwell LLP

(57) ABSTRACT

A novel organic compound is provided. That is, a novel organic compound that is effective in improving the element characteristics and reliability is provided. The organic compound has a benzofuropyrimidine skeleton or a benzothienopyrimidine skeleton and is represented by General Formula (G1). Note that in General Formula (G1), Q represents oxygen or sulfur; α represents a substituted or unsubstituted arylene group having 6 to 13 carbon atoms; n represents an integer of 0 to 4; A1 represents a group including an aryl group or a heteroaryl group and having 6 to 100 carbon atoms; R1 to R4 independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and A2 represents a condensed ring.

15 Claims, 35 Drawing Sheets

(56) References Cited

U.S. PATENT DOCUMENTS

| | | | |
|---|---|---|---|
| 10,734,588 B2 | 8/2020 | Park et al. | |
| 11,088,332 B2* | 8/2021 | Kanamoto | H10K 85/6572 |
| 11,530,224 B2 | 12/2022 | Parham et al. | |
| 2007/0159083 A1 | 7/2007 | Matsuura et al. | |
| 2008/0269239 A1 | 10/2008 | Harris et al. | |
| 2008/0314965 A1 | 12/2008 | Roberts et al. | |
| 2009/0163545 A1 | 6/2009 | Goldfarb | |
| 2010/0187984 A1 | 7/2010 | Lin et al. | |
| 2012/0061654 A1 | 3/2012 | Rayabarapu et al. | |
| 2013/0060037 A1 | 3/2013 | Lin et al. | |
| 2014/0284642 A1* | 9/2014 | Yamazaki | H01L 51/5275 257/98 |
| 2014/0291645 A1 | 10/2014 | Inoue et al. | |
| 2015/0021555 A1 | 1/2015 | Kwong et al. | |
| 2015/0021556 A1 | 1/2015 | Xia et al. | |
| 2015/0207082 A1 | 7/2015 | Dyatkin et al. | |
| 2015/0243893 A1 | 8/2015 | Joseph et al. | |
| 2015/0318495 A1 | 11/2015 | Kawakami et al. | |
| 2015/0325799 A1 | 11/2015 | Hwang et al. | |
| 2016/0013421 A1 | 1/2016 | Inoue et al. | |
| 2016/0072078 A1 | 3/2016 | Lee et al. | |
| 2016/0240791 A1 | 8/2016 | Lee et al. | |
| 2016/0308143 A1* | 10/2016 | Kim | C07D 519/00 |
| 2016/0322585 A1 | 11/2016 | Kim et al. | |
| 2016/0329503 A1 | 11/2016 | Yeager et al. | |
| 2016/0351826 A1 | 12/2016 | Kim et al. | |
| 2016/0351829 A1 | 12/2016 | Hosoumi et al. | |
| 2016/0351833 A1 | 12/2016 | Hosoumi et al. | |
| 2017/0092889 A1 | 3/2017 | Seo et al. | |
| 2017/0186971 A1* | 6/2017 | Kanamoto | C09K 11/06 |
| 2017/0200903 A1* | 7/2017 | Park | H01L 51/0074 |
| 2018/0155325 A1 | 6/2018 | Lee et al. | |
| 2019/0135814 A1 | 5/2019 | Parham et al. | |
| 2020/0024282 A1* | 1/2020 | Parham | H10K 85/6576 |
| 2020/0028091 A1 | 1/2020 | Parham et al. | |
| 2020/0350508 A1 | 11/2020 | Seo et al. | |
| 2021/0013428 A1 | 1/2021 | Inoue et al. | |
| 2021/0111362 A1 | 4/2021 | Seo et al. | |
| 2021/0363151 A1* | 11/2021 | Seo | H10K 85/657 |
| 2023/0117837 A1 | 4/2023 | Parham et al. | |

FOREIGN PATENT DOCUMENTS

| | | | | |
|---|---|---|---|---|
| CN | 106206963 A | 12/2016 | | |
| EP | 2 910 555 A1 | 8/2015 | | |
| EP | 3 056 498 A1 | 8/2016 | | |
| JP | 06-220059 A | 8/1994 | | |
| JP | 2004-241374 A | 8/2004 | | |
| JP | 2006-024830 A | 1/2006 | | |
| JP | 2007-015933 A | 1/2007 | | |
| JP | 2007-510627 | 4/2007 | | |
| JP | 2010-182699 A | 8/2010 | | |
| JP | 2011-509247 | 3/2011 | | |
| JP | 2011084531 A * | 4/2011 | | |
| JP | 2014-209611 A | 11/2014 | | |
| JP | 2015-134745 A | 7/2015 | | |
| JP | 2015-151352 A | 8/2015 | | |
| JP | 2015-205831 A | 11/2015 | | |
| JP | 2016-028421 A | 2/2016 | | |
| JP | 2016-147851 A | 8/2016 | | |
| JP | 2016-225618 A | 12/2016 | | |
| JP | 2016-225619 A | 12/2016 | | |
| JP | 2017-069562 A | 4/2017 | | |
| JP | 2017-108108 A | 6/2017 | | |
| JP | 2017-119682 A | 7/2017 | | |
| JP | 2019-532951 | 11/2019 | | |
| JP | 2019-532952 | 11/2019 | | |
| KR | 2015-0084662 A | 7/2015 | | |
| KR | 2015-0132837 A | 11/2015 | | |
| KR | 2015-0133998 A | 12/2015 | | |
| KR | 2015-0136942 A | 12/2015 | | |
| KR | 2016-0007380 A | 1/2016 | | |
| KR | 2016-0140393 A | 12/2016 | | |
| KR | 2018-0063651 A | 6/2018 | | |
| KR | 2018-0095919 A | 8/2018 | | |
| KR | 2019-0059949 A | 5/2019 | | |
| TW | 201443058 | 11/2014 | | |
| TW | 201527302 | 7/2015 | | |
| TW | 201736378 | 10/2017 | | |
| WO | WO 2014/157599 A1 | 10/2014 | | |
| WO | WO 2015/037675 A1 | 3/2015 | | |
| WO | WO 2015/105315 A1 | 7/2015 | | |
| WO | WO 2015/108301 A1 | 7/2015 | | |
| WO | WO-2015182872 A1 * | 12/2015 | | H01L 51/0054 |
| WO | WO 2016/153283 A1 | 9/2016 | | |
| WO | WO 2016/193845 A1 | 12/2016 | | |
| WO | WO-2017/055963 | 4/2017 | | |
| WO | WO 2017/109637 A1 | 6/2017 | | |
| WO | WO 2017/186760 A1 | 11/2017 | | |
| WO | WO 2018/060218 A1 | 4/2018 | | |
| WO | WO 2018/060307 A1 | 4/2018 | | |
| WO | WO-2018060307 A1 * | 4/2018 | | C07D 491/04 |
| WO | WO 2018/234932 A1 | 12/2018 | | |

OTHER PUBLICATIONS

Written Opinion re Application No. PCT/IB2018/054222, dated Sep. 18, 2018.

"Screen for Chemicals that Extend Yeast Lifespan," https://pubchem.ncbi.nlm.nih.gov/assay/assay.cgi?aid=775, 2007, PubChem BioAssay.

"SMR000047385," https://pubchem.ncbi.nlm.nih.gov/summary/summary.cgi?cid=6603401&loc=ec_rcs, May 25, 2006, PubChem Compound.

"MLS000039550," https://pubchem.ncbi.nlm.nih.gov/summary/summary.cgi?cid=663679&loc=ec_rcs, Jun. 29, 2005, PubChem Compound.

"MLS000558491," https://pubchem.ncbi.nlm.nih.gov/summary/summary.cgi?cid=9551646&loc=ec_rcs, Oct. 20, 2006, PubChem Compound.

Goled, S.N. et al., "Synthesis and Reactions of 2-Substituted 4-Hydrazinobenzofuro [3,2-d] Pyrimidines and Their Antibacterial Activity," Oriental Journal of Chemistry, 1997, vol. 13, No. 1, pp. 73-75.

Tolkunov, S.V. et al., "Synthesis and Reactions of 2,4-Disubstituted Benzo[b]Furano, Benzo[b]Thieno and Indolo[3,2-d]-1,3-Oxazinium Salts," Chemistry of Heterocyclic Compounds, 1990, vol. 26, No. 11, pp. 1310-1312.

Zhao, Y. et al., "Synthesis, X-ray Structure and Antitumor Activity of 4-(1,3,4-thiadiazole-2-ylthio)benzo[4,5]furo[3,2-d]pyrimidine Derivatives," Chinese Journal of Organic Chemistry, 2010, vol. 30, No. 7, pp. 1093-1097.

Taiwanese Office Action (Application No. 107121057) Dated Jan. 13, 2022.

Peng, Q. et al., "Research Progress on Materials for Organic Light-emitting Diodes(OLEDs)," Materials Reports A: Overview, Mar. 31, 2015, vol. 29, No. 3, pp. 41-56.

Chinese Office Action (Application No. 201880041565.0) Dated Jan. 27, 2022.

\* cited by examiner

ORGANIC COMPOUND, LIGHT-EMITTING ELEMENT, LIGHT-EMITTING DEVICE, ELECTRONIC DEVICE, AND LIGHTING DEVICE

TECHNICAL FIELD

One embodiment of the present invention relates to a compound having a benzofuropyrimidine skeleton or a benzothienopyrimidine skeleton to which a condensed ring is directly bonded. Another embodiment of the present invention relates to a light-emitting element including the compound. Another embodiment of the present invention relates to a display device including the light-emitting element, an electronic device including the light-emitting element, and a lighting device including the light-emitting element.

One embodiment of the present invention relates to an organic compound, a light-emitting element, a light-emitting device, an electronic device, and a lighting device. Note that one embodiment of the present invention is not limited to the above technical field. That is, one embodiment of the present invention relates to an object, a method, a manufacturing method, or a driving method. In addition, one embodiment of the present invention relates to a process, a machine, manufacture, and a composition of matter. Specific examples include a semiconductor device, a display device, and a liquid crystal display device.

BACKGROUND ART

A light-emitting element including an EL layer between a pair of electrodes (also referred to as an organic EL element) has features such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*: T*=1:3. Since the spectrum of light emitted from a light-emitting substance depends on the light-emitting substance, the use of different types of organic compounds as light-emitting substances makes it possible to obtain light-emitting elements that exhibit various colors.

In order to improve the element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

DISCLOSURE OF INVENTION

In development of light-emitting elements, organic compounds used in the light-emitting elements are very important for improving the characteristics. Thus, an object of one embodiment of the present invention is to provide a novel organic compound. That is, an object is to provide a novel organic compound that is effective in improving the element characteristics and reliability. Another object of one embodiment of the present invention is to provide a novel organic compound that can be used in a light-emitting element. Another object of one embodiment of the present invention is to provide a novel organic compound that can be used in an EL layer of a light-emitting element. Another object is to provide a highly efficient, highly reliable, and novel light-emitting element using a novel organic compound of one embodiment of the present invention. Another object is to provide a novel light-emitting device, a novel electronic device, or a novel lighting device. Note that the description of these objects does not disturb the existence of other objects. One embodiment of the present invention does not necessarily achieve all the objects. Other objects will be apparent from and can be derived from the description of the specification, the drawings, the claims, and the like.

One embodiment of the present invention is an organic compound having a benzofuropyrimidine skeleton or a benzothienopyrimidine skeleton, which is represented by General Formula (G1).

[Chemical Formula 1]

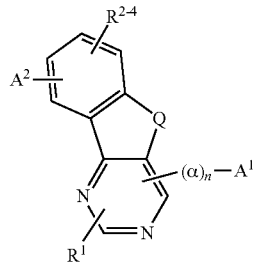

(G1)

In General Formula (G1), Q represents oxygen or sulfur; a represents a substituted or unsubstituted arylene group having 6 to 13 carbon atoms; n represents an integer of 0 to 4; $A^1$ represents a group including an aryl group or a heteroaryl group and having 6 to 100 carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

Another embodiment of the present invention is an organic compound represented by General Formula (G2).

[Chemical Formula 2]

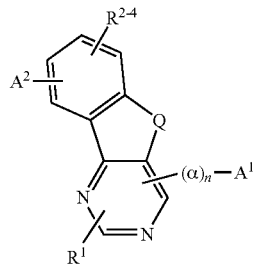

(G2)

In General Formula (G2), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

Another embodiment of the present invention is an organic compound represented by General Formula (G3).

[Chemical Formula 3]

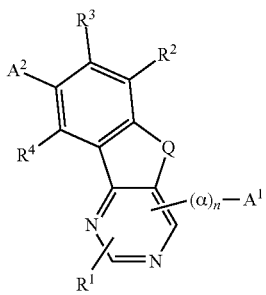

(G3)

In General Formula (G3), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

Another embodiment of the present invention is an organic compound represented by General Formula (G4).

[Chemical Formula 4]

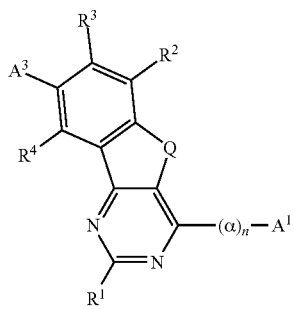

(G4)

In General Formula (G4), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^3$ represents a condensed ring.

In General Formula (G4), $A^3$ is preferably a condensed aromatic hydrocarbon group having a naphthalene skeleton, a fluorene skeleton, a phenanthrene skeleton, a triphenylene skeleton, or the like.

Another embodiment of the present invention is an organic compound represented by General Formula (G5).

[Chemical Formula 5]

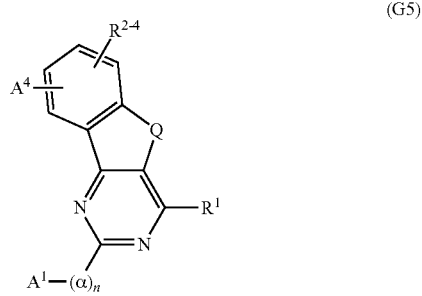

(G5)

In General Formula (G5), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^4$ represents a condensed ring.

In General Formula (G5), $A^4$ is preferably a condensed aromatic hydrocarbon group having a naphthalene skeleton, a fluorene skeleton, a phenanthrene skeleton, a triphenylene skeleton, or the like.

Another embodiment of the present invention is an organic compound represented by General Formula (G6).

[Chemical Formula 6]

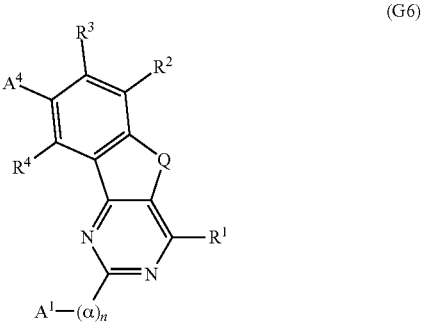

(G6)

In General Formula (G6), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^4$ represents a condensed ring.

In order to obtain a long lifetime light-emitting element, the condensed ring is preferably bonded to the 8-position of a benzofuro[3,2-d]pyrimidine skeleton or a benzothieno[3,2-d]pyrimidine skeleton as shown in General Formulae (G3), (G4), and (G6).

General Formulae (G1) to (G6) are characterized in that $A^1$ has a skeleton with a hole-transport property. The hole-transport skeleton is preferably any of a diarylamino group, a condensed aromatic hydrocarbon ring, and a π-electron rich condensed heteroaromatic ring.

In General Formulae (G2) to (G6), $A^1$ is preferably a substituted or unsubstituted condensed aromatic hydrocarbon ring or a substituted or unsubstituted π-electron rich condensed heteroaromatic ring. In particular, $A^1$ is preferably a π-electron rich condensed heteroaromatic ring in terms of hole-transport properties, and more preferably a substituted or unsubstituted condensed heteroaromatic ring having any one of a dibenzothiophene skeleton, a dibenzofuran skeleton, and a carbazole skeleton.

In contrast, General Formulae (G1) to (G6) are characterized in that the condensed rings of $A^2$, $A^3$, and $A^4$ are independently a substituted or unsubstituted condensed aromatic hydrocarbon ring or a substituted or unsubstituted π-electron rich condensed heteroaromatic ring. Specifically, $A^2$, $A^3$, and $A^4$ are independently a condensed ring having any one of a substituted or unsubstituted dibenzothiophene skeleton, a substituted or unsubstituted dibenzofuran skeleton, a substituted or unsubstituted carbazole skeleton, a substituted or unsubstituted naphthalene skeleton, a substituted or unsubstituted fluorene skeleton, a substituted or unsubstituted triphenylene skeleton, and a substituted or unsubstituted phenanthrene skeleton. Note that the condensed aromatic hydrocarbon ring is preferably an unsaturated condensed aromatic hydrocarbon ring. The unsaturated condensed aromatic hydrocarbon ring is preferably a condensed aromatic hydrocarbon ring composed of carbon atoms that have no $sp^3$ bonds; specifically, a naphthalene ring, a triphenylene ring, a phenanthrene ring, or the like.

In General Formulae (G1) to (G6), $A^1$, $A^2$, $A^3$, and $A^4$ are independently any one of General Formulae (A$^1$-1) to (A$^1$-17).

[Chemical Formula 7]

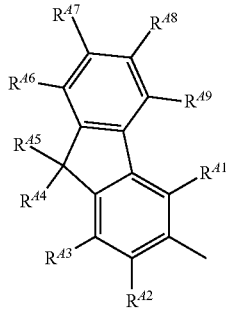
(A$^1$-1)

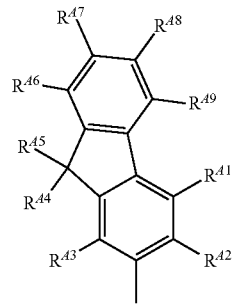
(A$^1$-2)

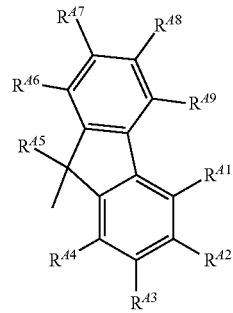
(A$^1$-3)

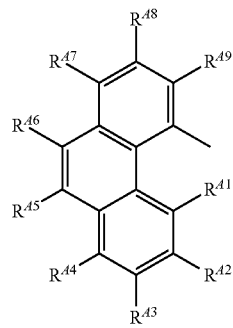
(A$^1$-4)

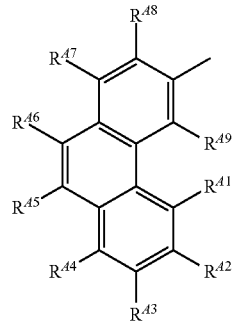
(A$^1$-5)

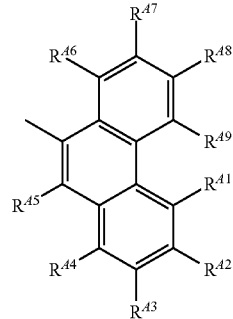
(A$^1$-6)

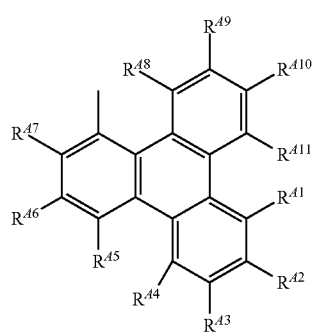 (A¹-7)
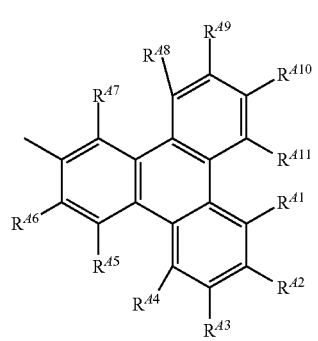 (A¹-8)
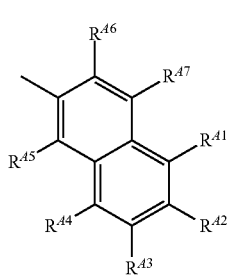 (A¹-9)
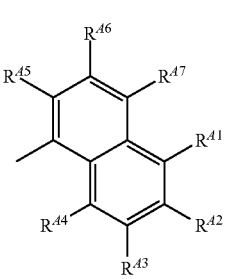 (A¹-10)
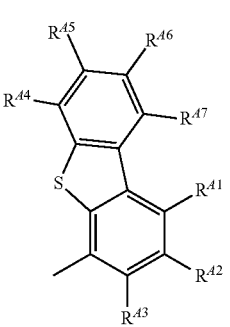 (A¹-11)
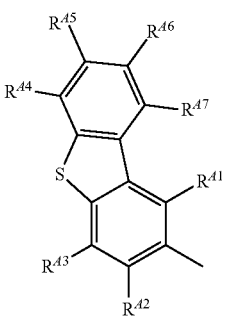 (A¹-12)
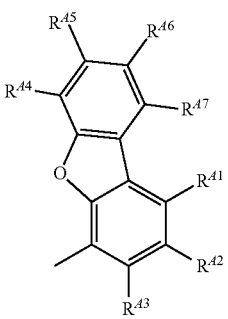 (A¹-13)
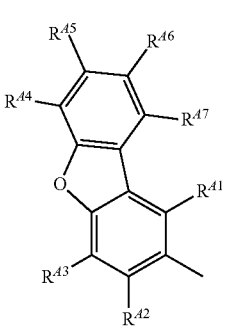 (A¹-14)
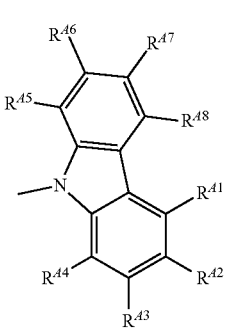 (A¹-15)
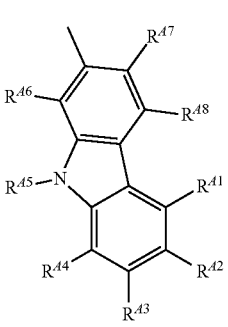 (A¹-16)

-continued

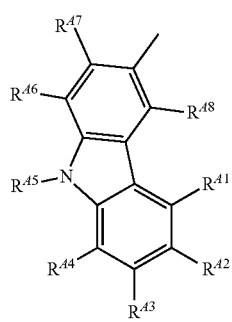
(A¹-17)

In General Formulae (A¹-1) to (A¹-17), $R^{A1}$ to $R^{A11}$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms.

In General Formulae (G1) to (G6), a is an organic compound represented by any one of General Formulae (Ar-1) to (Ar-17).

[Chemical Formula 8]

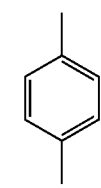
(Ar-1)

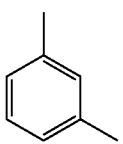
(Ar-2)

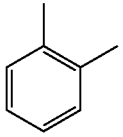
(Ar-3)

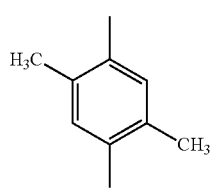
(Ar-4)

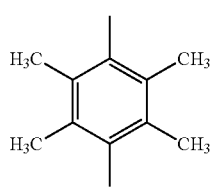
(Ar-5)

-continued

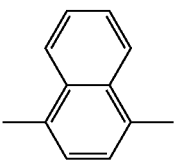
(Ar-6)

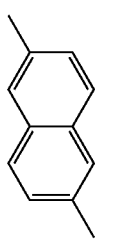
(Ar-7)

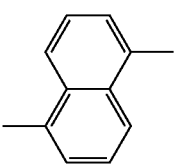
(Ar-8)

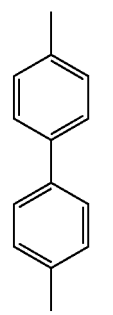
(Ar-9)

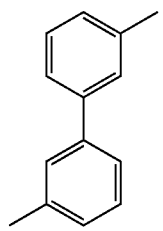
(Ar-10)

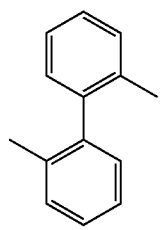
(Ar-11)

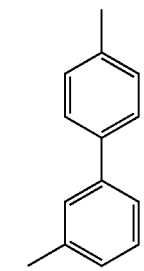
(Ar-12)

(Ar-13) 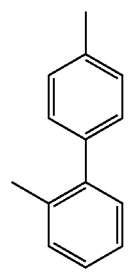
(Ar-14) 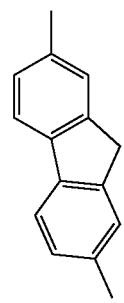
(Ar-15) 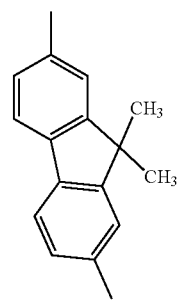
(Ar-16) 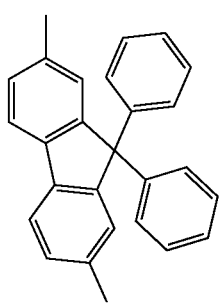
(Ar-17) 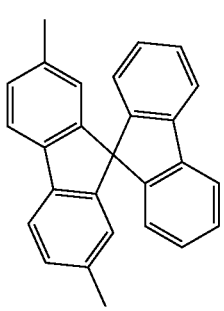
(Ar-18) 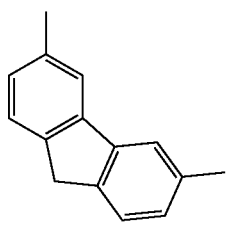
Another embodiment of the present invention is an organic compound represented by Structural Formula (100), (101), or (102).
[Chemical Formula 9]
(100) 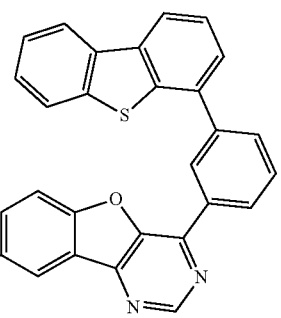
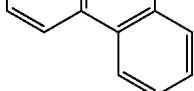
(101) 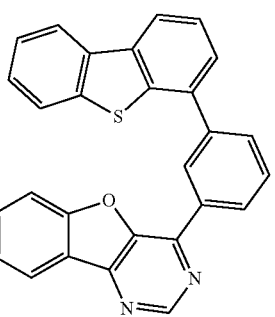
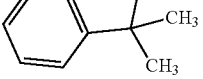

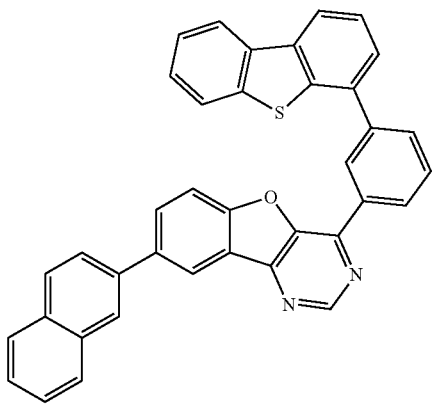

(102)

Another embodiment of the present invention is a light-emitting element including the aforementioned organic compound of one embodiment of the present invention. Note that the present invention also includes a light-emitting element containing a host material as well as the aforementioned organic compound.

Another embodiment of the present invention is a light-emitting element including the aforementioned organic compound of one embodiment of the present invention. Note that the present invention also includes a light-emitting element that uses the organic compound of one embodiment of the present invention for an EL layer between a pair of electrodes and a light-emitting layer in the EL layer. In addition to the light-emitting element, a light-emitting device including a transistor, a substrate, and the like is also included in the scope of the invention. Furthermore, the scope of the invention includes, in addition to the light-emitting device, an electronic device and a lighting device that include a microphone, a camera, an operation button, an external connection portion, a housing, a cover, a support, a speaker, and the like.

In addition, the scope of one embodiment of the present invention includes a light-emitting device including a light-emitting element, and a lighting device including the light-emitting device. Accordingly, the light-emitting device in this specification refers to an image display device or a light source (including a lighting device). In addition, the light-emitting device includes the following in its category: a module in which a connector such as a flexible printed circuit (FPC) or a tape carrier package (TCP) is attached to a light-emitting device; a module in which a printed wiring board is provided at the end of a TCP; and a module in which an integrated circuit (IC) is directly mounted on a light-emitting element by a chip on glass (COG) method.

According to one embodiment of the present invention, a novel organic compound can be provided. That is, a novel organic compound that is effective in improving the element characteristics can be provided. According to another embodiment of the present invention, a novel organic compound that can be used in a light-emitting element can be provided. According to another embodiment of the present invention, a novel organic compound that can be used in an EL layer of a light-emitting element can be provided. In addition, a highly efficient, highly reliable, and novel light-emitting element using a novel organic compound of one embodiment of the present invention can be provided. Furthermore, a novel light-emitting device, a novel electronic device, or a novel lighting device can be provided. Note that the description of these effects does not disturb the existence of other effects. One embodiment of the present invention does not necessarily achieve all the effects. Other effects will be apparent from and can be derived from the description of the specification, the drawings, the claims, and the like.

BEST MODE FOR CARRYING OUT THE INVENTION

Figure 1A:
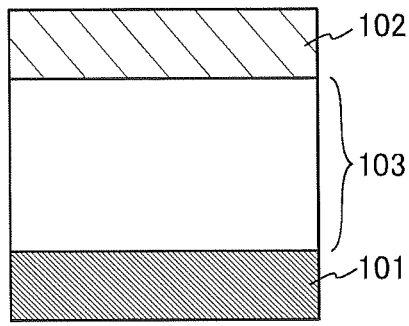
FIGS. 1A to 1E illustrate structures of light-emitting elements.

Embodiments of the present invention will be described in detail below with reference to drawings. Note that the present invention is not limited to the following description, and the modes and details of the present invention can be modified in various ways without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In describing structures of the invention with reference to the drawings in this specification and the like, the same components in different diagrams are commonly denoted by the same reference numeral.

Embodiment 1

In this embodiment, organic compounds of embodiments of the present invention will be described.

One embodiment of the present invention is an organic compound having a benzofuropyrimidine skeleton or a benzothienopyrimidine skeleton, which is represented by General Formula (G1).

[Chemical Formula 10]

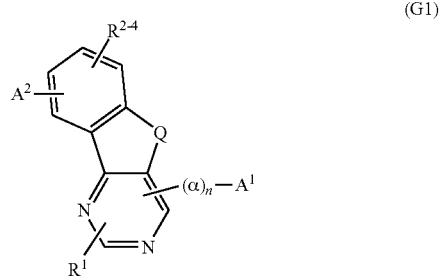

(G1)

In General Formula (G1), Q represents oxygen or sulfur; a represents a substituted or unsubstituted arylene group having 6 to 13 carbon atoms; n represents an integer of 0 to 4; $A^1$ represents a group including aryl or heteroaryl and having 6 to 100 carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

In General Formula (G1), the condensed ring ($A^2$) is directly bonded to a benzene side of the benzofuropyrimidine skeleton or the benzothienopyrimidine skeleton, which contributes to improved thermophysical properties and reliability of a light-emitting element.

Another embodiment of the present invention is an organic compound represented by General Formula (G2).

[Chemical Formula 11]

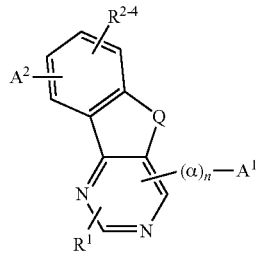

(G2)

In General Formula (G2), Q represents oxygen or sulfur; a, represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

In General Formula (G2), the condensed ring ($A^2$) is directly bonded to a benzene side of the benzofuropyrimidine skeleton or the benzothienopyrimidine skeleton, which contributes to improved thermophysical properties and reliability of a light-emitting element.

Another embodiment of the present invention is an organic compound represented by General Formula (G3).

[Chemical Formula 12]

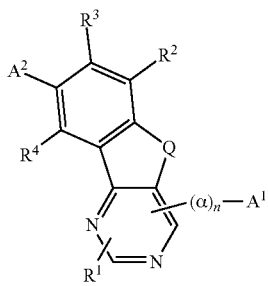

(G3)

In General Formula (G3), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

The condensed ring bonded to the 8-position of the benzofuropyrimidine skeleton or the benzothienopyrimidine skeleton as shown in General Formula (G3) facilitates synthesis of a material with a reduced amount of impurities such as halide, which adversely affects the properties and reliability of the element, and therefore, offers an advantage in terms of raw material costs. That is, a long lifetime light-emitting element can be obtained. Note that similar effects are produced by $A^3$ in General Formula (G4) and $A^4$ in General Formula (G6).

Furthermore, the condensed ring bonded to the 8-position of the benzofuropyrimidine skeleton or the benzothienopyrimidine skeleton as shown in General Formula (G3) enables a high T1 level as well as electrochemical stability and high film quality. Note that similar effects are produced by $A^3$ in General Formula (G4) and $A^4$ in General Formula (G6).

In General Formula (G3), n is preferably 1 or 2.

In General Formula (G3), the condensed ring ($A^2$) is directly bonded to a benzene side of the benzofuropyrimidine skeleton or the benzothienopyrimidine skeleton, which contributes to improved thermophysical properties and reliability of a light-emitting element.

Another embodiment of the present invention is an organic compound represented by General Formula (G4).

[Chemical Formula 13]

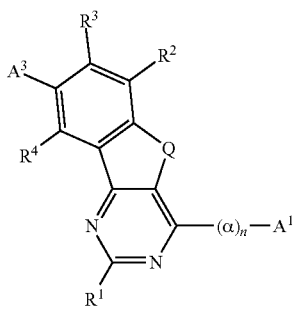

(G4)

In General Formula (G4), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^3$ represents a condensed ring.

In General Formula (G4), $A^3$ is preferably a condensed aromatic hydrocarbon group having a naphthalene skeleton, a fluorene skeleton, a phenanthrene skeleton, a triphenylene skeleton, or the like.

In General Formula (G4), $A^1$ is preferably a substituted or unsubstituted π-electron rich condensed heteroaromatic ring having a dibenzothiophene skeleton, a dibenzofuran skeleton, or a carbazole skeleton.

In General Formula (G4), n is preferably 1 or 2.

In General Formula (G4), the condensed ring ($A^3$) is directly bonded to a benzene side of the benzofuropyrimidine skeleton or the benzothienopyrimidine skeleton, which contributes to improved thermophysical properties and reliability of a light-emitting element.

Another embodiment of the present invention is an organic compound represented by General Formula (G5).

[Chemical Formula 14]

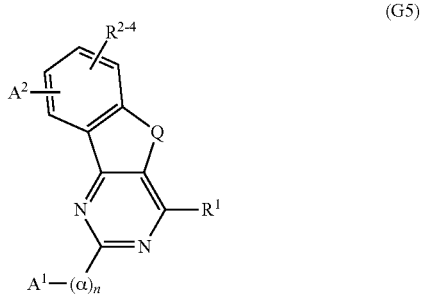

(G5)

In General Formula (G5), Q represents oxygen or sulfur; a represents a substituted or unsubstituted arylene group having 6 to 13 carbon atoms; n represents an integer of 0 to 4; $A^1$ represents a substituted or unsubstituted aryl group having 6 to 100 carbon atoms or a substituted or unsubstituted heteroaryl group having 6 to 100 carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^4$ represents a condensed ring.

In General Formula (G5), $A^4$ is preferably a condensed aromatic hydrocarbon group having a naphthalene skeleton, a fluorene skeleton, a phenanthrene skeleton, a triphenylene skeleton, or the like.

In General Formula (G5), $A^1$ is preferably a substituted or unsubstituted π-electron rich condensed heteroaromatic ring having a dibenzothiophene skeleton, a dibenzofuran skeleton, or a carbazole skeleton.

In General Formula (G5), n is preferably 1 or 2.

In General Formula (G5), the condensed ring ($A^4$) is directly bonded to a benzene side of the benzofuropyrimidine skeleton or the benzothienopyrimidine skeleton, which contributes to improved thermophysical properties and reliability of a light-emitting element.

Another embodiment of the present invention is an organic compound represented by General Formula (G6).

[Chemical Formula 15]

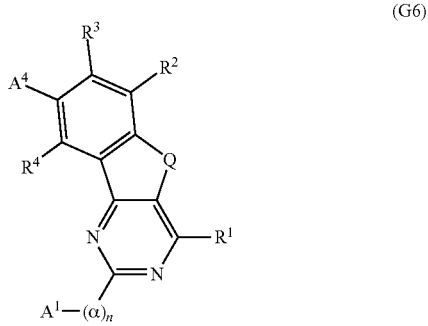

(G6)

In General Formula (G6), Q represents oxygen or sulfur; α represents a substituted or unsubstituted arylene group having 6 to 13 carbon atoms; n represents an integer of 0 to 4; $A^1$ represents a substituted or unsubstituted aryl group having 6 to 100 total carbon atoms or a substituted or unsubstituted heteroaryl group having 6 to 100 total carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^4$ represents a condensed ring.

In General Formula (G6), $A^4$ is preferably a π-electron rich condensed heteroaromatic ring having a dibenzothiophene skeleton, a dibenzofuran skeleton, a carbazole skeleton, or the like.

In General Formula (G6), $A^4$ is preferably bonded to the 8-position of the benzofuropyrimidine skeleton or the benzothienopyrimidine skeleton.

In General Formula (G6), $A^1$ is preferably a substituted or unsubstituted π-electron rich condensed heteroaromatic ring having a dibenzothiophene skeleton, a dibenzofuran skeleton, or a carbazole skeleton.

In General Formula (G6), n is preferably 1 or 2.

In General Formula (G6), the condensed ring ($A^4$) is directly bonded to a benzene side of the benzofuropyrimidine skeleton or the benzothienopyrimidine skeleton, which contributes to improved thermophysical properties and reliability of a light-emitting element.

One embodiment of the present invention is characterized in that $A^1$ in General Formulae (G1) to (G6) has a skeleton with a hole-transport property. The compounds represented by General Formulae (G1) to (G6) each have an electron-transport property derived from a benzofuro[3,2-d]pyrimidine skeleton or a benzothieno[3,2-d]pyrimidine skeleton; the addition of the hole-transport skeleton thereto offers a bipolar compound, which is stable for both holes and electrons. When the bipolar compound is used as a host of a light-emitting element, a carrier recombination region can be enlarged, resulting in a longer lifetime of the light-emitting element. Examples of the hole-transport skeleton include a diarylamino group, a condensed aromatic hydrocarbon ring, and a π-electron rich condensed heteroaromatic ring.

In view of the above, $A^1$ in General Formulae (G2) to (G6) is preferably a substituted or unsubstituted condensed aromatic hydrocarbon ring or a substituted or unsubstituted π-electron rich condensed heteroaromatic ring. In particular, $A^1$ is preferably a π-electron rich condensed heteroaromatic ring in terms of hole-transport properties, and more preferably a substituted or unsubstituted condensed heteroaromatic ring having any one of a dibenzothiophene skeleton, a dibenzofuran skeleton, and a carbazole skeleton. Such a condensed heteroaromatic ring including a five-membered ring has both high hole-transport properties and chemical stability.

In terms of easy synthesis and raw material costs, all of $R^1$ to $R^4$ in the organic compounds shown in this embodiment are particularly preferably hydrogen, in which case the organic compounds each have a relatively low molecular weight and are suitable for vacuum evaporation.

In contrast, General Formulae (G1) to (G6) are characterized in that the condensed rings of $A^2$, $A^3$, and $A^4$ are independently a substituted or unsubstituted condensed aromatic hydrocarbon ring or a substituted or unsubstituted π-electron rich condensed heteroaromatic ring. Among condensed rings, the aromatic condensed rings are preferably used because chemical stability due to resonance stabilization, which directly influences the lifetime of a light-emitting element, can be obtained and thermophysical properties (heat resistance) are improved.

Specifically, General Formulae (G1) to (G6) are characterized in that $A^2$, $A^3$, and $A^4$ are independently a condensed ring having any one of a substituted or unsubstituted dibenzothiophene skeleton, a substituted or unsubstituted dibenzofuran skeleton, a substituted or unsubstituted carbazole skeleton, a substituted or unsubstituted naphthalene skeleton, a substituted or unsubstituted fluorene skeleton, a substituted or unsubstituted triphenylene skeleton, and a substituted or unsubstituted phenanthrene skeleton.

Note that the condensed aromatic hydrocarbon ring is preferably an unsaturated condensed aromatic hydrocarbon ring with low ring strain in terms of chemical stability. The unsaturated condensed aromatic hydrocarbon ring is preferably a condensed aromatic hydrocarbon ring composed of carbon atoms that have no spa bonds; specifically, a naphthalene ring, a triphenylene ring, or a phenanthrene ring.

In General Formulae (G1) to (G6), A', $A^2$, $A^3$, and $A^4$ are independently any one of General Formulae ($A^1$-1) to ($A^1$-17).

[Chemical Formula 16]

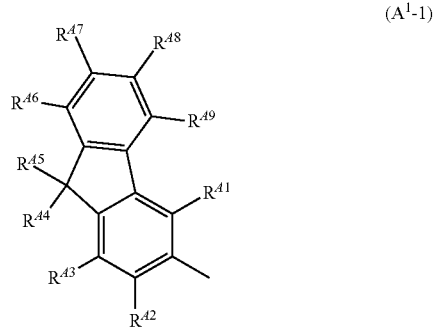

($A^1$-1)

-continued
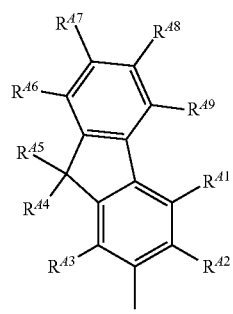
(A¹-2)
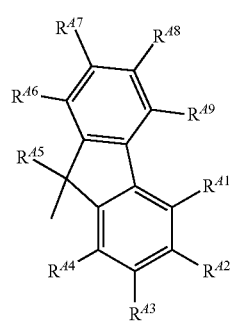
(A¹-3)
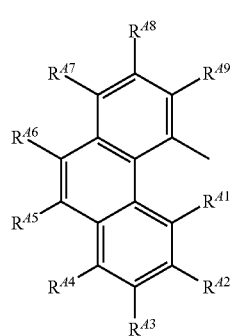
(A¹-4)
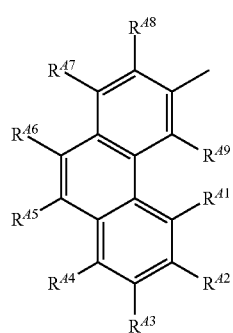
(A¹-5)
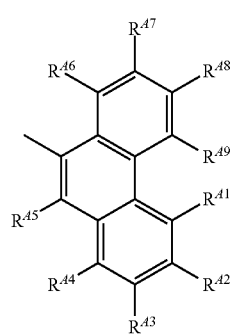
(A¹-6)
-continued
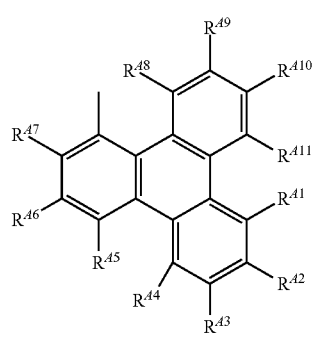
(A¹-7)
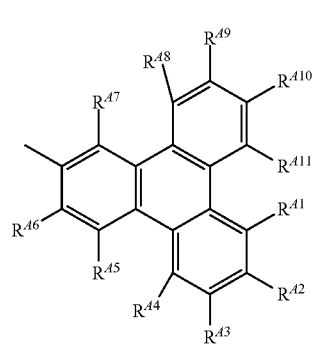
(A¹-8)
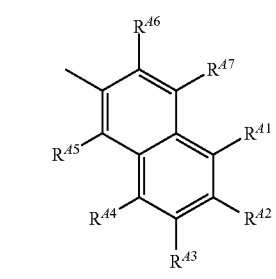
(A¹-9)
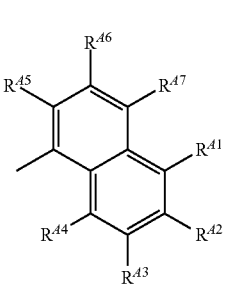
(A¹-10)
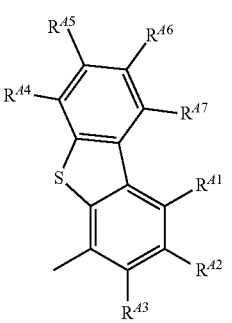
(A¹-11)

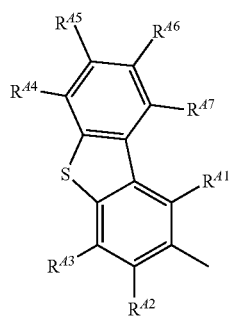

(A¹-12)

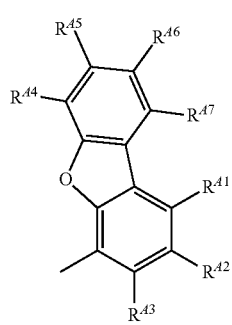

(A¹-13)

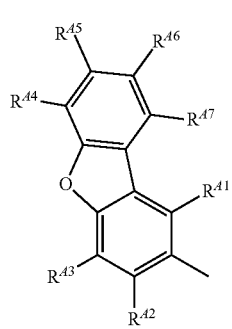

(A¹-14)

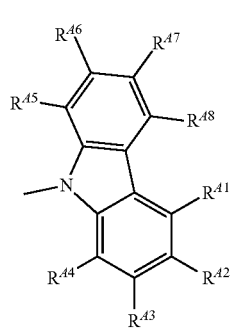

(A¹-15)

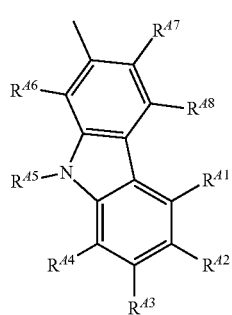

(A¹-16)

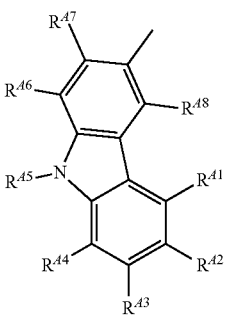

(A¹-17)

In General Formulae (A¹-1) to (A¹-17), $R^{A1}$ to $R^{A11}$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms.

In General Formulae (G1) to (G6), α is any one of General Formulae (Ar-1) to (Ar-18).

[Chemical Formula 17]

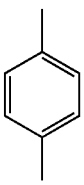

(Ar-1)

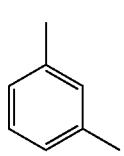

(Ar-2)

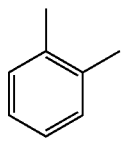

(Ar-3)

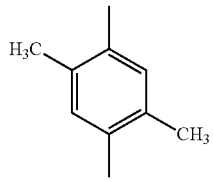

(Ar-4)

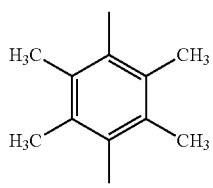

(Ar-5)

(Ar-6) 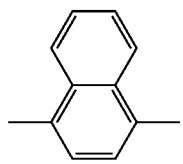
(Ar-7) 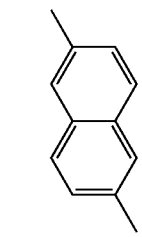
(Ar-8) 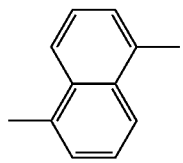
(Ar-9) 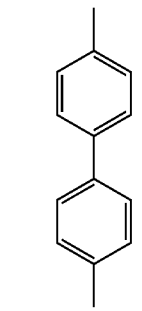
(Ar-10) 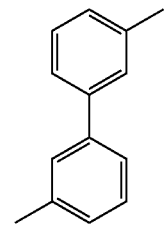
(Ar-11) 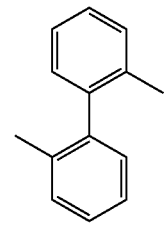
(Ar-12) 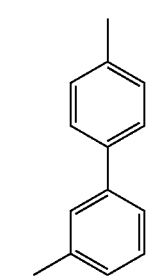
(Ar-13) 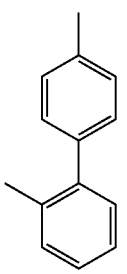
(Ar-14) 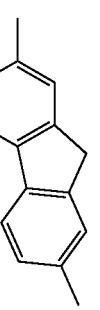
(Ar-15) 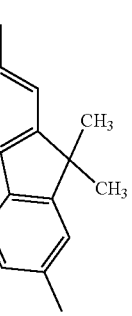
(Ar-16) 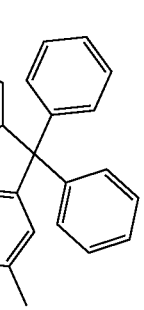
(Ar-17) 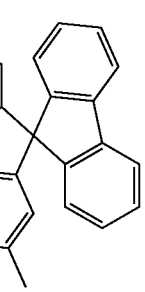

(Ar-18)

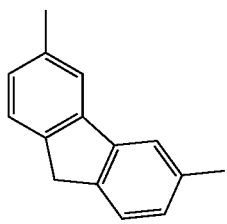

[Chemical Formula 18]

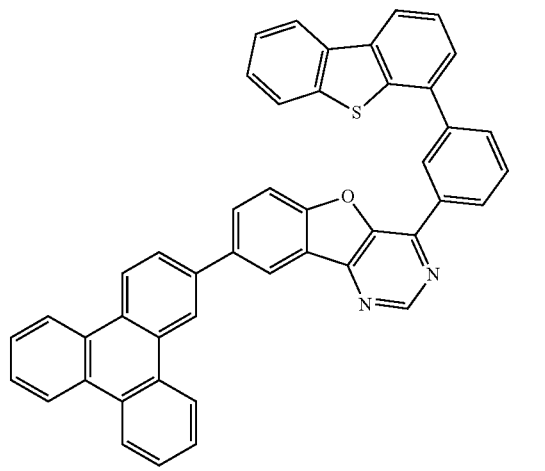
(100)

In General Formulae (G1) to (G6), in the case where any of the substituted or unsubstituted diarylamino group having 6 to 13 carbon atoms, the substituted or unsubstituted aryl group having 6 to 13 carbon atoms, the substituted or unsubstituted monocyclic saturated hydrocarbon group having 3 to 20 carbon atoms, and the substituted or unsubstituted polycyclic saturated hydrocarbon group having 7 to 10 carbon atoms has a substituent, examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, such as a cyclopentyl group, a cyclohexyl group, a cycloheptyl group, or a 8,9,10-trinorbornanyl group; and an aryl group having 6 to 12 carbon atoms, such as a phenyl group, a naphthyl group, or a biphenyl group.

Specific examples of the monocyclic saturated hydrocarbon group having 3 to 20 carbon atoms in General Formulae (G1) to (G6) include a cyclopropyl group, a cyclopentyl group, a cyclohexyl group, a cycloheptyl group, a 2-methylcyclohexyl group, a cyclooctyl group, a cyclononyl group, a cyclodecyl group, and a cycloicosyl group.

Specific examples of the polycyclic saturated hydrocarbon group having 7 to 10 carbon atoms in General Formulae (G1) to (G6) include a 8,9,10-trinorbornanyl group, a decahydronaphthyl group, and an adamantyl group.

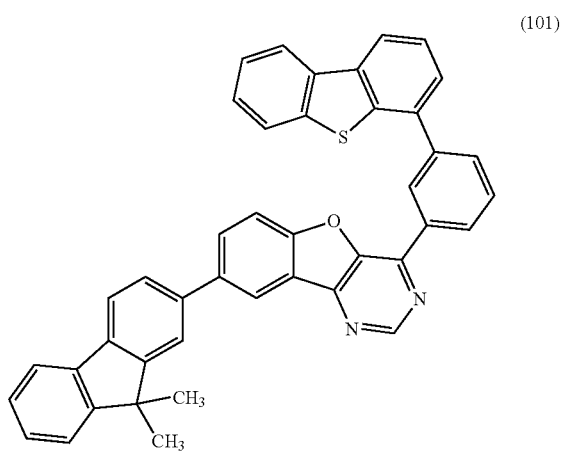
(101)

Specific examples of the aryl group having 6 to 13 carbon atoms in General Formulae (G1) to (G6) include a phenyl group, an o-tolyl group, an m-tolyl group, a p-tolyl group, a mesityl group, an o-biphenyl group, an m-biphenyl group, a p-biphenyl group, a 1-naphthyl group, a 2-naphthyl group, a fluorenyl group, and a 9,9-dimethylfluorenyl group.

Specific examples of the alkyl group having 1 to 7 carbon atoms in General Formulae (G1) to (G6) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, a 2,3-dimethylbutyl group, and an n-heptyl group.

Next, specific structural formulae of the aforementioned organic compounds of embodiments of the present invention are shown below. Note that the present invention is not limited to these formulae.

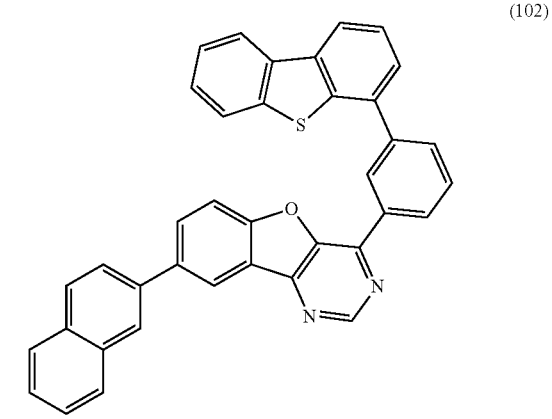
(102)

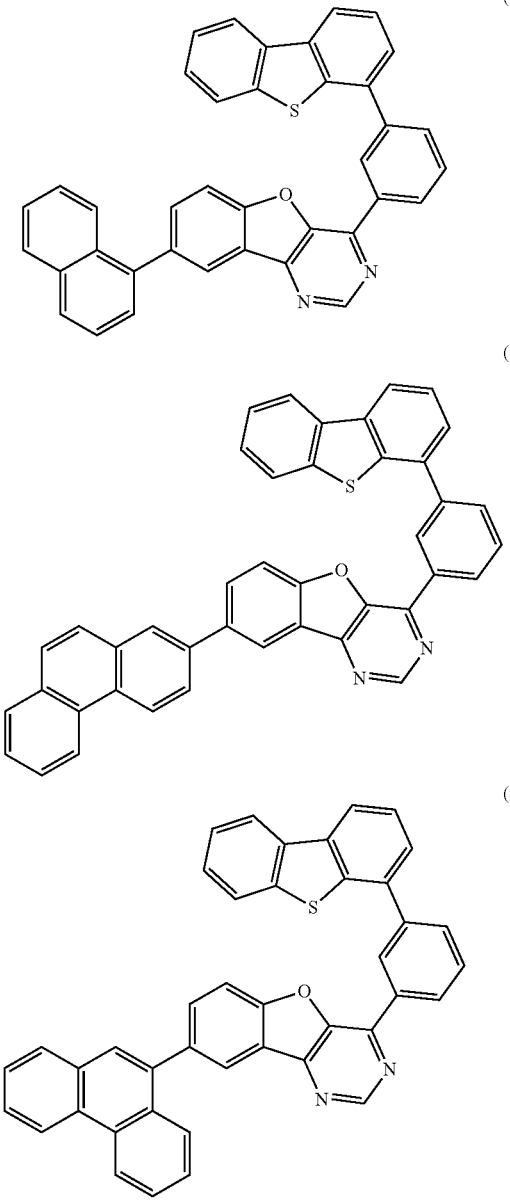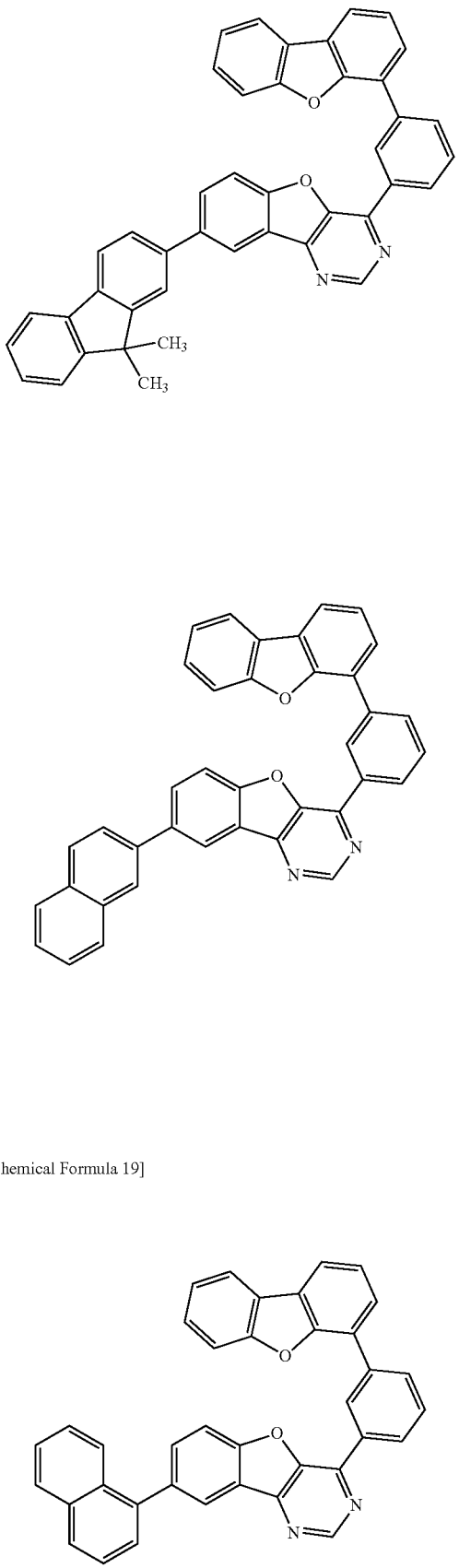
[Chemical Formula 19]

(110)
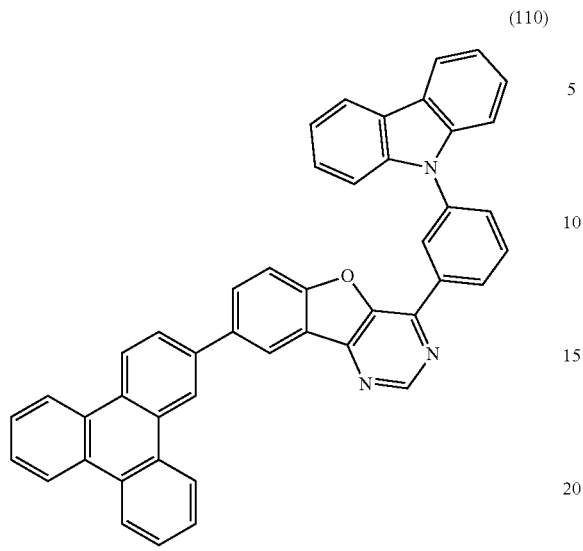
(111)
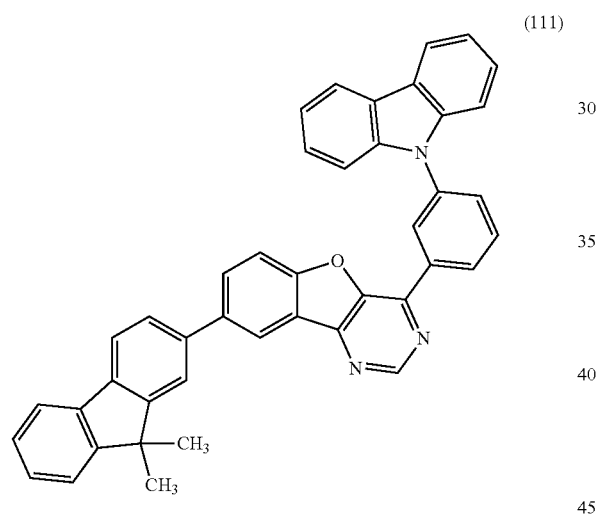
(112)
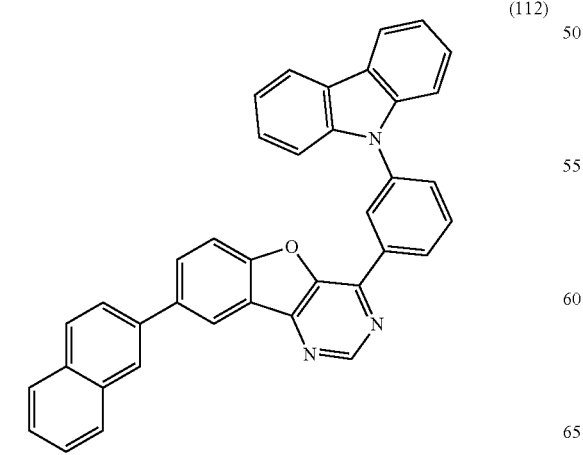
(113)
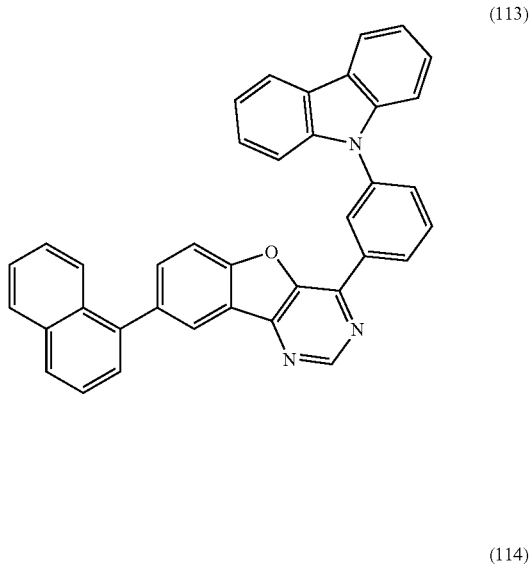
(114)
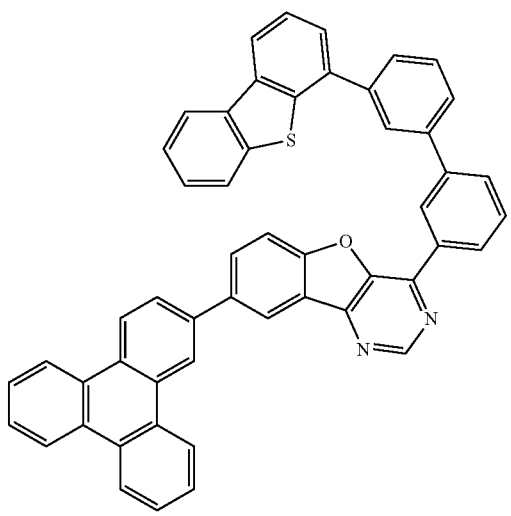
(115)
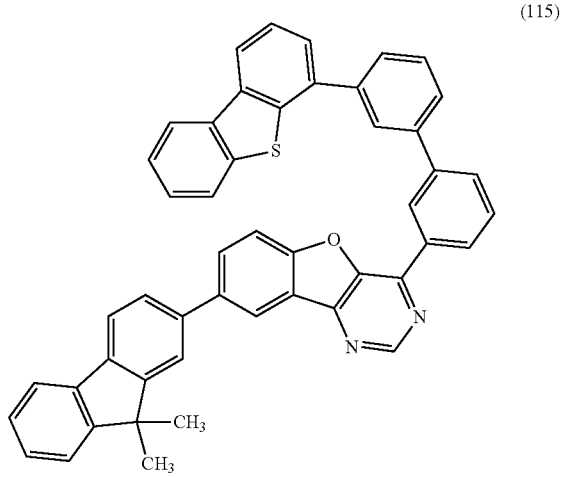

-continued
(116)
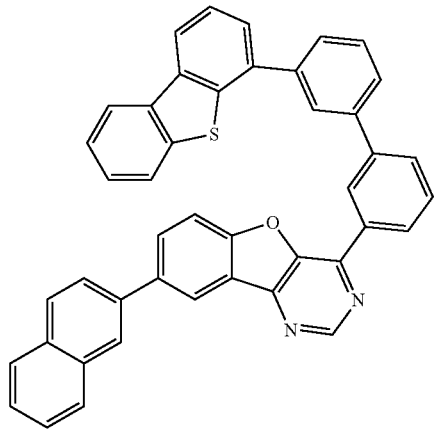
(117)
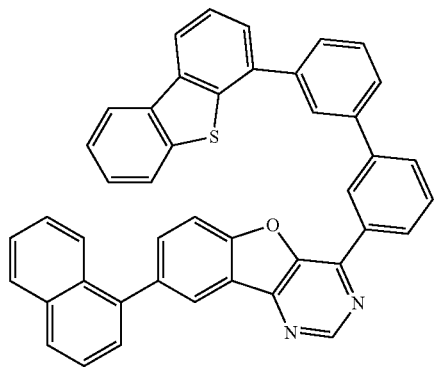
[Chemical Formula 20]
(118)
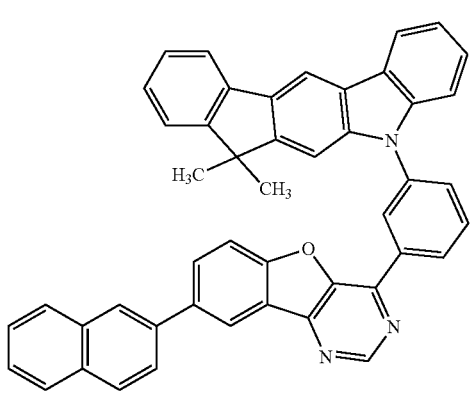
-continued
(119)
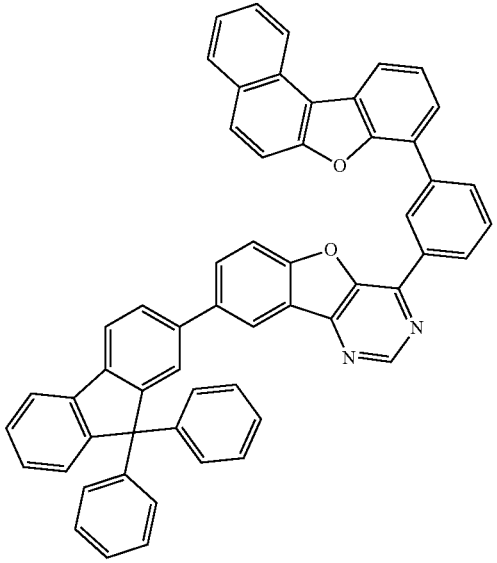
(120)
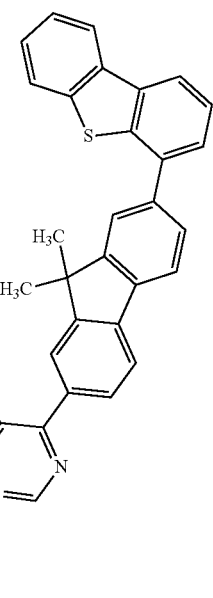
(121)
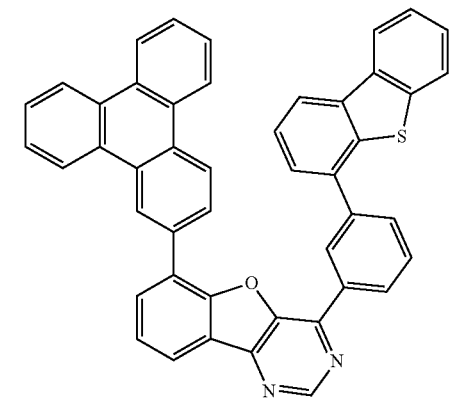

(122) 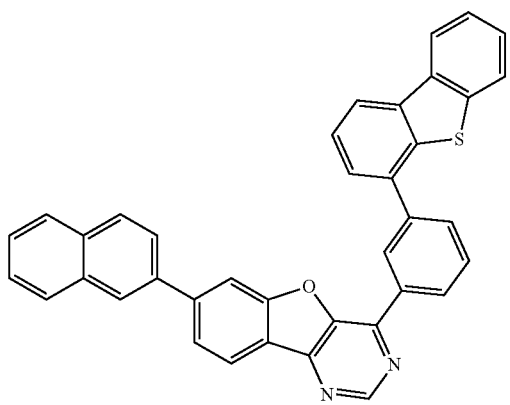
(123) 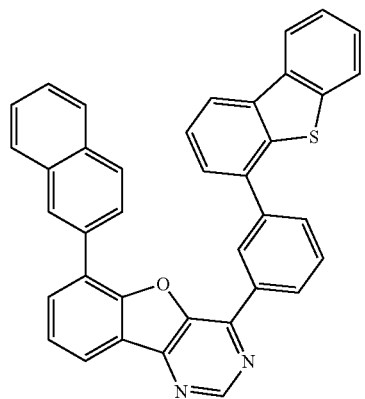
(124) 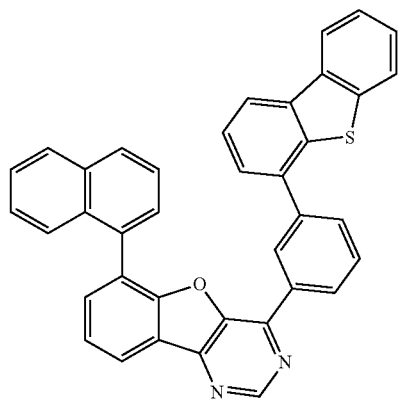
(125) 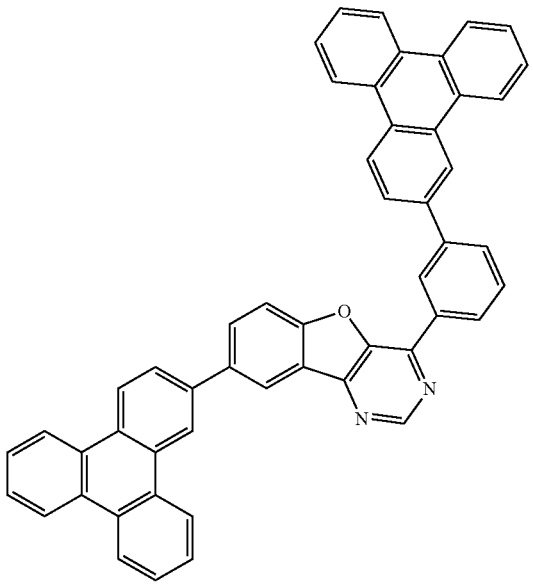
(126) 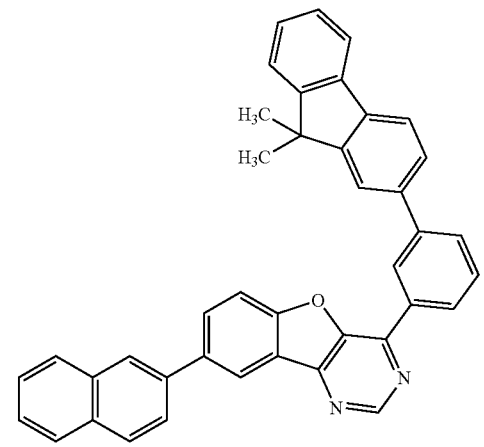
[Chemical Formula 21]
(127) 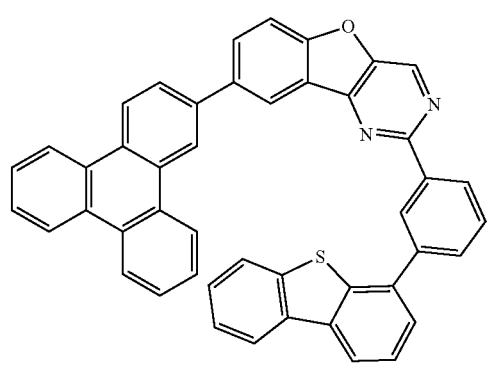

-continued
(128)
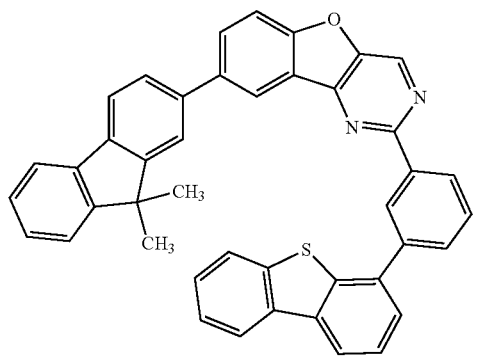
(129)
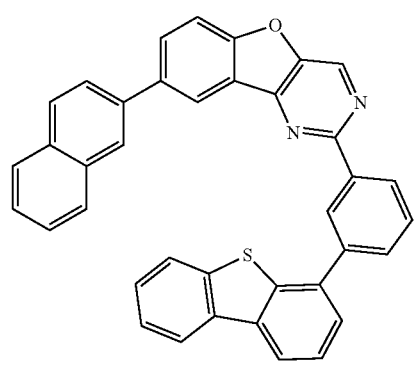
(130)
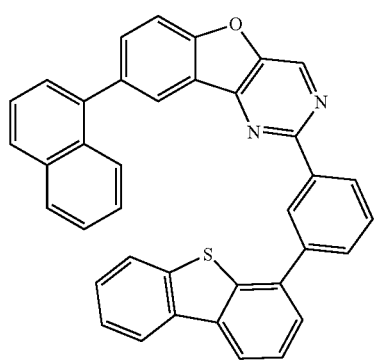
(131)
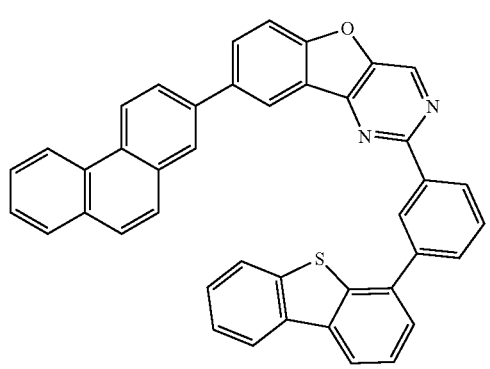
-continued
(132)
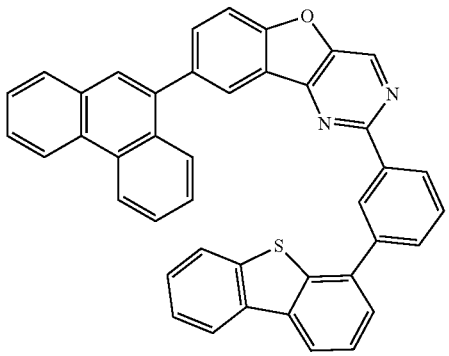
(133)
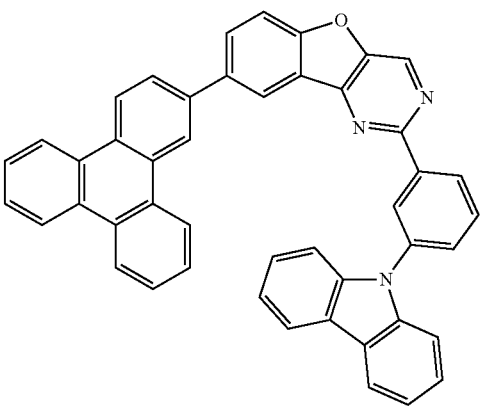
(134)
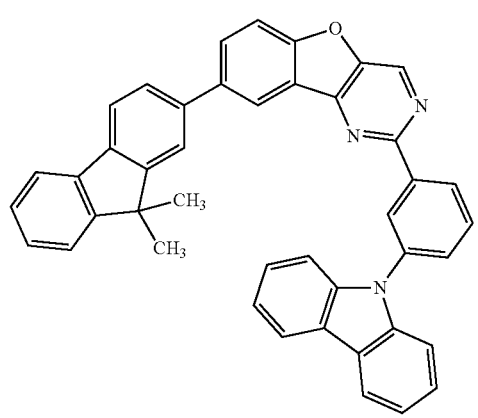
(135)
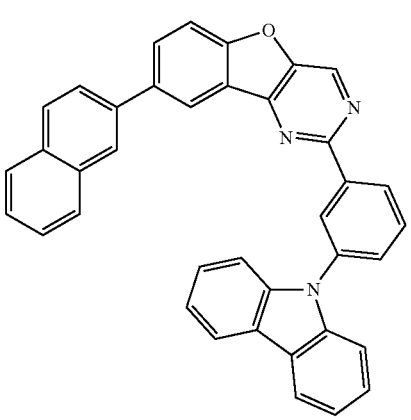

(136)
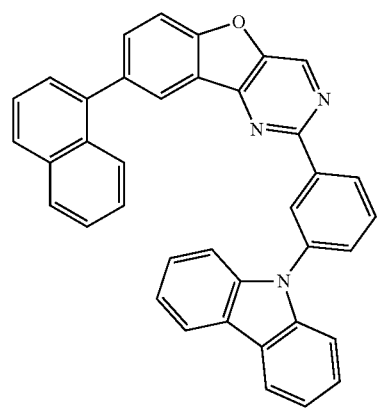
(137)
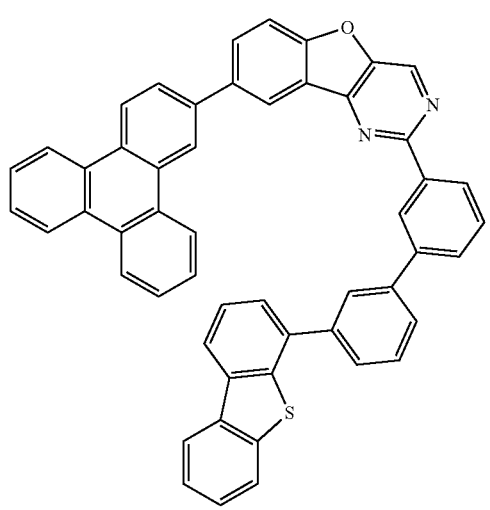
(138)
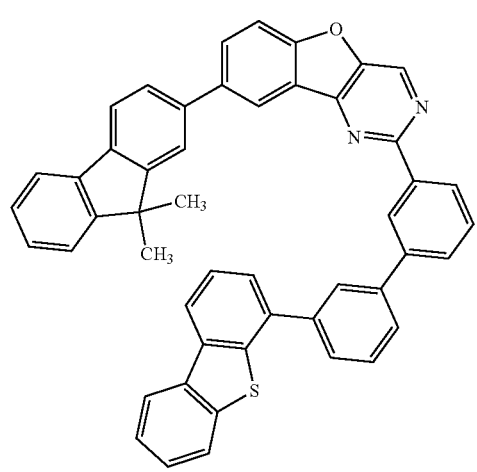
[Chemical Formula 22]
(139)
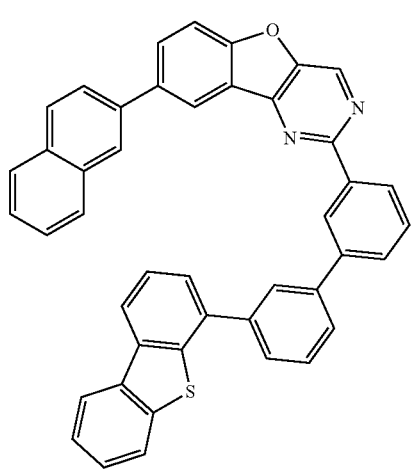
(140)
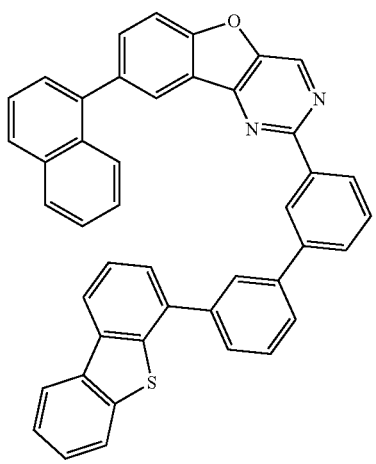
(141)
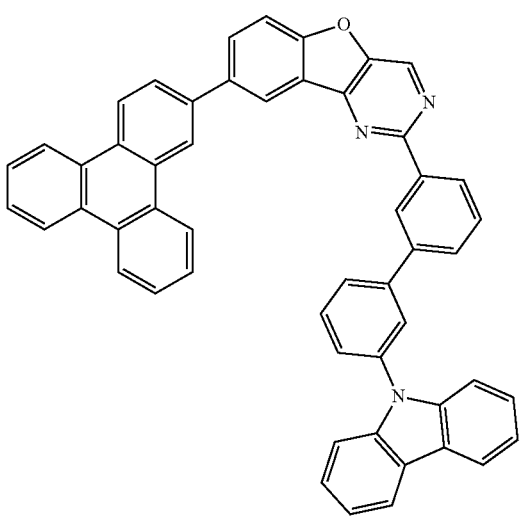

(142)
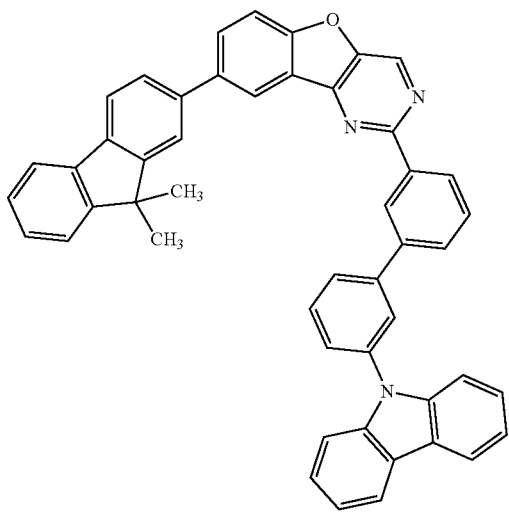
(143)
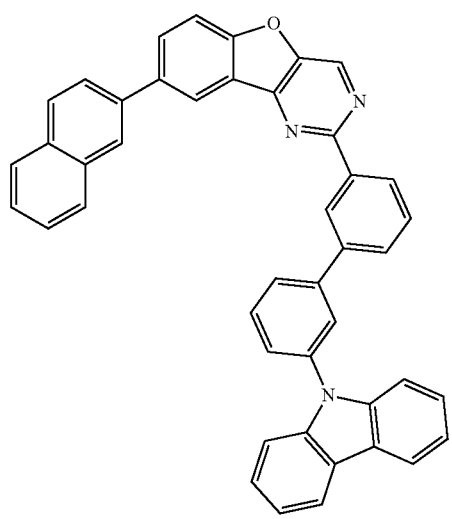
(144)
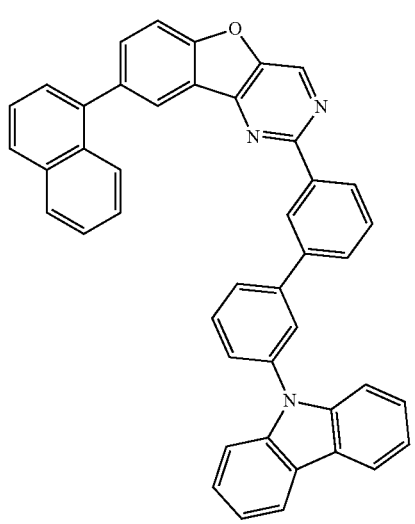
(145)
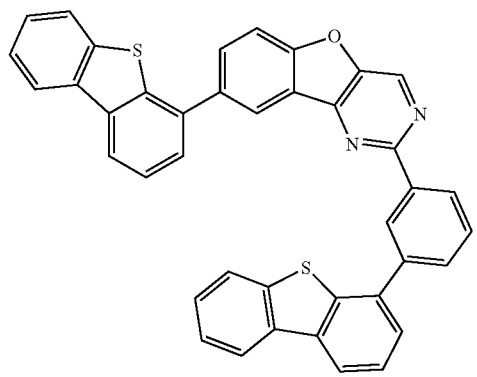
(146)
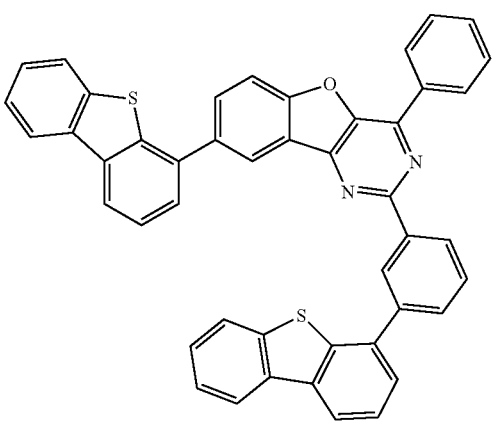
(147)
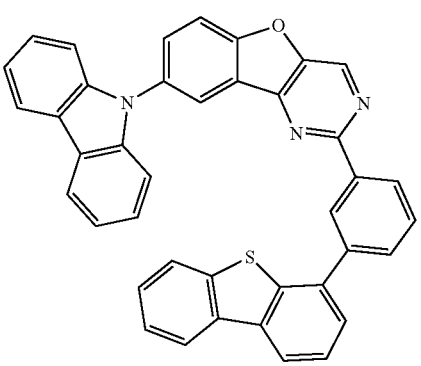

-continued (148)

(149)

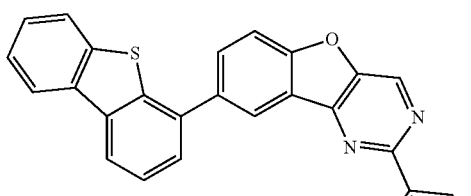

(150)

Note that the organic compounds represented by Structural Formulae (100) to (150) are examples of the organic compounds represented by General Formulae (G1) to (G6). The organic compound of one embodiment of the present invention is not limited thereto.

Next, an example of a method for synthesizing the organic compound of one embodiment of the present invention represented by General Formula (G1) will be described.

[Chemical Formula 23]

(G1)

In General Formula (G1), Q represents oxygen or sulfur; a represents a substituted or unsubstituted arylene group having 6 to 13 carbon atoms; n represents an integer of 0 to 4; $A^1$ represents a group including aryl or heteroaryl and having 6 to 100 carbon atoms; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and $A^2$ represents a condensed ring.

<<Method for Synthesizing Organic Compound Represented by General Formula (G1)>>

The organic compound represented by General Formula (G1) is a benzofuropyrimidine derivative or a benzothienopyrimidine derivative, which can be synthesized through a variety of reactions. For example, the organic compound represented by General Formula (G1) can be synthesized through the following simple synthesis scheme.

For example, as shown in Synthesis Scheme (a), a halogen compound (A1) including a substituted or unsubstituted benzofuropyrimidine skeleton or benzothienopyrimidine skeleton is reacted with a condensed ring (A2) including a substituted or unsubstituted aryl group.

[Chemical Formula 24]

(a)

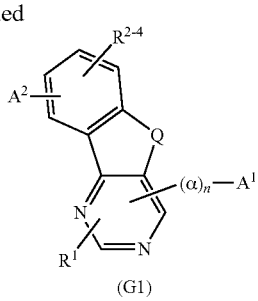

(G1)

At this time, as shown in Synthesis Scheme (b), a boronic acid compound of the condensed ring including a substituted or unsubstituted aryl group (A2) may be reacted with a dihalogen compound (B1) including a substituted or unsubstituted benzofuropyrimidine skeleton or benzothienopyrimidine skeleton to give an intermediate (D1), and then, the intermediate (D1) may be reacted with a boronic acid compound (B2) of a substituted or unsubstituted condensed ring.

[Chemical Formula 25]

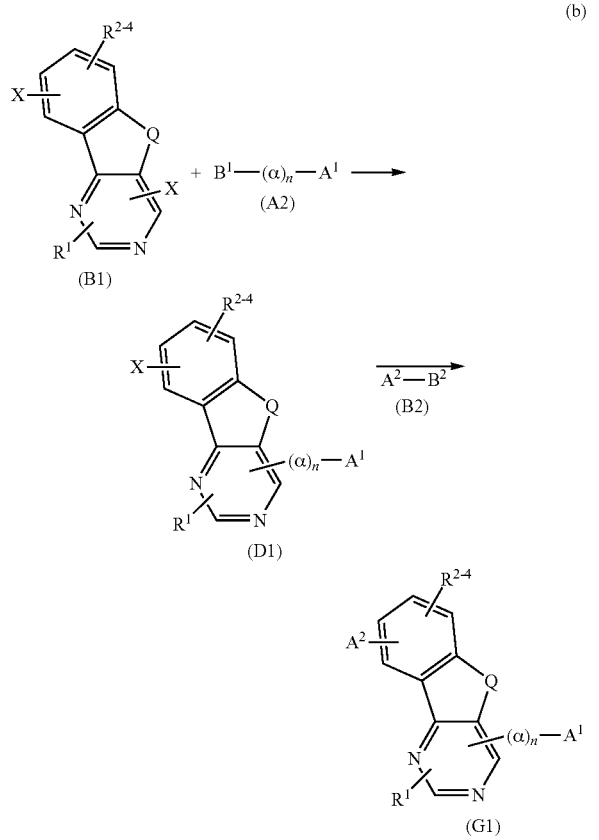

(b)

Alternatively, as shown in Synthesis Scheme (c), after an intermediate (D2) is obtained through a reaction with a halogen-substituted aryl boronic acid compound (C1) and then an intermediate (D3) is obtained through a reaction with a boronic acid compound (C2) of a substituted or unsubstituted condensed ring, the intermediate (D3) may be reacted with the boronic acid compound (B2) of a substituted or unsubstituted condensed ring. Note that each of $B^1$ to $B^4$ represents a boronic acid, a boronic ester, a cyclic-triolborate salt, or the like. As the cyclic-triolborate salt, a lithium salt, a potassium salt, or a sodium salt may be used.

[Chemical Formula 26]

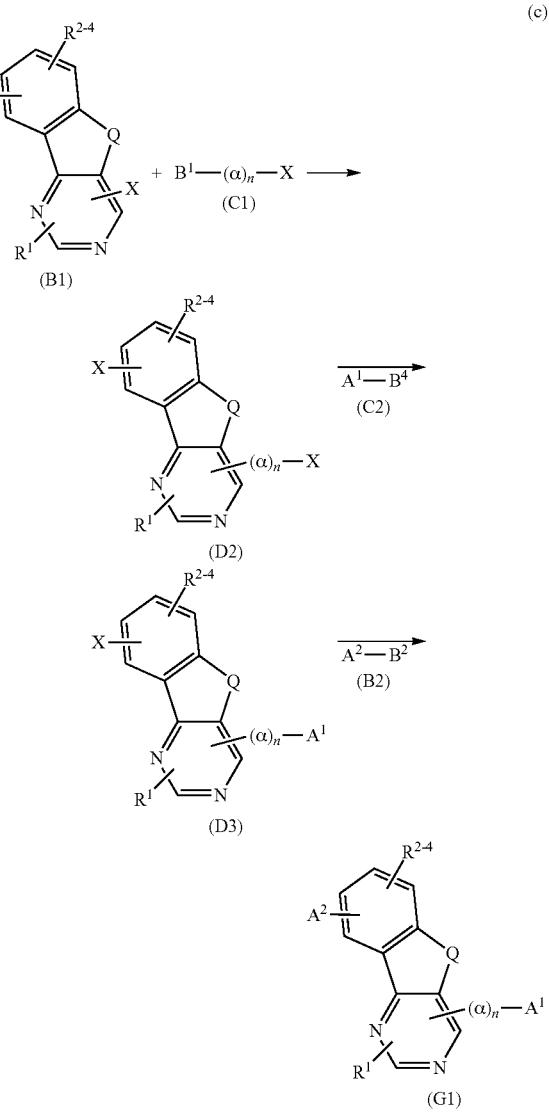

(c)

Note that in Synthesis Schemes (a), (b), and (c), X represents a halogen group or a triflate group; Q represents oxygen or sulfur; $A^1$ represents a substituted or unsubstituted aryl group having 6 to 100 total carbon atoms or a substituted or unsubstituted heteroaryl group having 6 to 100 total carbon atoms; $A^2$ represents a condensed ring; $R^1$ to $R^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; a represents a substituted or unsubstituted arylene group having 6 to 13 carbon atoms; and n represents an integer of 0 to 4.

Various kinds of the above compounds (A1), (A2), (B1), (B2), (C1), and (C2) are commercially available or can be synthesized; accordingly, various kinds of the benzofuropyrimidine derivatives or the benzothienopyrimidine derivatives represented by General Formula (G1) can be synthesized. That is, the compound of one embodiment of the present invention is characterized by having numerous variations.

In the case where Suzuki-Miyaura cross-coupling reaction using a palladium catalyst is performed in Synthesis Schemes (a), (b), and (c), preferably, X represents a halogen group or a triflate group, and the halogen is iodine, bromine, or chlorine. In the reaction, a palladium compound such as tris(dibenzylideneacetone)dipalladium(0) or palladium(II) acetate and a ligand such as di(1-adamantyl)-n-butylphosphine or 2'-(dicyclohexylphosphino)acetophenone ethylene ketal can be used. In addition, an organic base such as sodium tert-butoxide, an inorganic base such as cesium fluoride, tripotassium phosphate, or potassium carbonate, or the like can be used. Furthermore, toluene, xylene, benzene, tetrahydrofuran, mesitylene, diglyme, or the like can be used as a solvent. Reagents that can be used in the reaction are not limited thereto.

Described above is an example of the method for synthesizing the benzofuropyrimidine derivative or the benzothienopyrimidine derivative, which is a compound of one embodiment of the present invention. The present invention is not limited to this example and any other synthesis methods may be employed.

With the use of the organic compound of one embodiment of the present invention, a light-emitting element, a light-emitting device, an electronic device, or a lighting device with high emission efficiency can be obtained. In addition, a light-emitting element, a light-emitting device, an electronic device, or a lighting device with low power consumption can be obtained.

In this embodiment, embodiments of the present invention have been described. Other embodiments of the present invention are described in the other embodiments. Note that embodiments of the present invention are not limited thereto. In other words, since various embodiments of the invention are described in this embodiment and the other embodiments, embodiments of the present invention are not limited to particular embodiments.

The structures described in this embodiment can be combined with any of the structures described in the other embodiments as appropriate.

Embodiment 2

In this embodiment, a light-emitting element including any of the organic compounds described in Embodiment 1 is described with reference to FIGS. 1A to 1E.

<<Basic Structure of Light-Emitting Element>>

First, a basic structure of a light-emitting element will be described. FIG. 1A illustrates a light-emitting element including, between a pair of electrodes, an EL layer having a light-emitting layer. Specifically, an EL layer 103 is provided between a first electrode 101 and a second electrode 102.

Figure 1B:
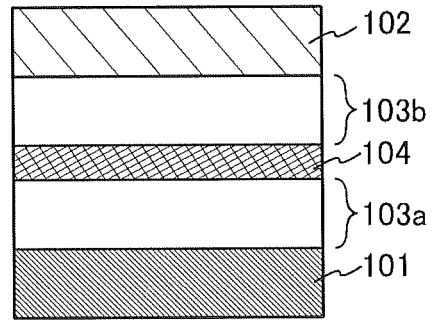

FIG. 1B illustrates a light-emitting element that has a stacked-layer structure (tandem structure) in which a plurality of EL layers (two EL layers 103a and 103b in FIG. 1B) are provided between a pair of electrodes and a charge-generation layer 104 is provided between the EL layers. With the use of such a tandem light-emitting element, a light-emitting device which can be driven at low voltage with low power consumption can be obtained.

The charge-generation layer 104 has a function of injecting electrons into one of the EL layers (103a or 103b) and injecting holes into the other of the EL layers (103b or 103a) when voltage is applied between the first electrode 101 and the second electrode 102. Thus, when voltage is applied in FIG. 1B such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a property of transmitting visible light (specifically, the charge-generation layer 104 has a visible light transmittance of 40% or more). The charge-generation layer 104 functions even when it has lower conductivity than the first electrode 101 or the second electrode 102.

Figure 1C:
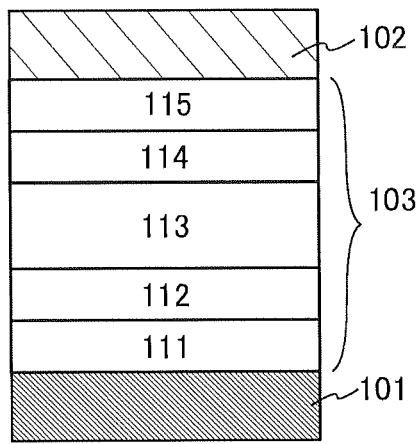

FIG. 1C illustrates a stacked-layer structure of the EL layer 103 in the light-emitting element of one embodiment of the present invention. In this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked in this order over the first electrode 101. Even in the case where a plurality of EL layers are provided as in the tandem structure illustrated in FIG. 1B, the layers in each EL layer are sequentially stacked from the anode side as described above. When the first electrode 101 is a cathode and the second electrode 102 is an anode, the stacking order is reversed.

The light-emitting layer 113 included in the EL layers (103, 103a, and 103b) contains an appropriate combination of a light-emitting substance and a plurality of substances, so that fluorescence or phosphorescence of a desired emission color can be obtained. The light-emitting layer 113 may have a stacked-layer structure having different emission colors. In that case, the light-emitting substance and other substances are different between the stacked light-emitting layers. Alternatively, the plurality of EL layers (103a and 103b) in FIG. 1B may exhibit their respective emission colors. Also in that case, the light-emitting substance and other substances are different between the light-emitting layers.

The light-emitting element of one embodiment of the present invention can have a micro optical resonator (microcavity) structure when, for example, the first electrode 101 is a reflective electrode and the second electrode 102 is a transflective electrode in FIG. 1C. Thus, light emission from the light-emitting layer 113 in the EL layer 103 can be resonated between the electrodes and light emission obtained through the second electrode 102 can be intensified.

Note that when the first electrode 101 of the light-emitting element is a reflective electrode in which a reflective conductive material and a light-transmitting conductive material (transparent conductive film) are stacked, optical adjustment can be performed by controlling the thickness of the transparent conductive film. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number).

Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer emitting the desired light is, to be exact, the optical path length between the reflective region in the first electrode 101 and the light-emitting region in the light-emitting layer emitting the desired light. However, it is difficult to precisely determine the reflective region in the first electrode 101 and the light-emitting region in the light-emitting layer emitting the desired light; thus, it is assumed that the above effect can be sufficiently obtained wherever the reflective region and the light-emitting region may be set in the first electrode 101 and the light-emitting layer emitting the desired light.

The light-emitting element in FIG. 1C has a microcavity structure, so that light (monochromatic light) with different wavelengths can be extracted even if the same EL layer is used. Thus, separate coloring for obtaining a plurality of emission colors (e.g., R, G, and B) is not necessary. Therefore, high resolution can be easily achieved. Note that a combination with coloring layers (color filters) is also possible. Furthermore, emission intensity of light with a specific wavelength in the front direction can be increased, whereby power consumption can be reduced.

Figure 1D:
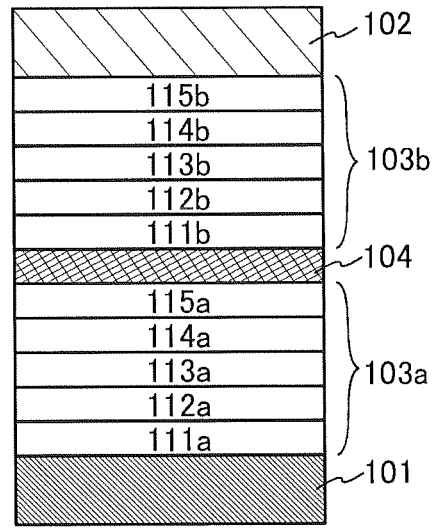
Figure 1E:
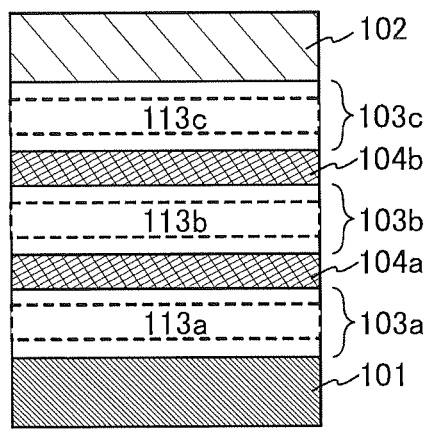

A light-emitting element illustrated in FIG. 1E is an example of the light-emitting element with the tandem structure illustrated in FIG. 1B, and includes three EL layers (103a, 103b, and 103c) stacked with charge-generation layers (104a and 104b) positioned therebetween, as illustrated in the figure. The three EL layers (103a, 103b, and 103c) include respective light-emitting layers (113a, 113b, and 113c) and the emission colors of the light-emitting layers can be selected freely. For example, the light-emitting layer 113a can be blue, the light-emitting layer 113b can be red, green, or yellow, and the light-emitting layer 113c can be blue. For another example, the light-emitting layer 113a can be red, the light-emitting layer 113b can be blue, green, or yellow, and the light-emitting layer 113c can be red.

In the light-emitting element of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, and preferably higher than or equal to 40% and lower than or equal to 70%. These electrodes preferably have a resistivity of $1\times10^{-2}$ Ωcm or less.

Furthermore, when one of the first electrode 101 and the second electrode 102 is a reflective electrode in the light-emitting element of one embodiment of the present invention, the visible light reflectance of the reflective electrode is higher than or equal to 40% and lower than or equal to 100%, and preferably higher than or equal to 70% and lower than or equal to 100%. This electrode preferably has a resistivity of $1\times10^{-2}$ Ωcm or less.

<<Specific Structure and Fabrication Method of Light-Emitting Element>>

Specific structures and fabrication methods of light-emitting elements of embodiments of the present invention will be described with reference to FIGS. 1A to 1E. Here, a light-emitting element having the tandem structure in FIG. 1B and a microcavity structure will be described with reference to FIG. 1D. In the light-emitting element in FIG. 1D having a microcavity structure, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103b, with the use of a material selected as described above. For fabrication of these electrodes, a sputtering method or a vacuum evaporation method can be used.

<First Electrode and Second Electrode>

As materials used for the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting element in FIG. 1D, when the first electrode 101 is an anode, a hole-injection layer 111a and a hole-transport layer 112a of the EL layer 103a are sequentially stacked over the first electrode 101 by a vacuum evaporation method. After the EL layer 103a and the charge-generation layer 104 are formed, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) inject holes from the first electrode 101 that is an anode and the charge-generation layer (104) to the EL layers (103, 103a, and 103b) and each contain a material with a high hole-injection property.

As examples of the material with a high hole-injection property, transition metal oxides such as molybdenum oxide, vanadium oxide, ruthenium oxide, tungsten oxide, and manganese oxide can be given. Alternatively, it is possible to use any of the following materials:

phthalocyanine-based compounds such as phthalocyanine (abbreviation: H$_2$Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N-bis 4-[bis(3-methylphenyl)amino]phenyl-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); and the like.

Alternatively, as the material with a high hole-injection property, a composite material containing a hole-transport material and an acceptor material (an electron-accepting material) can also be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed to have a single-layer structure using a composite material containing a hole-transport material and an acceptor material (electron-accepting material), or a stacked-layer structure in which a layer including a hole-transport material and a layer including an acceptor material (electron-accepting material) are stacked.

The hole-transport layers (112, 112a, and 112b) transport the holes, which are injected from the first electrode 101 and the charge-generation layer (104) by the hole-injection layers (111, 111a, and 111b), to the light-emitting layers (113, 113a, and 113b). Note that the hole-transport layers (112, 112a, and 112b) each contain a hole-transport material. It is particularly preferable that the HOMO level of the hole-transport material included in the hole-transport layers (112, 112a, and 112b) be the same as or close to that of the hole-injection layers (111, 111a, and 111b).

Examples of the acceptor material used for the hole-injection layers (111, 111a, and 111b) include an oxide of a metal belonging to any of Groups 4 to 8 of the periodic table. Specifically, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and the like can be used. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred. Specific examples include α,α', α"-1,2,3-cyclopropanetriylidenetris[4-cyano-2,3,5,6-tetrafluorobenzeneacetonitrile], α, α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]

The hole-transport materials used for the hole-injection layers (111, 111a, and 111b) and the hole-transport layers (112, 112a, and 112b) are preferably substances with a hole mobility of greater than or equal to $10^{-6}$ cm$^2$/Vs. Note that other substances may be used as long as the substances have a hole-transport property higher than an electron-transport property.

Preferred hole-transport materials are π-electron rich heteroaromatic compounds (e.g., carbazole derivatives and indole derivatives) and aromatic amine compounds, examples of which include compounds having an aromatic amine skeleton, such as 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yephenyl]fluoren-2-amine (abbreviation: PCBAF), N-phenyl-N-[4-(9-phenyl-9H-carbazol-3-yephenyl]spiro-9,9'-bifluoren-2-amine (abbreviation: PCBASF), 4,4',4"-tris(carbazol-9-yl)triphenylamine (abbreviation: TCTA), 4,4',4"-tris(N,N-diphenylamino)triphenylamine (abbreviation: TDATA), and 4,4',4"-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenyl-carbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N-bis(4-butylphenyl)-N,N'-bis(phenyl)benzidine] (abbreviation: Poly-TPD) can also be used.

Note that the hole-transport material is not limited to the above examples and may be one of or a combination of various known materials when used for the hole-injection layers (111, 111a, and 111b) and the hole-transport layers (112, 112a, and 112b). Note that the hole-transport layers (112, 112a, and 112b) may each be formed of a plurality of layers. That is, for example, the hole-transport layers may each have a stacked-layer structure of a first hole-transport layer and a second hole-transport layer.

In the light-emitting element in FIG. 1D, the light-emitting layer 113a is formed over the hole-transport layer 112a of the EL layer 103a by a vacuum evaporation method. After the EL layer 103a and the charge-generation layer 104 are formed, the light-emitting layer 113b is formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance whose emission color is blue, violet, bluish violet, green, yellowish green, yellow, orange, red, or the like is appropriately used. When the plurality of light-emitting layers (113a, 113b, and 113c) are formed using different light-emitting substances, different emission colors can be exhibited (for example, complementary emission colors are combined to achieve white light emission). Furthermore, a stacked-layer structure in which one light-emitting layer contains two or more kinds of light-emitting substances may be employed.

The light-emitting layers (113, 113a, 113b, and 113c) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

As the light-emitting substance that can be used for the light-emitting layers (113, 113a, 113b, and 113c), a light-emitting substance that converts singlet excitation energy into light emission in the visible light range or a light-emitting substance that converts triplet excitation energy into light emission in the visible light range can be used.

Examples of other light-emitting substances are given below.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N-bis[4-(9-phenyl-9H-fluoren-9-yl)phenyl]pyrene-1,6-diamine (abbreviation: 1,6FLPAPm), N,N'-bis (dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-diphenylstilbene-4,4'-diamine (abbreviation: YGA2S), 4-(9H-carbazol-9-yl)-4?-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,N'-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl) triphenylamine (abbreviation: PCBAPBA), perylene, 2,5,8,11-tetra(tert-butyl)perylene (abbreviation: TBP), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of a light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is appropriately selected according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f] phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,C$^2$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)); and the like can be given.

As examples of a phosphorescent material which emits green or yellow light and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato) iridium(III) (abbreviation: [Ir(mppm)$_2$(acac)]), (acetylacetonato)bis(6-tert-butyl-4-phenylpyrimidinato) iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac))]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$iridium(III) acetylacetonate (abbreviation: [Ir(pq)$_2$(acac)]), [2-(4-phenyl-2-pyridinyl-κN)phenyl-κC]bis[2-(2-pyridinyl-κN)phenyl-κC] iridium(III) (abbreviation: Ir(ppy)$_2$(4dppy)), and bis[2-(2-pyridinyl-1N)phenyl-KC][2-(4-methyl-5-phenyl-2-pyridinyl-κN)phenyl-κC]; organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline) terbium(III) (abbreviation: [Tb(acac)$_3$(Phen)]) can be given.

As examples of a phosphorescent material which emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N,C$^2$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir(piq)$_3$]), bis(1-phenylisoquinolinato-N,C$^{2'}$)iridium(III) acetylacetonate (abbreviation: [Ir(piq)$_2$(acac)]), and bis[4,6-dimethyl-2-(2-quinolinyl-κN)phenyl-κC](2,4-pentadionato-κ$^2$O,O')iridium(III); platinum complexes such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As the organic compounds (the host material and the assist material) used in the light-emitting layers (113, 113a, 113b, and 113c), one or more kinds of substances having a larger energy gap than the light-emitting substance (the guest material) are used. In the case where a plurality of organic compounds are used for the light-emitting layers (113, 113a, 113b, and 113c), it is preferable to use compounds that form an exciplex in combination with a light-emitting substance. With such a structure, light emission can be obtained by exciplex-triplet energy transfer (ExTET), which is energy transfer from an exciplex to a light-emitting substance. In that case, although any of various organic compounds can be combined appropriately to be used, to form an exciplex efficiently, it is particularly preferable to combine a compound that easily accepts holes (hole-transport material) and a compound that easily accepts electrons (electron-transport material). The organic compound of one embodiment of the present invention has a low LUMO level and thus is suitable for the compound that easily accepts electrons.

When the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specific examples thereof include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

More specifically, any of the following hole-transport materials and electron-transport materials can be used as the host material, for example.

Examples of the host material having a high hole-transport property include aromatic amine compounds such as N,N'-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Carbazole derivatives such as 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1) are also given. Other examples of the carbazole derivative include 4,4'-di(N-carbazolyl)biphenyl (abbreviation: CBP), 1,3,5-tris[4-(N-carbazolyl)phenyl]benzene (abbreviation: TCPB), and 1,4-bis[4-(N-carbazolyl)phenyl]-2,3,5,6-tetraphenylbenzene.

Examples of the host material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris[N-(1-naphthyl)-N-phenylamino]triphenylamine (abbreviation: 1-TNATA), 4,4',4''-tris(N,N-diphenylamino)triphenylamine (abbreviation: TDATA), 4,4',4''-tris[N-(3-methylphenyl)-N-phenylamino]triphenylamine (abbreviation: m-MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N-bis(9-phenylcarbazol-3-yl)-N,N-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyephenylaniline (abbreviation: YGA1BP), and N,N'-bis[4-(carbazol-9-yl)phenyl]-N,N-diphenyl-9,9-dimethylfluorene-2,7-diamine (abbreviation: YGA2F). Other examples are carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II).

Examples of the host material having a high electron-transport property include a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), or bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Other than such metal complexes, any of the following can be used: oxadiazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-4-phenyl-5-(4-tert-butylphenyl)-1,2,4-triazole (abbreviation: TAZ); a compound having an imidazole skeleton (in particular, a benzimidazole derivative) such as 2,2',2''-(1,3,5-benzenetriyl)tris(1-phenyl-1H-benzimidazole) (abbreviation: TPBI) or 2-[3-(dibenzothiophen-4-yl)phenyl]-1-phenyl-1H-benzimidazole (abbreviation: mDBTBIm-II); a compound having an oxazole skeleton (in particular, a benzoxazole derivative) such as 4,4'-bis(5-methylbenzoxazol-2-yl)stilbene (abbreviation: BzOs); a phenanthroline derivative such as bathophenanthroline (abbreviation: BPhen), bathocuproine (abbreviation: BCP), and 2,9-bis(naphthalen-2-yl)-4,7-diphenyl-1,10-phenanthroline (abbreviation: NBPhen); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

Examples of the host material include condensed polycyclic aromatic compounds such as anthracene derivatives, phenanthrene derivatives, pyrene derivatives, chrysene derivatives, and dibenzo[g,p]chrysene derivatives. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 2PCAPA, 6,12-dimethoxy-5,11-diphenylchrysene, DBC1,9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3).

In the case where a plurality of organic compounds are used for the light-emitting layers (113, 113a, 113b, and 113c), it is possible to use two compounds that form an exciplex (a first compound and a second compound) combined with an organometallic complex. In that case, although any of various organic compounds can be combined appropriately to be used, to form an exciplex efficiently, it is particularly preferable to combine a compound that easily accepts holes (a hole-transport material) and a compound that easily accepts electrons (an electron-transport material). As the hole-transport material and the electron-transport material, specifically, any of the materials described in this embodiment can be used. With the above structure, high efficiency, low voltage, and a long lifetime can be achieved at the same time.

The TADF material is a material that can up-convert a triplet excited state into a singlet excited state (i.e., reverse intersystem crossing is possible) using a little thermal energy and efficiently exhibits light emission (fluorescence) from the singlet excited state. The TADF is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio 1)), and an octaethylporphyrin-platinum chloride complex (abbreviation: $PtCl_2OEP$).

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can be combined with another organic compound.

In the light-emitting element in FIG. 1D, the electron-transport layer 114a is formed over the light-emitting layer 113a of the EL layer 103a by a vacuum evaporation method. After the EL layer 103a and the charge-generation layer 104 are formed, the electron-transport layer 114b is formed over the light-emitting layer 113b of the EL layer 103b by a vacuum evaporation method.

<Electron-Transport Layer>

The electron-transport layers (114, 114a, and 114b) transport the electrons, which are injected from the second electrode 102 and the charge-generation layer (104) by the electron-injection layers (115, 115a, and 115b), to the light-emitting layers (113, 113a, and 113b). Note that the electron-transport layers (114, 114a, and 114b) each contain an electron-transport material. It is preferable that the electron-transport materials included in the electron-transport layers (114, 114a, and 114b) be substances with an electron mobility of higher than or equal to $1 \times 10^{-6}$ cm$^2$/Vs. Note that other substances may also be used as long as the substances have an electron-transport property higher than a hole-transport property.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as $Alq_3$, tris(4-methyl-8-quinolinolato)aluminum(III) (abbreviation: $Almq_3$), bis(10-hydroxybenzo[h]quinolinato)beryllium(II) (abbreviation: $BeBq_2$), BAlq, bis[2-(2-hydroxyphenyl)benzoxazolato]zinc(II) (abbreviation: $Zn(BOX)_2$), and bis[2-(2-hydroxyphenyl)benzothiazolato]zinc(II) (abbreviation: $Zn(BTZ)_2$), heteroaromatic compounds such as 2-(4-biphenylyl)-5-(4-tert-butylphenyl)-1,3,4-oxadiazole (abbreviation: PBD), OXD-7,3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs), and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDB q-II).

Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

Each of the electron-transport layers (114, 114a, and 114b) is not limited to a single layer, but may be a stack of two or more layers each containing any of the above substances.

In the light-emitting element in FIG. 1D, the electron-injection layer 115a is formed over the electron-transport layer 114a of the EL layer 103a by a vacuum evaporation method. Subsequently, the EL layer 103a and the charge-generation layer 104 are formed, the components up to the electron-transport layer 114b of the EL layer 103b are formed, and then the electron-injection layer 115b is formed thereover by a vacuum evaporation method.

<Electron-Injection Layer>

The electron-injection layers (115, 115a, and 115b) each contain a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride ($CaF_2$), or lithium oxide ($LiO_x$). A rare earth metal compound like erbium fluoride ($ErF_3$) can also be used. Electride may also be used for the electron-injection layers (115, 115a, and 115b). Examples of the electride include a substance in which electrons are added at high concentration to calcium oxide-aluminum oxide. Any of the substances for forming the electron-transport layers (114, 114a, and 114b), which are given above, can also be used.

A composite material in which an organic compound and an electron donor (donor) are mixed may also be used for the electron-injection layers (115, 115a, and 115b). Such a composite material is excellent in an electron-injection property and an electron-transport property because electrons are generated in the organic compound by the electron donor. The organic compound here is preferably a material excellent in transporting the generated electrons; specifically, for example, the electron-transport materials for forming the electron-transport layers (114, 114a, and 114b) (e.g., a metal complex or a heteroaromatic compound) can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be given. Furthermore, an alkali metal oxide and an alkaline earth metal oxide are preferable, and a lithium oxide, a calcium oxide, a barium oxide, and the like can be given. Alternatively, a Lewis base such as magnesium oxide can be used. Further alternatively, an organic compound such as tetrathiafulvalene (abbreviation: TTF) can be used.

In the case where light obtained from the light-emitting layer 113b is amplified, for example, the optical path length between the second electrode 102 and the light-emitting layer 113b is preferably less than one fourth of the wavelength λ of light emitted from the light-emitting layer 113b. In that case, the optical path length can be adjusted by changing the thickness of the electron-transport layer 114b or the electron-injection layer 115b.

<Charge-Generation Layer>

The charge-generation layer 104 has a function of injecting electrons into the EL layer 103a and injecting holes into the EL layer 103b when a voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 by using any of the above materials can suppress an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: $F_4$-TCNQ), chloranil, and the like. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, or the like is used.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103c in FIG. 1E has a structure similar to those of the above-described EL layers (103, 103a, and 103b). In addition, the charge-generation layers 104a and 104b each have a structure similar to that of the above-described charge-generation layer 104.

<Substrate>

The light-emitting element described in this embodiment can be formed over any of a variety of substrates. Note that the type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as acrylic; polypropylene; polyester; polyvinyl fluoride; polyvinyl chloride; polyamide; polyimide; aramid; epoxy; an inorganic vapor deposition film; and paper.

For fabrication of the light-emitting element in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), the electron-injection layers (115, 115a, and 115b)) included in the EL layers and the charge-generation layers (104, 104a, and 104b) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Note that materials that can be used for the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) that are included in the EL layers (103, 103a, and 103b) and the charge-generation layers (104, 104a, and 104b) in the light-emitting element described in this embodiment are not limited to the above materials, and other materials can be used in combination as long as the functions of the layers are fulfilled. For example, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. The quantum dot may be a colloidal quantum dot, an alloyed quantum dot, a core-shell quantum dot, a core quantum dot, or the like.

The structures described in this embodiment can be combined with any of the structures described in the other embodiments as appropriate.

Embodiment 3

Figure 2A:
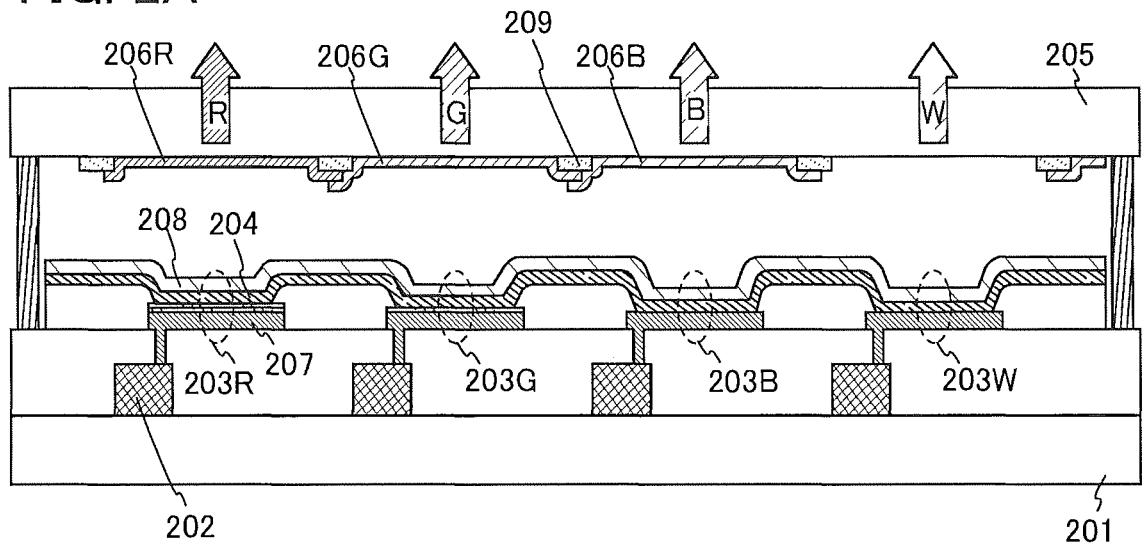
FIGS. 2A to 2C illustrate a light-emitting device.

In this embodiment, a light-emitting device of one embodiment of the present invention is described. Note that a light-emitting device illustrated in FIG. 2A is an active-matrix light-emitting device in which transistors (FETs) 202 are electrically connected to light-emitting elements (203R, 203G, 203B, and 203W) over a first substrate 201. The light-emitting elements (203R, 203G, 203B, and 203W) include a common EL layer 204 and each have a microcavity structure in which the optical path length between electrodes is adjusted depending on the emission color of the light-emitting element. The light-emitting device is a top-emission light-emitting device in which light is emitted from the EL layer 204 through color filters (206R, 206G, and 206B) formed on a second substrate 205.

The light-emitting device illustrated in FIG. 2A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 2B:
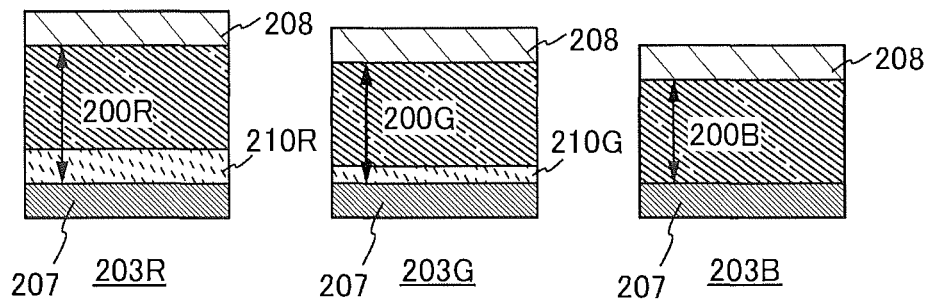

In the case where the light-emitting element 203R functions as a red light-emitting element, the light-emitting element 203G functions as a green light-emitting element, the light-emitting element 203B functions as a blue light-emitting element, and the light-emitting element 203W functions as a white light-emitting element in FIG. 2A, for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2B. Note that optical adjustment can be performed in such a manner that a conductive layer 210R is stacked over the first electrode 207 in the light-emitting element 203R and a conductive layer 210G is stacked over the first electrode 207 in the light-emitting element 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting element 203R, whereby red light emission can be obtained from the light-emitting element 203R. Furthermore, the color filter 206G that transmits only light in the green wavelength range is provided in a position overlapping with the light-emitting element 203G, whereby green light emission can be obtained from the light-emitting element 203G. Moreover, the color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
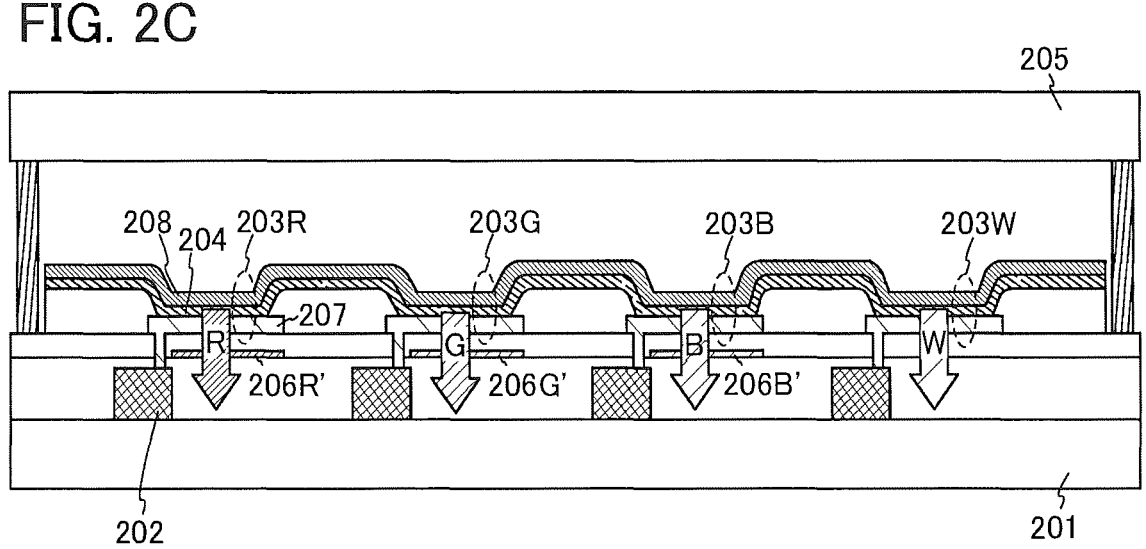

Although the light-emitting device in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting device, the first electrode 207 is formed as a transflective electrode and the second electrode 208 is formed as a reflective electrode. As the first substrate 201, a substrate having at least a light-transmitting property is used. As illustrated in FIG. 2C, color filters (206W, 206G', and 206B') are provided so as to be closer to the first substrate 201 than the light-emitting elements (203R, 203G, and 203B) are.

In FIG. 2A, the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting elements. In that case, a color filter needs to be appropriately selected depending on the emission color of the light-emitting element.

With the above structure, a light-emitting device including light-emitting elements that exhibit a plurality of emission colors can be fabricated.

Note that the structures described in this embodiment can be combined with any of the structures described in the other embodiments as appropriate.

Embodiment 4

In this embodiment, a light-emitting device of one embodiment of the present invention is described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is one embodiment of the present invention. Note that any of the light-emitting elements described in other embodiments can be used in the light-emitting device described in this embodiment.

In this embodiment, an active-matrix light-emitting device will be described with reference to FIGS. 3A and 3B.

Figure 3A:
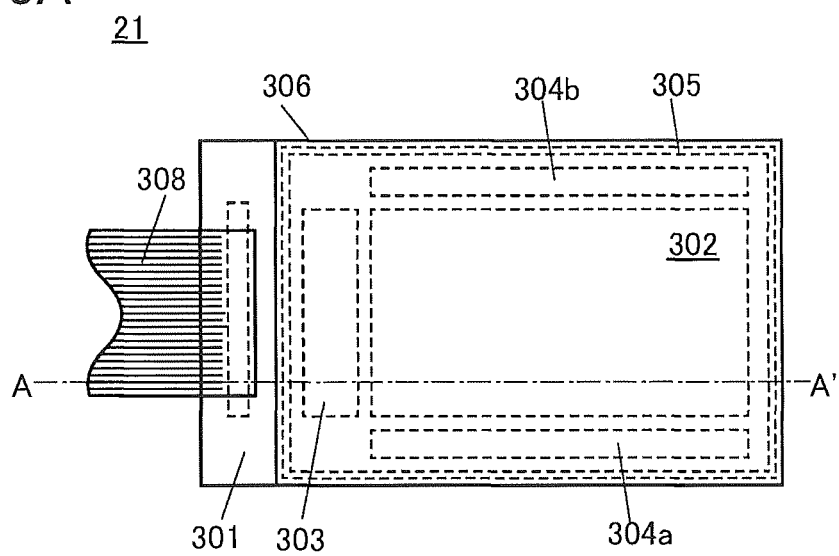
FIGS. 3A and 3B illustrate a light-emitting device.
Figure 3B:
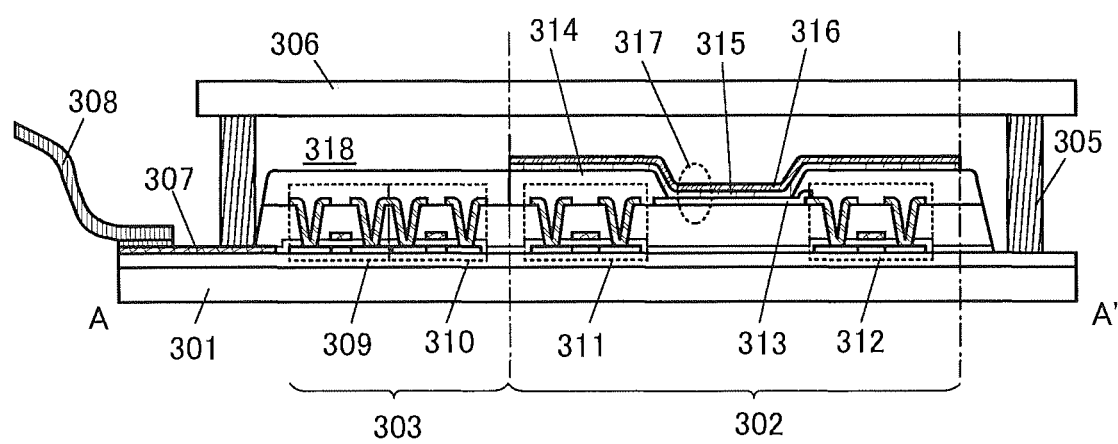

FIG. 3A is a top view illustrating the light-emitting device, and FIG. 3B is a cross-sectional view taken along chain line A-A' in FIG. 3A. The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

FIG. 3B illustrates a cross-sectional structure of the light-emitting device.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting element 317 described in this embodiment. Although not illustrated, the second electrode 316 is electrically connected to the FPC 308 that is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of displaying a full-color image can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of some of the above colors are used in combination with the light-emitting elements that emit light of three kinds of colors (R, G, and B), whereby effects such as an improvement in color purity and a reduction in power consumption can be achieved. Alternatively, a light-emitting device which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, acrylic, or the like can be used. In the case where glass frit is used for the sealant, the first substrate 301 and the second substrate 306 are preferably glass substrates in terms of adhesion.

Accordingly, the active-matrix light-emitting device can be obtained.

In the case where the active-matrix light-emitting device is provided over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be combined with any of the structures described in the other embodiments as appropriate.

Embodiment 5

In this embodiment, examples of a variety of electronic devices and an automobile manufactured using the light-emitting device of one embodiment of the present invention or a display device including the light-emitting element of one embodiment of the present invention are described.

Electronic devices illustrated in FIGS. 4A to 4E can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

Figure 4A:
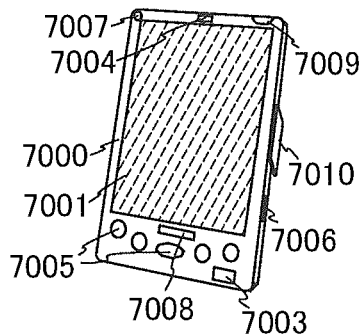
FIGS. 4A to 4G illustrate electronic devices.

FIG. 4A illustrates a mobile computer that can include a switch 7009, an infrared port 7010, and the like in addition to the above components.

Figure 4B:
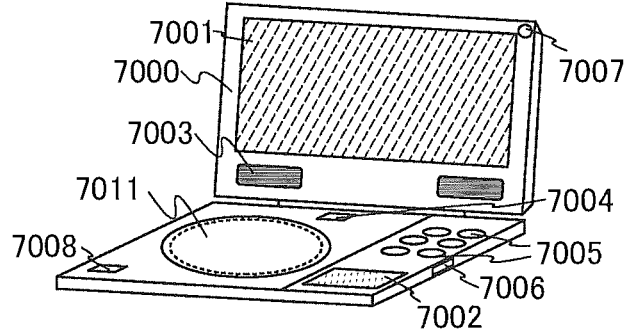

FIG. 4B illustrates a portable image reproducing device (e.g., a DVD player) that is provided with a recording medium and can include a second display portion 7002, a recording medium reading portion 7011, and the like in addition to the above components.

Figure 4C:
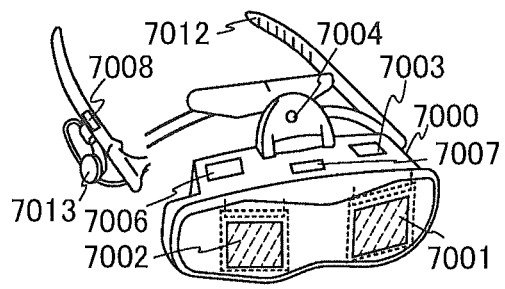

FIG. 4C illustrates a goggle-type display that can include the second display portion 7002, a support 7012, an earphone 7013, and the like in addition to the above components.

Figure 4D:
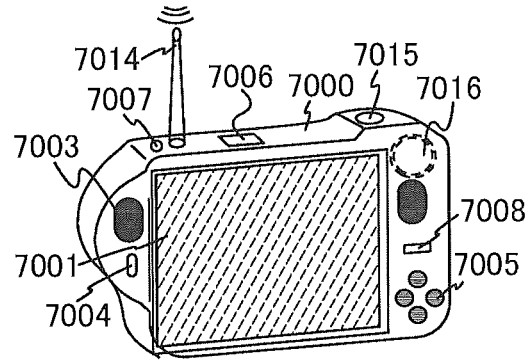

FIG. 4D illustrates a digital camera that has a television reception function and can include an antenna 7014, a shutter button 7015, an image receiving portion 7016, and the like in addition to the above components.

Figure 4E:
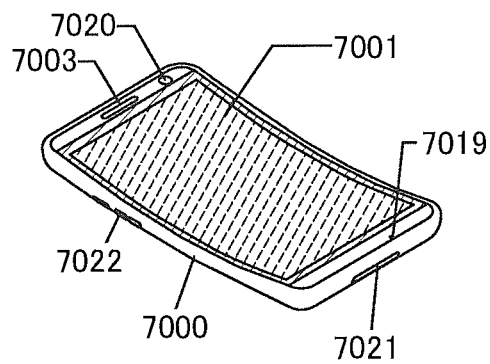

FIG. 4E illustrates a cellular phone (including a smartphone) and can include the display portion 7001, a microphone 7019, the speaker 7003, a camera 7020, an external connection portion 7021, an operation button 7022, and the like in the housing 7000.

Figure 4F:
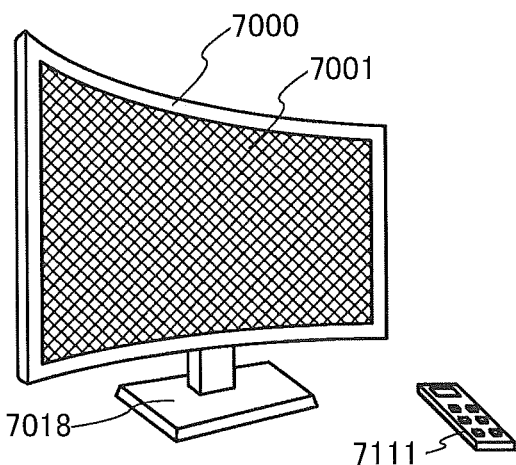

FIG. 4F illustrates a large-size television set (also referred to as TV or a television receiver) and can include the housing 7000, the display portion 7001, and the like. In addition, here, the housing 7000 is supported by a stand 7018. The television set can be operated with a separate remote controller 7111 or the like. The display portion 7001 may include a touch sensor. The television set can be operated by touching the display portion 7001 with a finger or the like. The remote controller 7111 may be provided with a display portion for displaying information output from the remote controller 7111. With operation keys or a touch panel of the remote controller 7111, channels and volume can be controlled and images displayed on the display portion 7001 can be controlled.

The electronic devices illustrated in FIGS. 4A to 4F can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like. Furthermore, the electronic device including a plurality of display portions can have a function of displaying image data mainly on one display portion while displaying text data on another display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that can be provided for the electronic devices illustrated in FIGS. 4A to 4F are not limited to those described above, and the electronic devices can have a variety of functions.

Figure 4G:
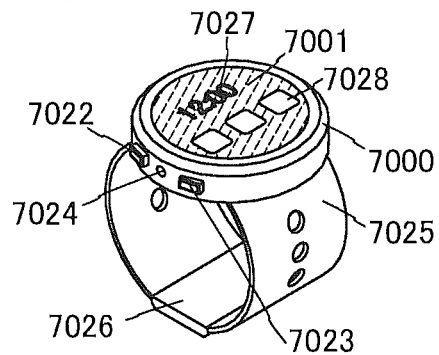

FIG. 4G illustrates a smart watch, which includes the housing 7000, the display portion 7001, operation buttons 7022 and 7023, a connection terminal 7024, a band 7025, a clasp 7026, and the like.

The display portion 7001 mounted in the housing 7000 serving as a bezel includes a non-rectangular display region. The display portion 7001 can display an icon 7027 indicating time, another icon 7028, and the like. The display portion 7001 may be a touch panel (an input/output device) including a touch sensor (an input device).

The smart watch illustrated in FIG. 4G can have a variety of functions, such as a function of displaying a variety of information (e.g., a still image, a moving image, and a text image) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like.

The housing 7000 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like.

Note that the light-emitting device of one embodiment of the present invention or the display device including the light-emitting element of one embodiment of the present invention can be used in the display portion of each electronic device described in this embodiment, so that a long lifetime electronic device can be obtained.

Figure 5A:
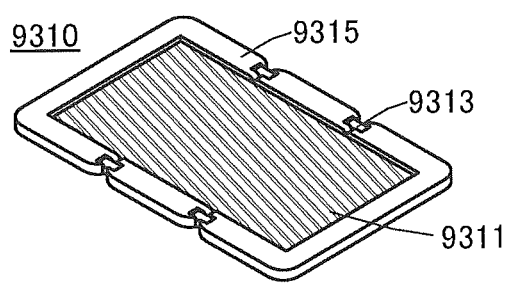
FIGS. 5A to 5C illustrate an electronic device.
Figure 5B:
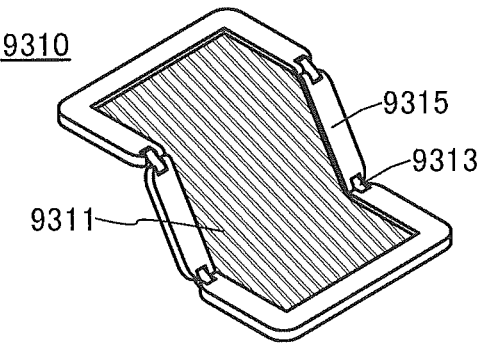
Figure 5C:
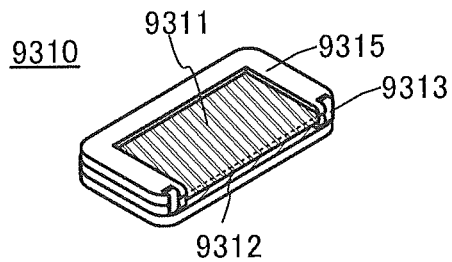

Another electronic device including the light-emitting device is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. In addition, a long lifetime electronic device can be obtained. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
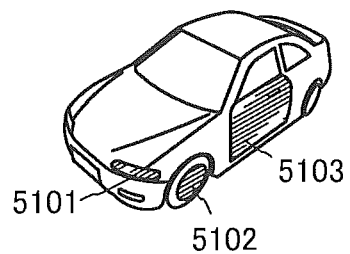
FIGS. 6A and 6B illustrate an automobile.
Figure 6B:
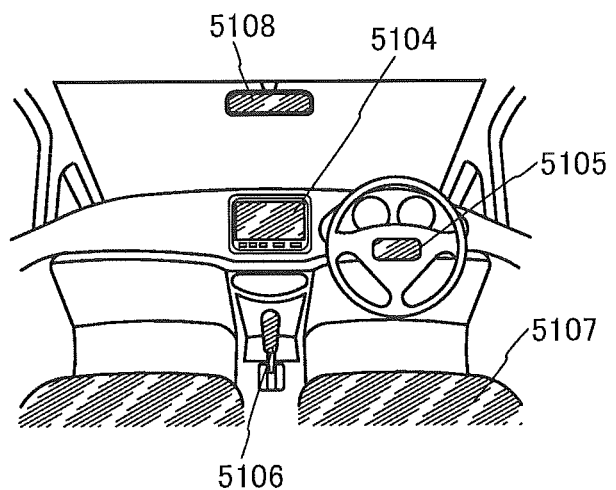

FIGS. 6A and 6B illustrate an automobile including the light-emitting device. The light-emitting device can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting device can also be included in a display portion 5104, a steering wheel 5105, a gear lever 5106, a seat 5107, an inner rearview mirror 5108, or the like on the inner side of the automobile which is illustrated in FIG. 6B, or in a part of a glass window.

In the above manner, the electronic devices and automobiles can be obtained using the light-emitting device or the display device of one embodiment of the present invention. In that case, a long lifetime electronic device can be obtained. Note that the light-emitting device or the display device can be used for electronic devices and automobiles in a variety of fields without being limited to those described in this embodiment.

Note that the structures described in this embodiment can be combined with any of the structures described in the other embodiments as appropriate.

Embodiment 6

In this embodiment, a structure of a lighting device fabricated using the light-emitting device of one embodiment of the present invention or the light-emitting element which is a part of the light-emitting device is described with reference to FIGS. 7A to 7D.

Figure 7A:
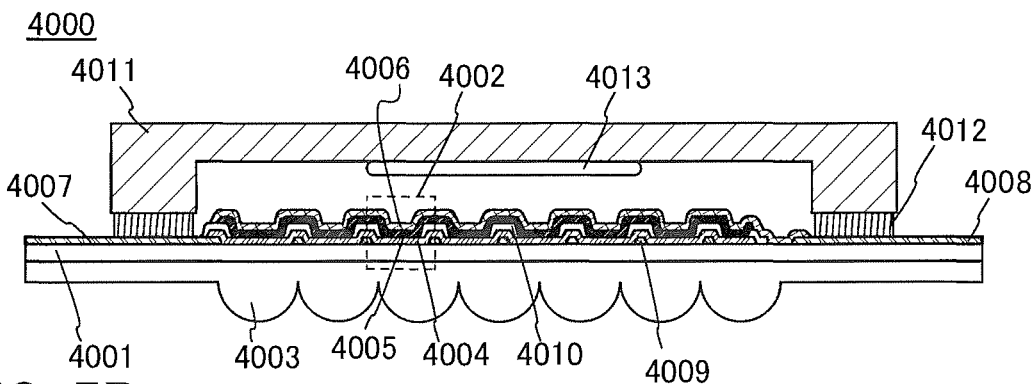
FIGS. 7A to 7D illustrate lighting devices.
Figure 7B:
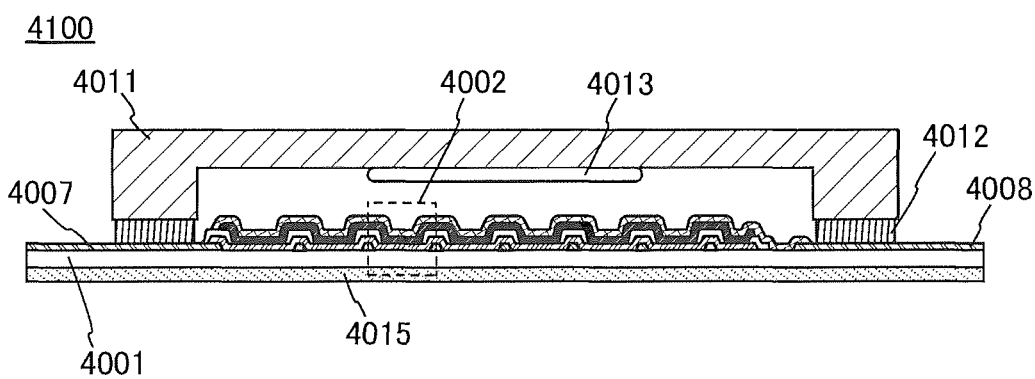
Figure 7C:
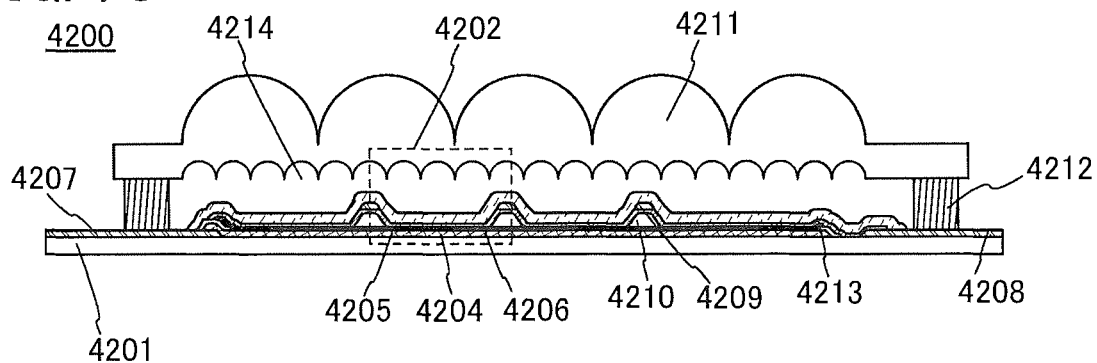
Figure 7D:
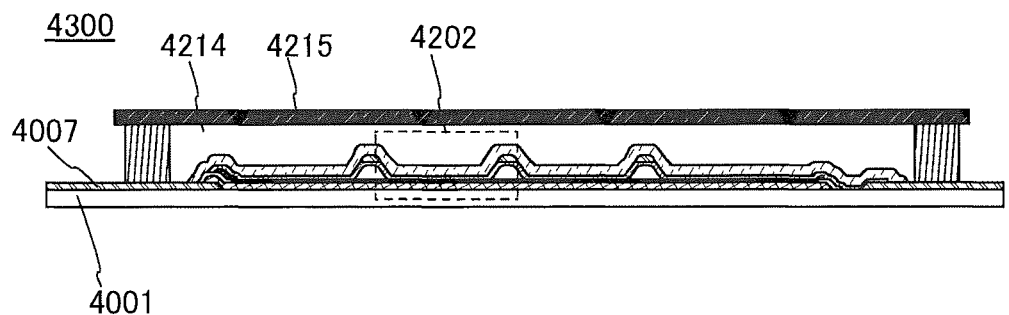

FIGS. 7A to 7D are examples of cross-sectional views of lighting devices. FIGS. 7A and 7B illustrate bottom-emission lighting devices in which light is extracted from the substrate side, and FIGS. 7C and 7D illustrate top-emission lighting devices in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 7B.

A lighting device 4200 illustrated in FIG. 7C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 7D.

Note that with the use of the light-emitting device of one embodiment of the present invention or the light-emitting element which is a part of the light-emitting device as described in this embodiment, a lighting device having desired chromaticity can be provided.

Note that the structures described in this embodiment can be combined with any of the structures described in the other embodiments as appropriate.

Embodiment 7

Figure 8:
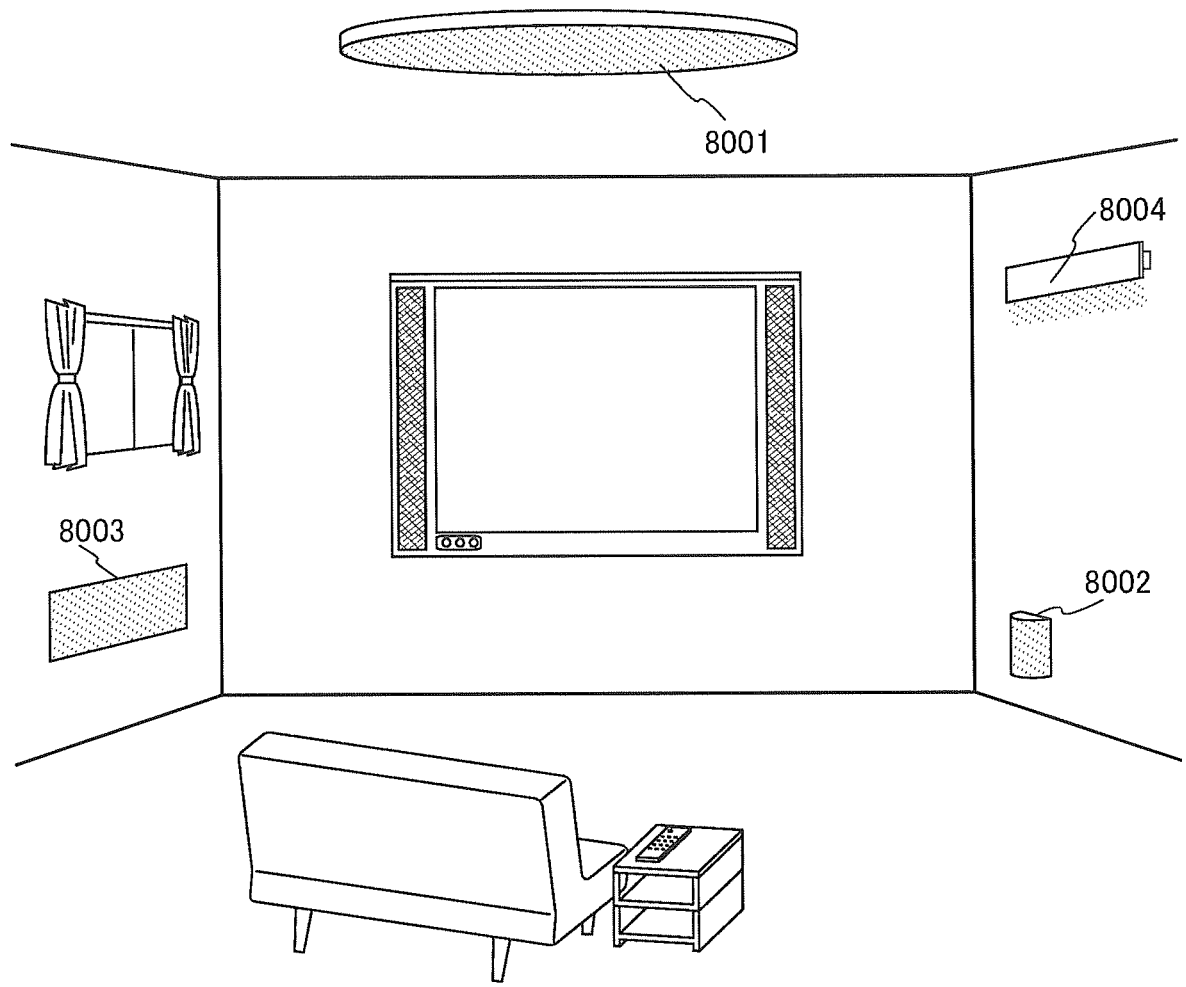
FIG. 8 illustrates lighting devices.

In this embodiment, application examples of lighting devices fabricated using the light-emitting device of one embodiment of the present invention or the light-emitting element which is a part of the light-emitting device will be described with reference to FIG. 8.

A ceiling light 8001 can be used as an indoor lighting device. Examples of the ceiling light 8001 include a direct-mount light and an embedded light. Such a lighting device is fabricated using the light-emitting device and a housing or a cover in combination. Besides, application to a cord pendant light (light that is suspended from a ceiling by a cord) is also possible.

A foot light 8002 lights a floor so that safety on the floor can be improved. For example, it can be effectively used in a bedroom, on a staircase, or on a passage. In that case, the size or shape of the foot light can be changed depending on the area or structure of a room. The foot light 8002 can be a stationary lighting device fabricated using the light-emitting device and a support base in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be increased. The sheet-like lighting can also be used on a wall or housing having a curved surface.

In addition, a lighting device 8004 in which the direction of light from a light source is controlled to be only a desired direction can be used.

Besides the above examples, when the light-emitting device of one embodiment of the present invention or the light-emitting element which is a part of the light-emitting device is used as part of furniture in a room, a lighting device that functions as the furniture can be obtained.

As described above, a variety of lighting devices that include the light-emitting device can be obtained. Note that these lighting devices are also embodiments of the present invention.

The structures described in this embodiment can be combined with any of the structures described in the other embodiments as appropriate.

Example 1

Synthesis Example 1

Described in this synthesis example is a method for synthesizing 4-[3-(dibenzothiophen-4-yl)phenyl]-8-(triphenylen-2-yl)-[1]benzofuro[3,2-d]pyrimidine (abbreviation: 8Tp-4mDBtPBfpm), which is the organic compound of one embodiment of the present invention represented by Structural Formula (100) in Embodiment 1. Note that the structure of 8Tp-4mDBtPBfpm is shown below.

[Chemical Formula 27]

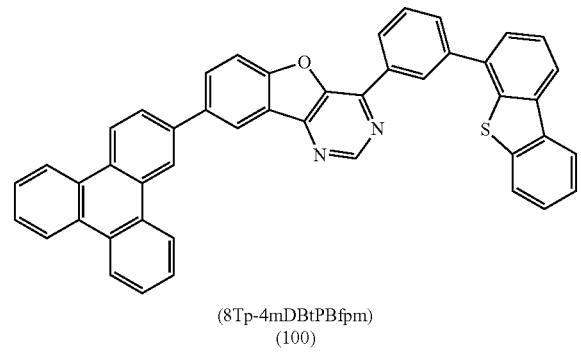

(8Tp-4mDBtPBfpm)
(100)

Synthesis of 8Tp-4mDBtPBfpm

First, 1.5 g of 8-chloro-4-[3-(dibenzothiophen-4-yl)phenyl]-[1]benzofuro[3,2-d]pyrimidine, 1.5 g of 4,4,5,5-tetramethyl-2-(triphenylen-2-yl)-1,3,2-dioxaborolane, 2.7 g of tripotassium phosphate, 35 mL of diglyme, and 0.93 g of t-butanol were put into a three-neck flask. The air in the flask was replaced with nitrogen. After adding of 15 mg of palladium(II) acetate and 47 mg of di(1-adamantyl)-n-butylphosphine, the mixture was heated under a nitrogen stream at 130° C. for 6 hours. Water was added to the obtained reaction mixture and filtered, and the residue was washed with water, ethanol, and toluene in this order.

Then, the residue was dissolved in boiled toluene and filtered. Furthermore, the solvent of the obtained filtrate was concentrated and recrystallized to give 0.52 g of a target pale yellow solid in a yield of 25%. Synthesis Scheme (a-1) is shown below.

[Chemical Formula 28]

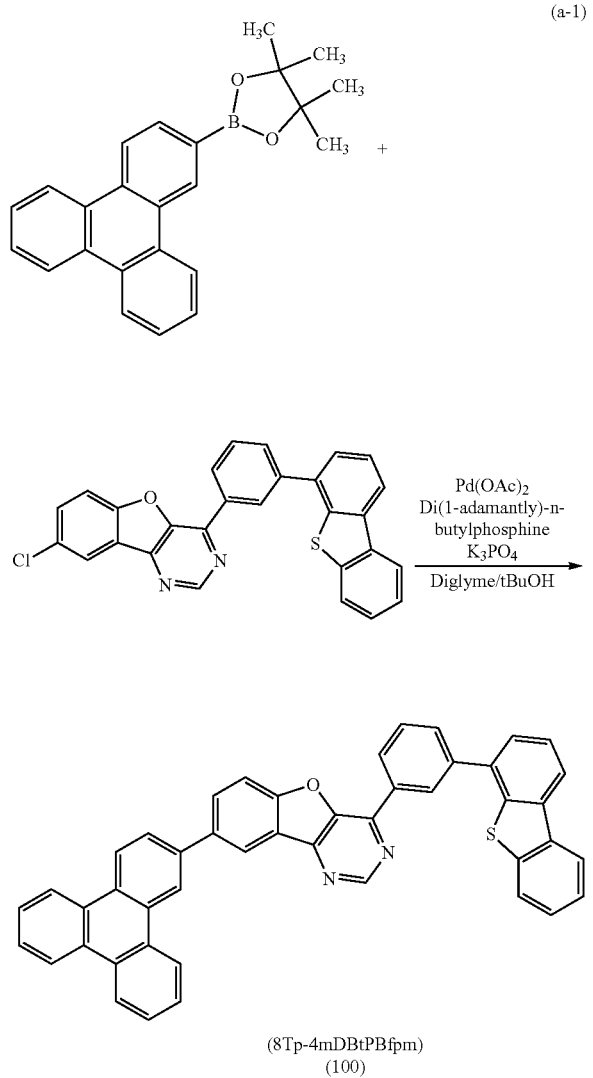

By a train sublimation method, 0.52 g of the obtained pale yellow solid was purified by sublimation. In the purification by sublimation, the solid was heated at 360° C. under a pressure of 2.3 Pa with an argon gas flow rate of 10 mL/min. After the purification by sublimation, 0.36 g of a target yellow solid was obtained at a collection rate of 69%.

Figure 9:
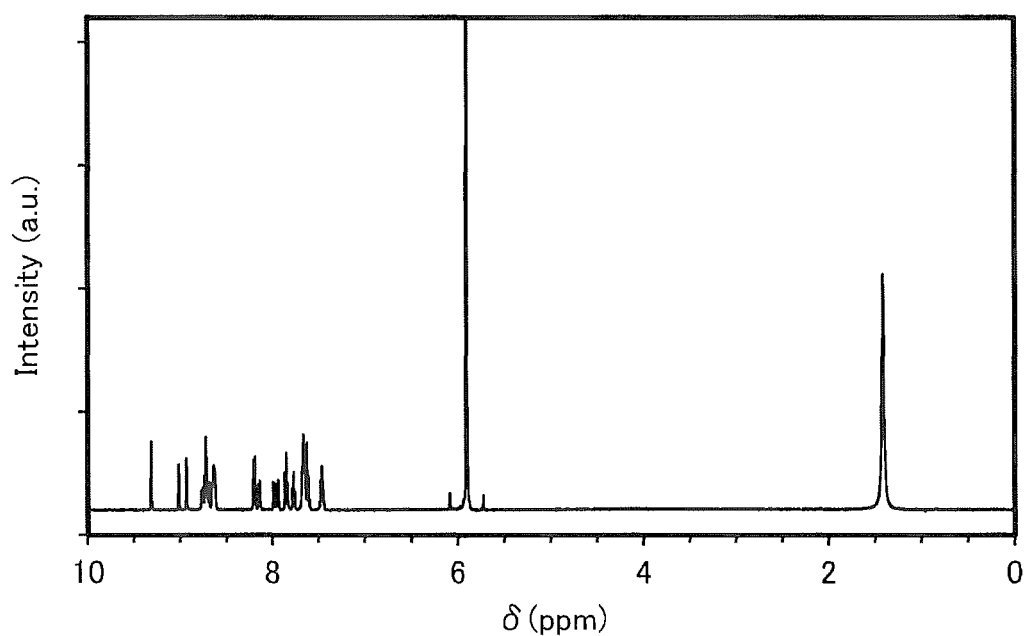
FIG. 9 is a $^1$H-NMR chart of an organic compound represented by Structural Formula (100).

Analysis results by nuclear magnetic resonance ($^1$H-NMR) spectroscopy of the obtained yellow solid are shown below. FIG. 9 is the $^1$H-NMR chart. The results reveal that 8Tp-4mDBtPBfpm, the organic compound represented by Structural Formula (100), was obtained in this example.

$^1$H-NMR. δ (TCE-d$_2$): 7.44-7.49 (m, 2H), 7.60-7.66 (m, 6H), 7.76-7.79 (t, 1H), 7.84-7.87 (t, 2H), 7.95 (d, 1H), 7.98 (d, 1H), 8.15 (d, 1H), 8.20 (d, 2H), 8.63-8.67 (m, 3H), 8.69-8.76 (m, 4H), 8.93 (s, 1H), 9.02 (s, 1H), 9.31 (s, 1H).

Figure 10A:
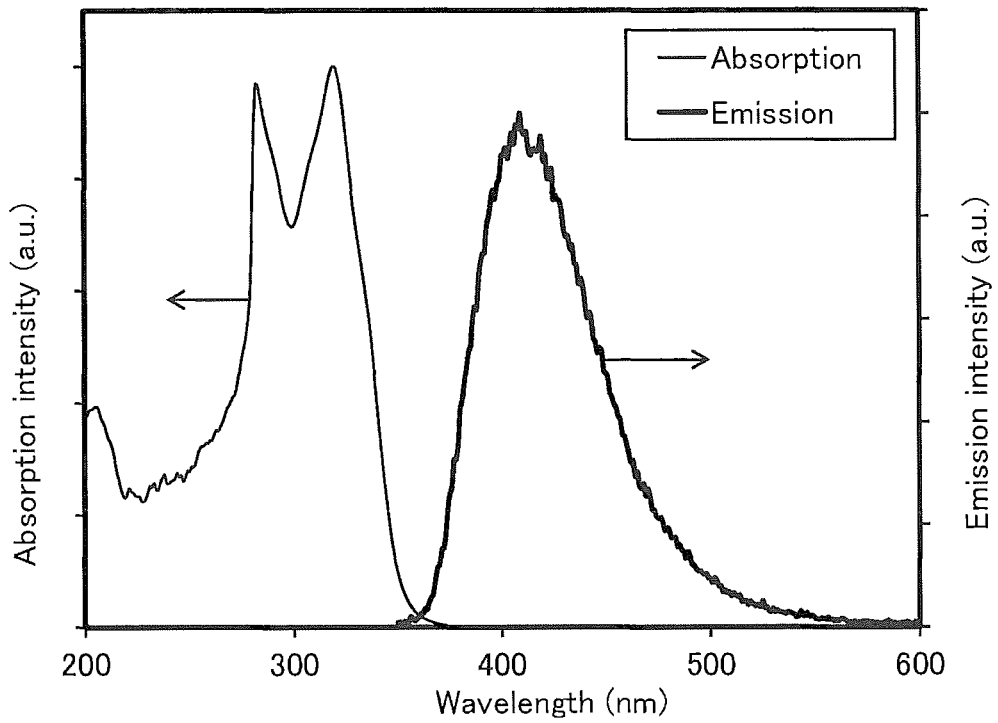
FIGS. 10A and 10B show ultraviolet-visible absorption and emission spectra of the organic compound represented by Structural Formula (100).

Next, the absorption spectrum and emission spectrum of 8Tp-4mDBtPBfpm in a toluene solution are shown in FIG. 10A. The horizontal axis represents wavelength and the vertical axes represent absorption intensity and emission intensity.

The absorption spectrum was measured with an ultraviolet-visible spectrophotometer (V-550, produced by JASCO Corporation). To calculate the absorption spectrum of 8Tp-4mDBtPBfpm in a toluene solution, the absorption spectrum of toluene put in a quartz cell was measured and then subtracted from the absorption spectrum of a toluene solution of 8Tp-4mDBtPBfpm put in a quartz cell. The emission spectrum was measured with a PL-EL measurement apparatus (produced by Hamamatsu Photonics K.K.). To obtain the emission spectrum of 8Tp-4mDBtPBfpm in a toluene solution, the emission spectrum of a toluene solution of 8Tp-4mDBtPBfpm put in a quartz cell was measured.

As shown in FIG. 10A, the toluene solution of 8Tp-4mDBtPBfpm exhibited an absorption peak at around 283 nm, 320 nm, and 333 nm and an emission wavelength peak at around 409 nm (excitation wavelength: 333 nm).

Figure 10B:
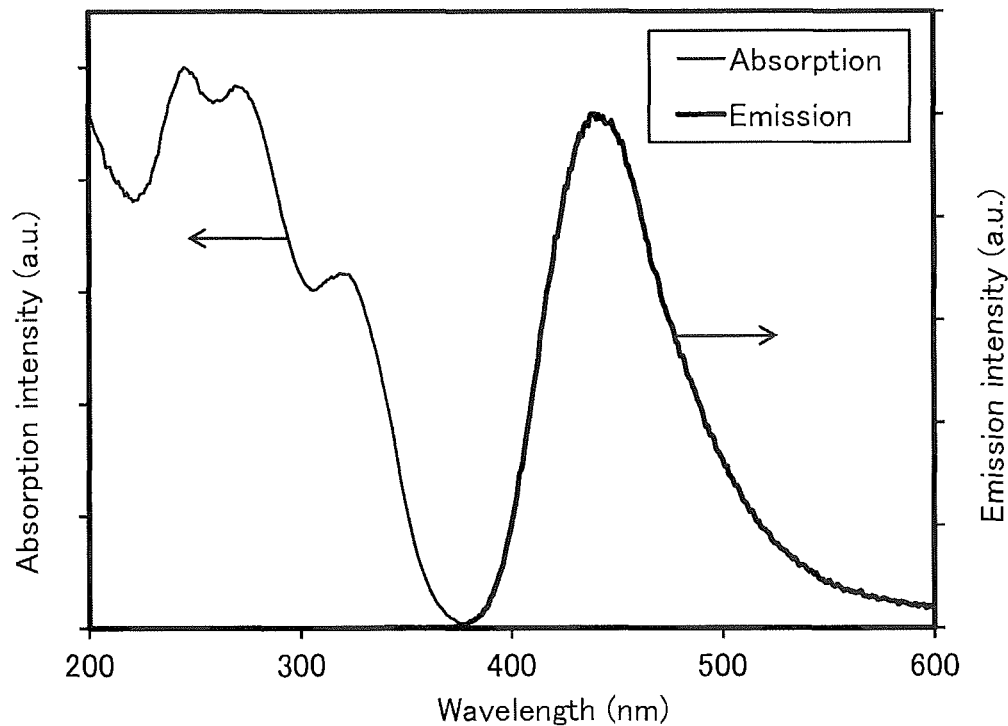

Next, the absorption spectrum and emission spectrum of a solid thin film of 8Tp-4mDBtPBfpm were measured. The solid thin film was fabricated over a quartz substrate by a vacuum evaporation method. The absorption spectrum of the thin film was calculated using an absorbance ($-\log_{10}$ [% T/(100–% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured with a fluorescence spectrophotometer (FS920 manufactured by Hamamatsu Photonics K.K.). The obtained absorption and emission spectra of the solid thin film are shown in FIG. 10B. The horizontal axis represents wavelength and the vertical axes represent absorption intensity and emission intensity.

As shown by the results in FIG. 10B, the solid thin film of 8Tp-4mDBtPBfpm exhibited an absorption peak at around 245 nm, 270 nm, and 319 nm and an emission wavelength peak at around 440 nm (excitation wavelength: 330 nm).

Next, 8Tp-4mDBtPBfpm obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, a sample was prepared by dissolving a given concentration of 8Tp-4mDBtPBfpm in an organic solvent, and the injection amount was 5.0 μL.

A component with m/z of 654.18, which is an ion derived from 8Tp-4mDBtPBfpm, was subjected to the MS$^2$ analysis by a Targeted-MS² method. For the Targeted-MS² analysis, the mass range of a target ion was set to m/z=654.18±2.0 (isolation window=4) and detection was performed in a positive mode. Measurement was performed with a normalized collision energy (NCE) for accelerating a target ion in a collision cell set to 70. The obtained MS spectrum is shown in FIG. 11.

Figure 11:
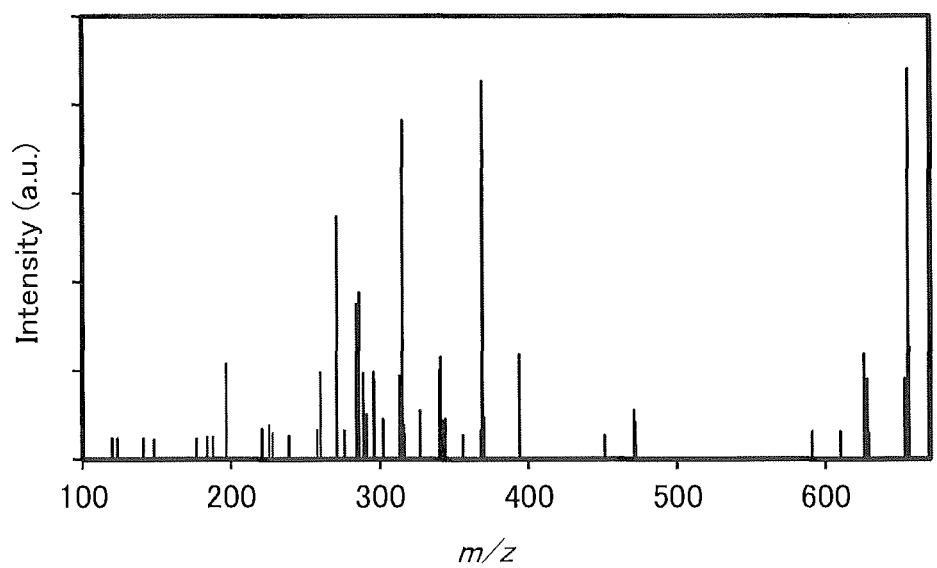
FIG. 11 shows an MS spectrum of the organic compound represented by Structural Formula (100).

FIG. 11 shows that product ions of 8Tp-4mDBtPBfpm are mainly detected around m/z=626, 591, 471, 451, 394, 369, 341, 315, 286, 271, 260, 226, and 197. The results in FIG. 11 show characteristics derived from 8Tp-4mDBtPBfpm and therefore can be regarded as important data for identifying 8Tp-4mDBtPBfpm contained in a mixture.

It is presumed that the product ion around m/z=626 is a cation generated due to dissociation of nitrile by cleavage of a pyrimidine ring and the product ion around m/z=394 is a cation generated due to dissociation of 4-phenyldibenzothiophene, indicating that 8Tp-4mDBtPBfpm includes phenyldibenzothiophene.

The product ion around m/z=197 is presumed to be a cation generated due to dissociation of a dibenzothiophenyl group, indicating that 8Tp-4mDBtPBfpm includes a dibenzothiophenyl group.

Example 2

Synthesis Example 2

Described in this example is a method for synthesizing 4-[3-(dibenzothiophen-4-yl)phenyl]-8-(9,9-dimethylfluoren-2-yl)-[1]benzofuro[3,2-d]pyrimidine (abbreviation: 8FL-4mDBtPBfpm), which is the organic compound of one embodiment of the present invention represented by Structural Formula (101) in Embodiment 1. Note that the structure of 8FL-4mDBtPBfpm is shown below.

[Chemical Formula 29]

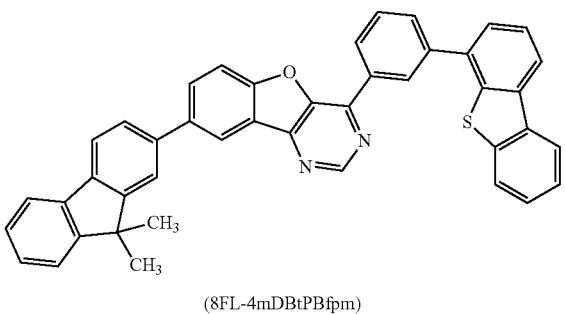

(101)

(8FL-4mDBtPBfpm)

Synthesis of 4-[3-(dibenzothiophen-4-yl)phenyl]-8-(9,9-dimethylfluoren-2-yl)-[1]benzofuro[3,2-d]pyrimidine (Abbreviation: 8FL-4mDBtPBfpm)

First, 1.5 g of 8-chloro-4-[3-(dibenzothiophen-4-yl)phenyl]-[1]benzofuro[3,2-d]pyrimidine, 1.0 g of 9,9-dimethylfluoren-2-boronic acid, 2.7 g of tripotassium phosphate, 35 mL of diglyme, and 1.9 g of t-butanol were put into a three-neck flask. The air in the flask was replaced with nitrogen. After adding of 28 mg of palladium(II) acetate and 93 mg of di(1-adamantyl)-n-butylphosphine, the mixture was heated under a nitrogen stream at 135° C. for 15 hours. Water was added to the obtained reaction mixture and filtered, and the residue was washed with water and ethanol in this order.

Then, the residue was dissolved in boiled toluene and filtered through a filter aid filled with Celite, alumina, and Celite in this order. The obtained solution was concentrated and dried, and then recrystallized with toluene and ethanol to give 1.6 g of a target yellowish white solid in a yield of 79%. Synthesis Scheme (b-1) is shown below.

[Chemical Formula 30]

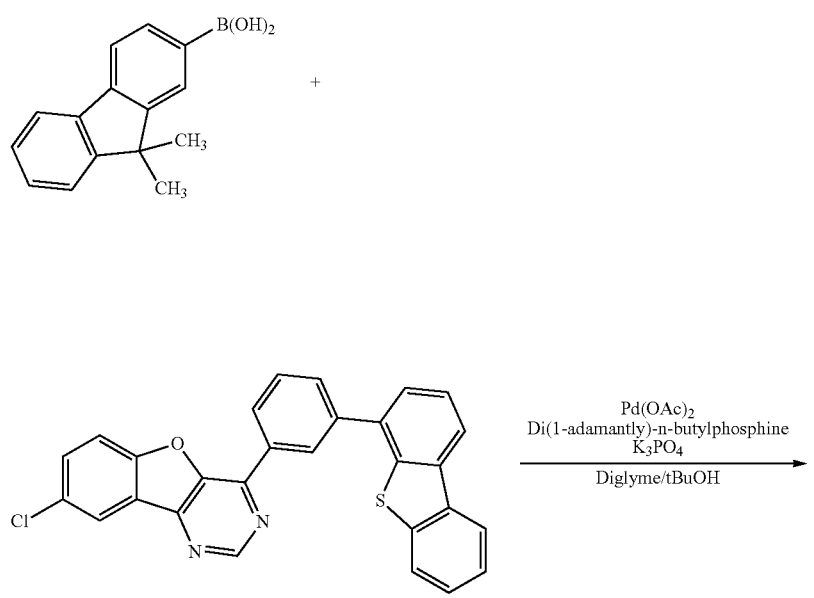

(b-1)

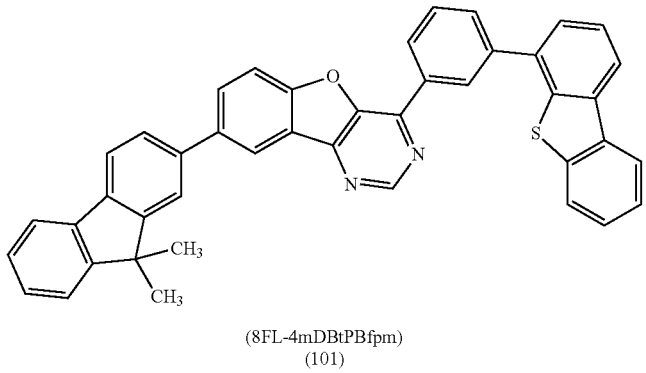

(8FL-4mDBtPBfpm)
(101)

By a train sublimation method, 1.6 g of the obtained yellowish white solid was purified by sublimation. In the purification by sublimation, the solid was heated at 315° C. under a pressure of 2.8 Pa with an argon gas flow rate of 10 mL/min. After the purification by sublimation, 1.0 g of a target yellow solid was obtained at a collection rate of 63%.

Figure 12:
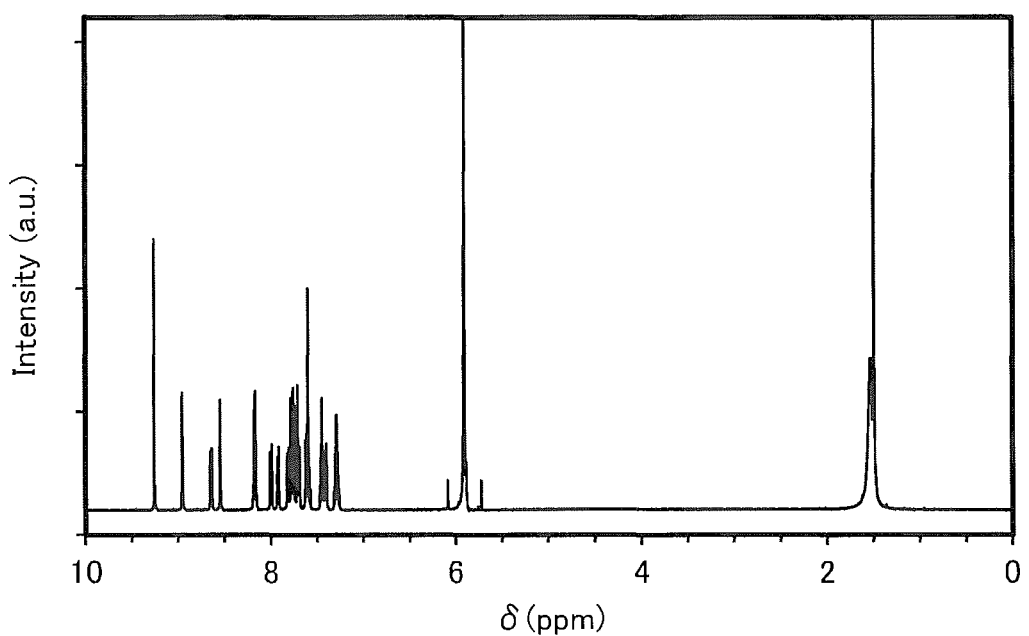
FIG. 12 is a $^1$H-NMR chart of an organic compound represented by Structural Formula (101).

Analysis results by nuclear magnetic resonance ($^1$H-NMR) spectroscopy of the obtained yellow solid are shown below. FIG. 12 is the $^1$H-NMR chart. The results reveal that 8FL-4mDBtPBfpm, the organic compound represented by Structural Formula (101), was obtained in this example.

$^1$H-NMR. δ (TCE-d$_2$): 1.50 (s, 6H), 7.27-7.32 (m, 2H), 7.40-7.47 (m, 3H), 7.56-7.63 (m, 3H), 7.69-7.79 (m, 5H), 7.82 (d, 1H), 7.92 (d, 1H), 8.00 (dd, 1H), 8.18 (dd, 2H), 8.55 (ds, 1H), 8.65 (d, 1H), 8.96 (s, 1H), 9.26 (s, 1H).

Figure 13A:
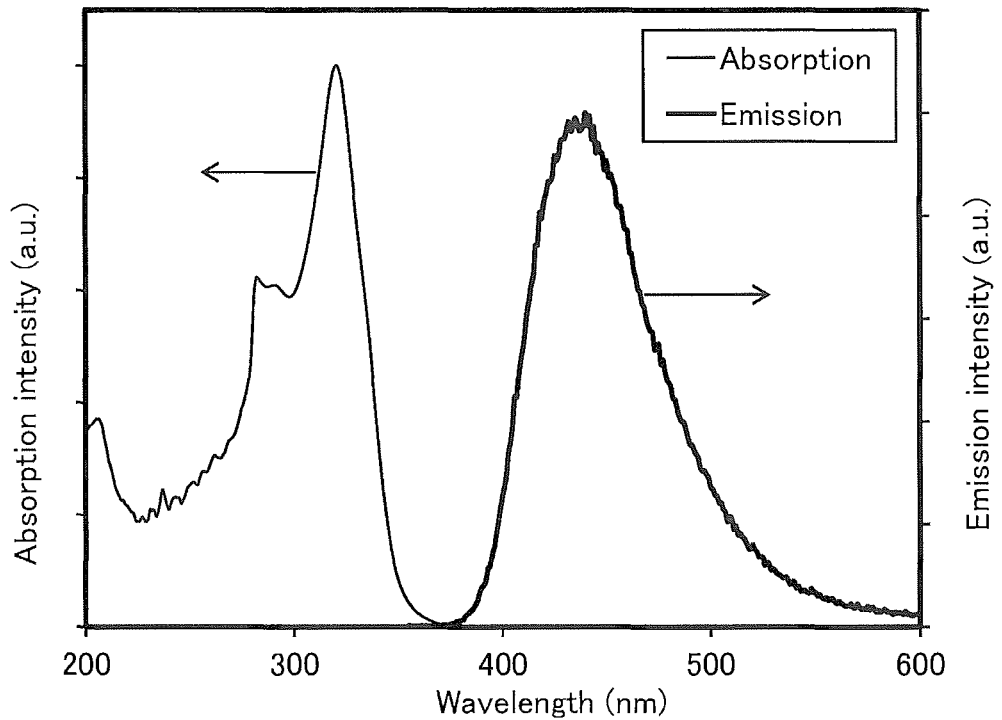
FIGS. 13A and 13B show ultraviolet-visible absorption and emission spectra of the organic compound represented by Structural Formula (101).

Next, the absorption spectrum and emission spectrum of 8FL-4mDBtPBfpm in a toluene solution are shown in FIG. 13A. The horizontal axis represents wavelength and the vertical axes represent absorption intensity and emission intensity.

The absorption spectrum was measured with an ultraviolet-visible spectrophotometer (V-550, produced by JASCO Corporation). To calculate the absorption spectrum of 8FL-4mDBtPBfpm in a toluene solution, the absorption spectrum of toluene put in a quartz cell was measured and then subtracted from the absorption spectrum of a toluene solution of 8FL-4mDBtPBfpm put in a quartz cell. The emission spectrum was measured with a PL-EL measurement apparatus (produced by Hamamatsu Photonics K.K.). To obtain the emission spectrum of 8FL-4mDBtPBfpm in a toluene solution, the emission spectrum of a toluene solution of 8FL-4mDBtPBfpm put in a quartz cell was measured.

As shown in FIG. 13A, the toluene solution of 8FL-4mDBtPBfpm exhibited an absorption peak at around 281 nm, 294 nm, 320 nm, and 334 nm and an emission wavelength peak at around 422 nm (excitation wavelength: 331 nm).

Figure 13B:
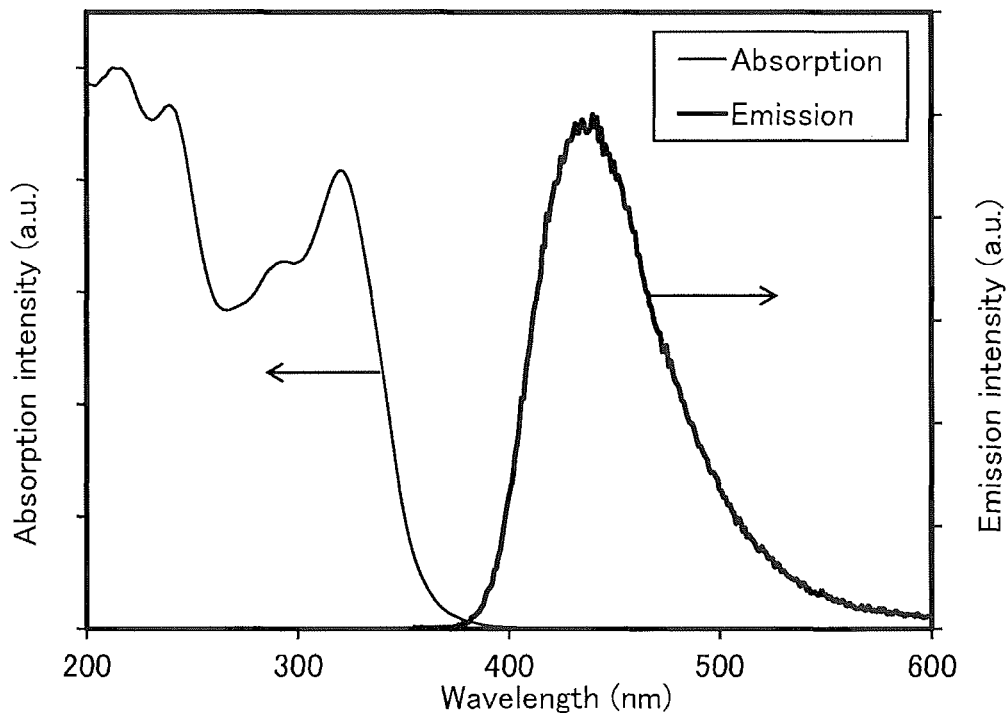

Next, the absorption spectrum and emission spectrum of a solid thin film of 8FL-4mDBtPBfpm were measured. The solid thin film was fabricated over a quartz substrate by a vacuum evaporation method. The absorption spectrum of the thin film was calculated using an absorbance (−log$_{10}$ [% T/(100−% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured with a fluorescence spectrophotometer (FS920 manufactured by Hamamatsu Photonics K.K.). The obtained absorption and emission spectra of the solid thin film are shown in FIG. 13B. The horizontal axis represents wavelength and the vertical axes represent absorption intensity and emission intensity.

As shown by the results in FIG. 13B, the solid thin film of 8FL-4mDBtPBfpm exhibited an absorption peak at around 213 nm, 237 nm, 290 nm, 322 nm, and 338 nm and an emission wavelength peak at around 437 nm (excitation wavelength: 350 nm).

Next, 8FL-4mDBtPBfpm obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, a sample was prepared by dissolving a given concentration of 8FL-4mDBtPBfpm in an organic solvent, and the injection amount was 5.0 μL.

A component with m/z of 621.19, which is an ion derived from 8FL-4mDBtPBfpm, was subjected to the MS$^2$ analysis by a Targeted-MS$^2$ method. For the Targeted-MS$^2$ analysis, the mass range of a target ion was set to m/z=621.19±2.0 (isolation window=4) and detection was performed in a positive mode. Measurement was performed with a normalized collision energy (NCE) for accelerating a target ion in a collision cell set to 80. The obtained MS spectrum is shown in FIG. 14.

Figure 14:
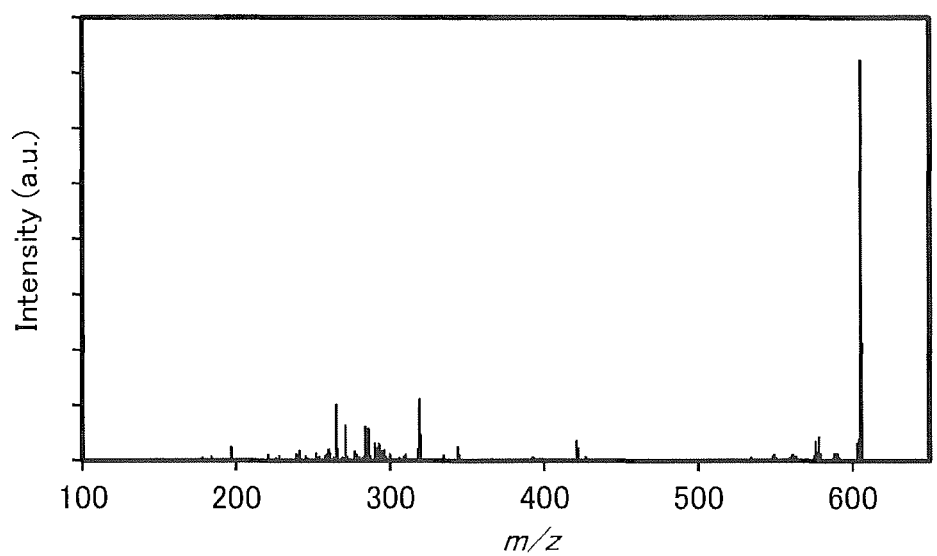
FIG. 14 shows an MS spectrum of the organic compound represented by Structural Formula (101).

FIG. 14 shows that product ions of 8FL-4mDBtPBfpm are mainly detected around m/z=605, 578, 421, 344, 319, 284, 265, 241, and 197. The results in FIG. 14 show characteristics derived from 8FL-4mDBtPBfpm and therefore can be regarded as important data for identifying 8FL-4mDBtPBfpm contained in a mixture.

The product ion around m/z=605 is presumed to be a cation generated due to dissociation of a methyl group in 8FL-4mDBtPBfpm, indicating that 8FL-4mDBtPBfpm includes a methyl group. The other product ions are further dissociated from a state where a methyl group in 8FL-4mDBtPBfpm has been dissociated. The product ion around m/z=343 is presumed to be a cation generated due to dissociation of a phenyl group and a dibenzothiophenyl group, indicating that 8FL-4mDBtPBfpm includes a phenyl group and a dibenzothiophenyl group.

The product ion around m/z=197 is presumed to be a cation of a dibenzothiophenyl group, indicating that 8FL-4mDBtPBfpm includes a dibenzothiophenyl group.

Example 3

Synthesis Example 3

Described in this example is a method for synthesizing 4-[3-(dibenzothiophen-4-yl)phenyl]-8-(naphthalen-2-yl)-[1]benzofuro[3,2-d]pyrimidine (abbreviation: 8βN-4mDBtPBfpm), which is the organic compound of one embodiment of the present invention represented by Structural Formula (102) in Embodiment 1. Note that the structure of 8βN-4mDBtPBfpm is shown below.

[Chemical Formula 31]

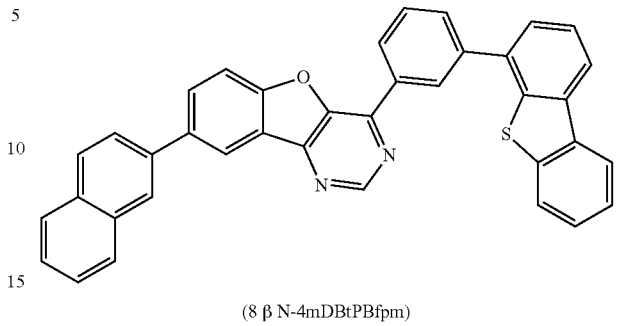

(8 β N-4mDBtPBfpm)

Synthesis of 4-[3-(dibenzothiophen-4-yl)phenyl]-8-(naphthalen-2-yl)-[1]benzofuro[3,2-d]pyrimidine (abbreviation: 8βN-4mDBtPBfpm)

First, 1.5 g of 8-chloro-4-[3-(dibenzothiophen-4-yl)phenyl]-[1]benzofuro[3,2-d]pyrimidine, 0.73 g of 2-naphthaleneboronic acid, 1.5 g of cesium fluoride, and 32 mL of mesitylene were put into a 100-mL three-neck flask. The air in the flask was replaced with nitrogen. After adding of 70 mg of 2'-(dicyclohexylphosphino)acetophenone ethylene ketal and 89 mg of tris(dibenzylideneacetone)dipalladium (0) (abbreviation: Pd$_2$(dba)$_3$), the mixture was heated under a nitrogen stream at 120° C. for 5 hours. Water was added to the obtained reaction mixture and filtered, and the residue was washed with water and ethanol in this order.

The residue was dissolved in toluene and filtered through a filter aid filled with Celite, alumina, and Celite in this order. The solvent of the obtained solution was concentrated and recrystallized to give 1.5 g of a target pale yellow solid in a yield of 64%. Synthesis Scheme (c-1) is shown below.

[Chemical Formula 32]

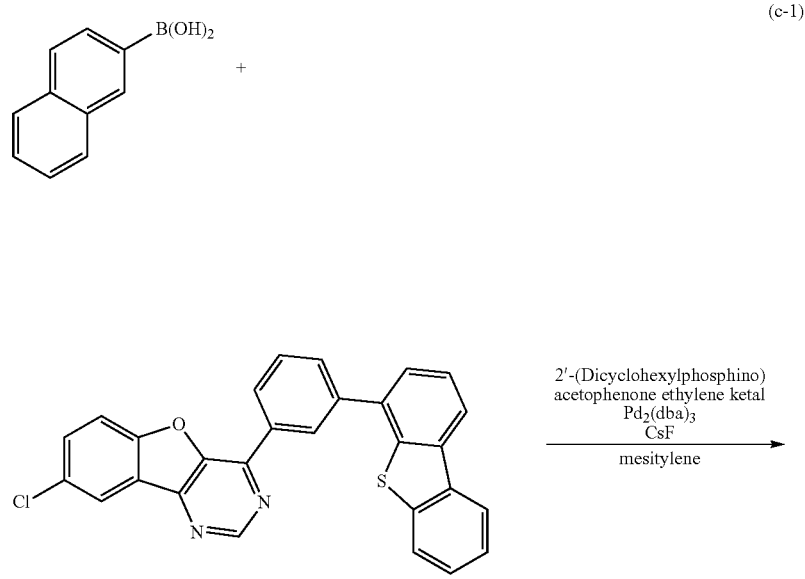

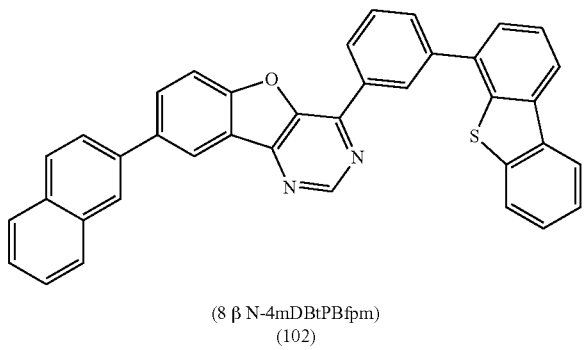

(8 β N-4mDBtPBfpm)
(102)

By a train sublimation method, 1.5 g of the obtained pale yellow solid was purified by sublimation. In the purification by sublimation, the solid was heated at 290° C. under a pressure of 2.0 Pa with an argon gas flow rate of 10 mL/min. After the purification by sublimation, 0.60 g of a target yellow solid was obtained at a collection rate of 39%.

Figure 15:
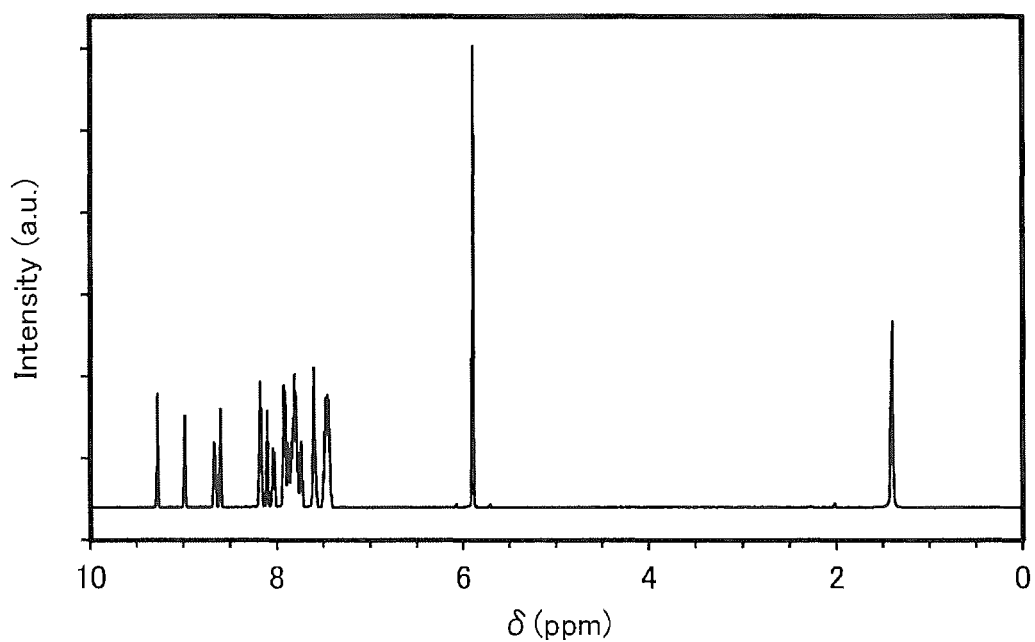
FIG. 15 is a $^1$H-NMR chart of an organic compound represented by Structural Formula (102).

Analysis results by nuclear magnetic resonance ($^1$H-NMR) spectroscopy of the obtained yellow solid are shown below. FIG. 15 is the $^1$H-NMR chart. The results reveal that 8βN-4mDBtPBfpm, the organic compound represented by Structural Formula (102), was obtained in this example.

$^1$H-NMR. δ (TCE-d$_2$): 7.45-7.50 (m, 4H), 7.57-7.62 (m, 2H), 7.72-7.93 (m, 8H), 8.03 (d, 1H), 8.10 (s, 1H), 8.17 (d, 2H), 8.60 (s, 1H), 8.66 (d, 1H), 8.98 (s, 1H), 9.28 (s, 1H).

Figure 16A:
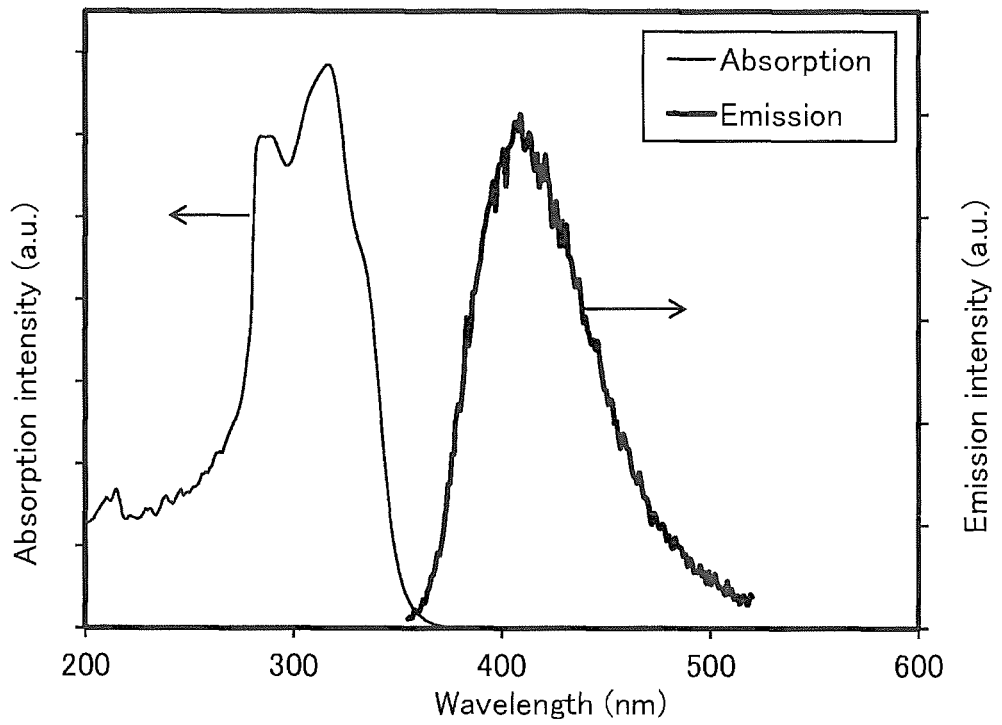
FIGS. 16A and 16B show ultraviolet-visible absorption and emission spectra of the organic compound represented by Structural Formula (102).

Next, the absorption spectrum and emission spectrum of 8βN-4mDBtPBfpm in a toluene solution are shown in FIG. 16A. The horizontal axis represents wavelength and the vertical axes represent absorption intensity and emission intensity.

The absorption spectrum was measured with an ultraviolet-visible spectrophotometer (V-550, produced by JASCO Corporation). To calculate the absorption spectrum of 8βN-4mDBtPBfpm in a toluene solution, the absorption spectrum of toluene put in a quartz cell was measured and then subtracted from the absorption spectrum of a toluene solution of 8βN-4mDBtPBfpm put in a quartz cell. The emission spectrum was measured with a PL-EL measurement apparatus (produced by Hamamatsu Photonics K.K.). To obtain the emission spectrum of 8βN-4mDBtPBfpm in a toluene solution, the emission spectrum of a toluene solution of 8βN-4mDBtPBfpm put in a quartz cell was measured.

As shown in FIG. 16A, the toluene solution of 8βN-4mDBtPBfpm exhibited an absorption peak at around 283 nm, 290 nm, 317 nm, and 333 nm and an emission wavelength peak at around 409 nm (excitation wavelength: 337 nm).

Figure 16B:
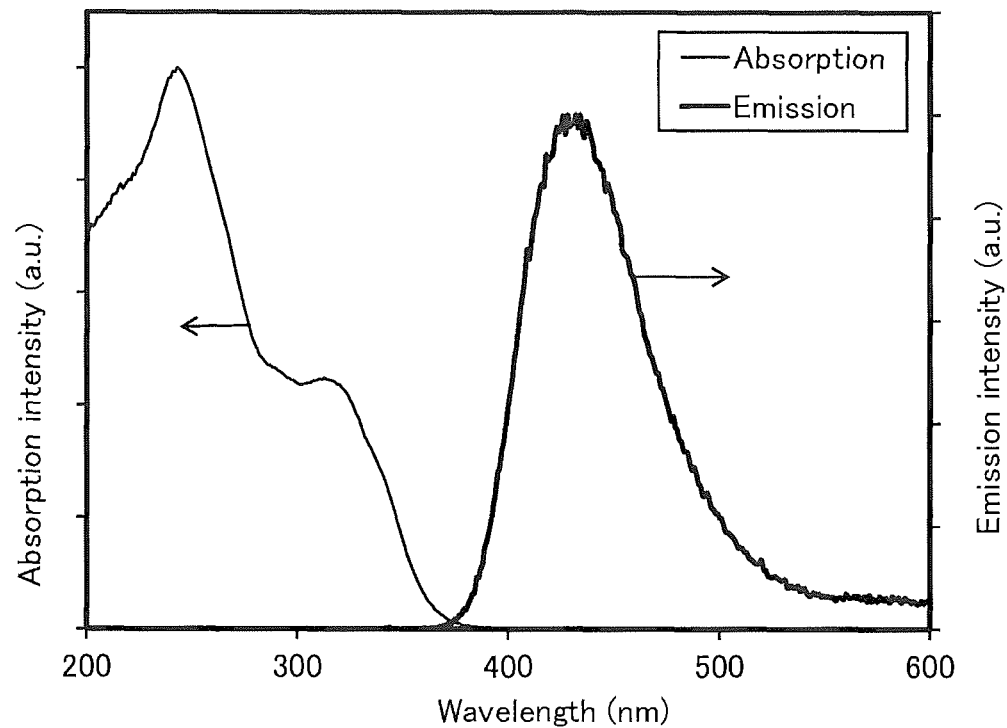

Next, the absorption spectrum and emission spectrum of a solid thin film of 8βN-4mDBtPBfpm were measured. The solid thin film was fabricated over a quartz substrate by a vacuum evaporation method. The absorption spectrum of the thin film was calculated using an absorbance ($-\log_{10}$ [% T/(100−% R)]) obtained from the transmittance and reflectance of the thin film including the substrate. Note that % T represents transmittance and % R represents reflectance. The absorption spectrum was measured with a UV-visible spectrophotometer (U-4100 manufactured by Hitachi High-Technologies Corporation). The emission spectrum was measured with a fluorescence spectrophotometer (FS920 manufactured by Hamamatsu Photonics K.K.). The obtained absorption and emission spectra of the solid thin film are shown in FIG. 16B. The horizontal axis represents wavelength and the vertical axes represent absorption intensity and emission intensity.

As shown by the results in FIG. 16B, the solid thin film of 8βN-4mDBtPBfpm exhibited an absorption peak at around 243 nm, 266 nm, 290 nm, 314 nm, and 341 nm and an emission wavelength peak at around 430 nm (excitation wavelength: 330 nm).

Next, 8βN-4mDBtPBfpm obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, a sample was prepared by dissolving a given concentration of 8βN-4mDBtPBfpm in an organic solvent, and the injection amount was 5.0 μL.

A component with m/z of 554.15, which is an ion derived from 8βN-4mDBtPBfpm, was subjected to the MS² analysis by a Targeted-MS² method. For the Targeted-MS² analysis, the mass range of a target ion was set to m/z=554.15±2.0 (isolation window=4) and detection was performed in a positive mode. Measurement was performed with a normalized collision energy (NCE) for accelerating a target ion in a collision cell set to 65. The obtained MS spectrum is shown in FIG. 17.

Figure 17:
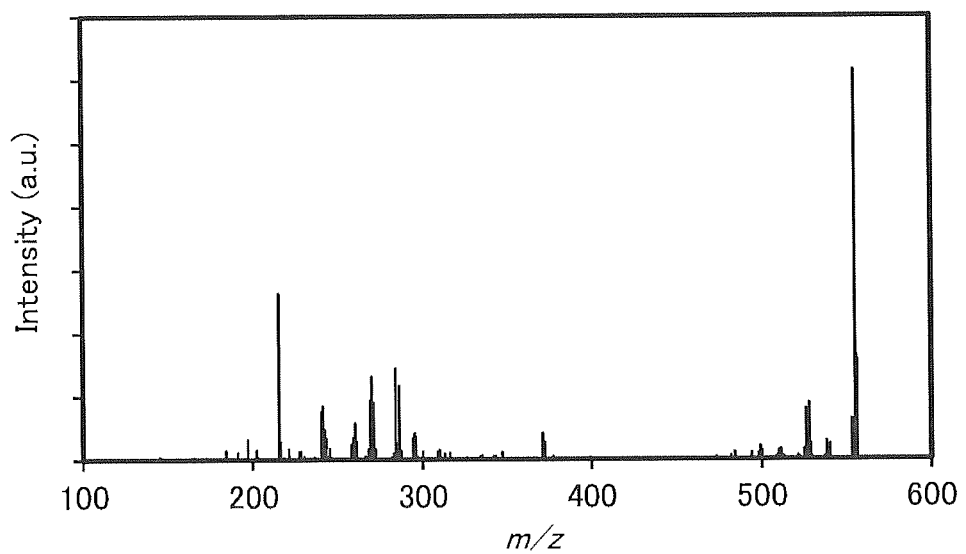
FIG. 17 shows an MS spectrum of the organic compound represented by Structural Formula (102).

FIG. 17 shows that product ions of 8βN-4mDBtPBfpm are mainly detected around m/z=528, 499, 371, 347, 310, 295, 284, 270, 260, 245, 241, 221, 215, and 197. The results in FIG. 17 show characteristics derived from 8βN-4mDBtPBfpm and therefore can be regarded as important data for identifying 8βN-4mDBtPBfpm contained in a mixture.

The product ion around m/z=371 is presumed to be a cation generated due to dissociation of a dibenzothiophenyl group, indicating that 8βN-4mDBtPBfpm includes a dibenzothiophenyl group.

Example 4

Described in this example are structures, fabrication methods, and characteristics of light-emitting elements 1 to 3 of embodiments of the present invention. The light-emitting element 1 uses for a light-emitting layer 4-[3-(dibenzothiophen-4-yl)phenyl]-8-(triphenylen-2-yl)-[1]benzofuro[3,2-d]pyrimidine (abbreviation: 8Tp-4mDBtPBfpm) (Structural Formula (100)) described in Example 1. The light-emitting element 2 uses for a light-emitting layer 4-[3-(dibenzothiophen-4-yl)phenyl]-8-(9,9-dimethylfluoren-2-yl)-[1]benzofuro[3,2-d]pyrimidine (abbreviation: 8FL-4mDBtPBfpm) (Structural Formula (101)) described in Example 2. The light-emitting element 3 uses for a light-emitting layer 4-[3-(dibenzothiophen-4-yl)phenyl]-8-(naphthalen-2-yl)-[1]benzofuro[3,2-d]pyrimidine (abbreviation: 8βN-4mDBtPBfpm) (Structural Formula (102)) described in Example 3. The light-emitting elements in this example have a structure illustrated in FIG. 18. Table 1 shows specific structures of the light-emitting elements. Chemical formulae of materials used in this example are shown below.

[Chemical Formula 33]

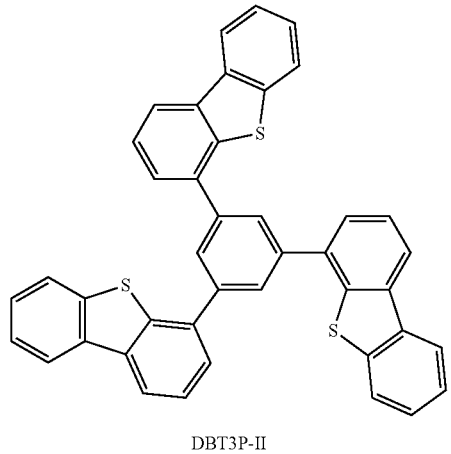

DBT3P-II

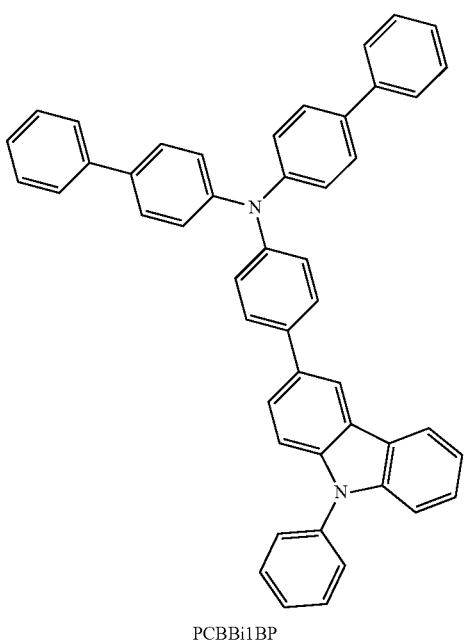

PCBBi1BP

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting element 1 | ITSO (70 nm) | DBT3P-II:MoOx (2:1 50 nm) | PCBBi1BP (20 nm) | * | 8Tp-4mDBtPBfpm (20 nm) | BPhen (15 nm) | LiF (1 nm) | Al (200 nm) |
| Light-emitting element 2 | ITSO (70 nm) | DBT3P-II:MoOx (2:1 50 nm) | PCBBi1BP (20 nm) | ** | 8FL-4mDBtPBfpm (20 nm) | BPhen (15 nm) | LiF (1 nm) | Al (200 nm) |
| Light-emitting element 3 | ITSO (70 nm) | DBT3P-II:MoOx (2:1 50 nm) | PCBBi1BP (20 nm) | *** | 8βN-4mDBtPBfpm (20 nm) | BPhen (15 nm) | LiF (1 nm) | Al (200 nm) |

\* 8Tp-4mDBtPBfpm:PCCP:Ir(ppy)₂(4dppy) (0.6:0.4:0.1 40 nm)
\*\* 8FL-4mDBtPBfpm:PCCP:Ir(ppy)₂(4dppy) (0.6:0.4:0.1 40 nm)
\*\*\* 8βN-4mDBtPBfpm:PCCP:Ir(ppy)₂(4dppy) (0.6:0.4:0.1 40 nm)

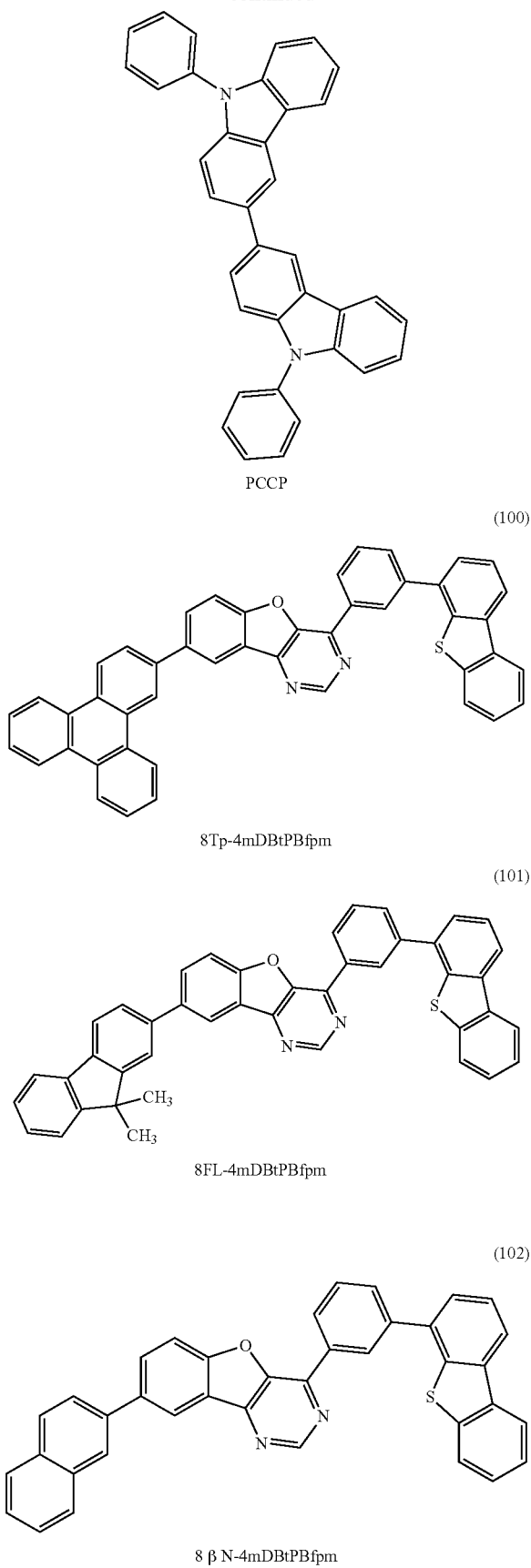

PCCP (100)

8Tp-4mDBtPBfpm (101)

8FL-4mDBtPBfpm (102)

8βN-4mDBtPBfpm

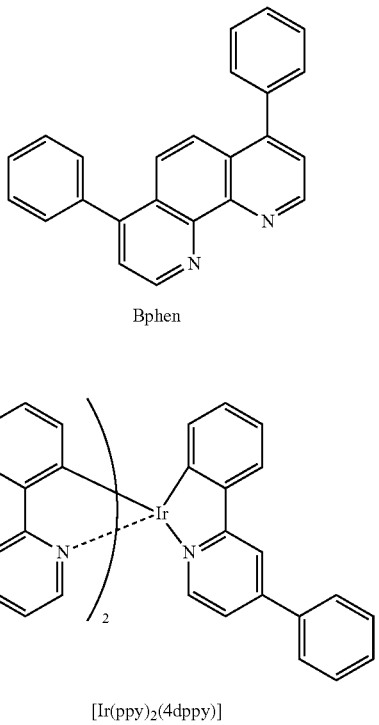

Bphen

[Ir(ppy)₂(4dppy)]

<<Fabrication of Light-Emitting Elements>>

Figure 18:
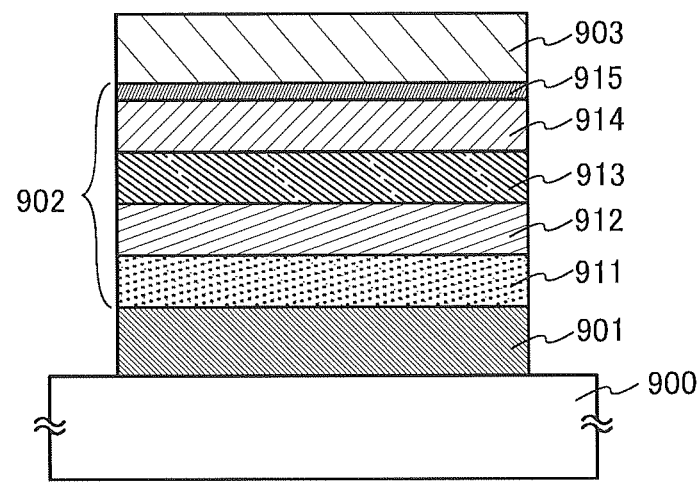
FIG. 18 illustrates a light-emitting element.

In each of the light-emitting elements described in this example, as illustrated in FIG. 18, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately $10^{-4}$ Pa, and was subjected to vacuum baking at 170° C. for 60 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to $10^{-4}$ Pa, the hole-injection layer 911 was formed by co-evaporation to have a mass ratio of DBT3P-II to molybdenum oxide of 2:1 and a thickness of 50 nm.

Then, the hole-transport layer 912 was formed over the hole-injection layer 911. The hole-transport layer 912 was formed to a thickness of 20 nm by evaporation of PCBBi1BR Next, the light-emitting layer 913 was formed over the hole-transport layer 912.

The light-emitting layer 913 in the light-emitting element 1 was formed by co-evaporation using 8Tp-4mDBtPBfpm as a host material, using PCCP as an assist material, and using [Ir(ppy)$_2$(4dppy)] as a guest material (a phosphorescent material) to have a weight ratio of 8Tp-4mDBtPBfpm to PCCP and [Ir(ppy)$_2$(4dppy)] of 0.6:0.4:0.1. The thickness was set to 40 nm.

The light-emitting layer 913 in the light-emitting element 2 was formed by co-evaporation using 8FL-4mDBtPBfpm as a host material, using PCCP as an assist material, and using [Ir(ppy)$_2$(4dppy)] as a guest material (a phosphorescent material) to have a weight ratio of 8FL-4mDBtPBfpm to PCCP and [Ir(ppy)$_2$(4dppy)] of 0.6:0.4:0.1. The thickness was set to 40 nm.

The light-emitting layer 913 in the light-emitting element 3 was formed by co-evaporation using 8βN-4mDBtPBfpm as a host material, using PCCP as an assist material, and using [Ir(ppy)$_2$(4dppy)] as a guest material (a phosphorescent material) to have a weight ratio of 8βN-4mDBtPBfpm to PCCP and [Ir(ppy)$_2$(4dppy)] of 0.6:0.4:0.1. The thickness was set to 40 nm.

Next, the electron-transport layer 914 was formed over the light-emitting layer 913. The electron-transport layer 914 in the light-emitting element 1 was formed by evaporation of 8Tp-4mDBtPBfpm and then BPhen to a thickness of 20 nm and 15 nm, respectively. The electron-transport layer 914 in the light-emitting element 2 was formed by evaporation of 8FL-4mDBtPBfpm and then BPhen to a thickness of 20 nm and 15 nm, respectively. The electron-transport layer 914 in the light-emitting element 3 was formed by evaporation of 8βN-4mDBtPBfpm and then BPhen to a thickness of 20 nm and 15 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting elements each including the EL layer between a pair of electrodes were formed over the substrate 900. Note that the hole-injection layer 911, the hole-transport layer 912, the light-emitting layer 913, the electron-transport layer 914, and the electron-injection layer 915 described above are functional layers forming the EL layer in one embodiment of the present invention. Furthermore, in all the evaporation steps in the above fabrication method, evaporation was performed by a resistance-heating method.

Each of the light-emitting elements fabricated as described above was sealed using another substrate (not illustrated) in such a manner that the substrate (not illustrated) was fixed to the substrate 900 with a sealing material in a glove box containing a nitrogen atmosphere, a sealant was applied so as to surround the light-emitting element formed over the substrate 900, and then irradiation with 365-nm ultraviolet light at 6 J/cm$^2$ was performed and heat treatment was performed at 80° C. for 1 hour.

<<Operation Characteristics of Light-Emitting Elements>>

Figure 19:
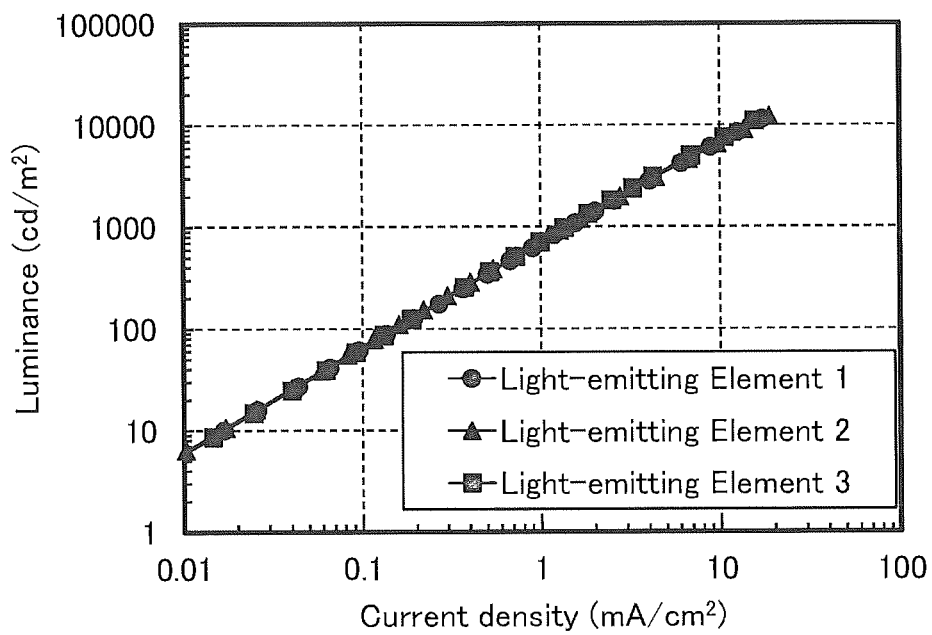
FIG. 19 shows current density-luminance characteristics of a light-emitting element 1, a light-emitting element 2, and a light-emitting element 3.
Figure 20:
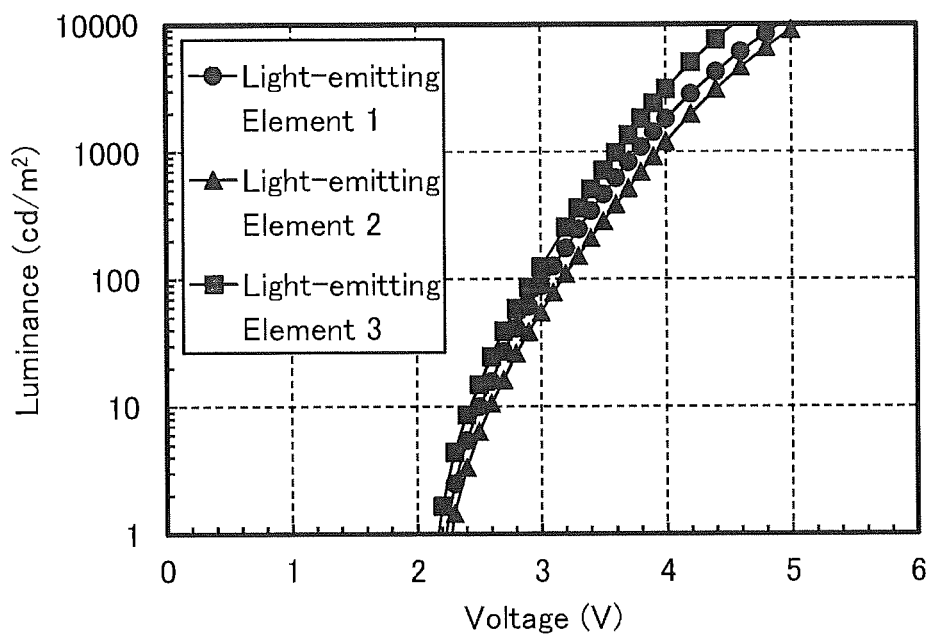
FIG. 20 shows voltage-luminance characteristics of the light-emitting element 1, the light-emitting element 2, and the light-emitting element 3.
Figure 21:
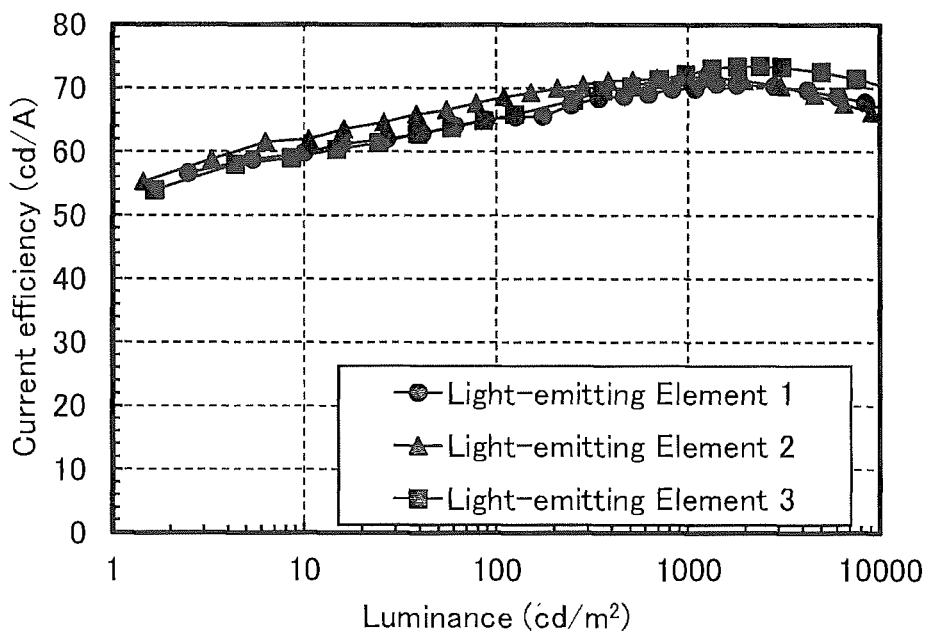
FIG. 21 shows luminance-current efficiency characteristics of the light-emitting element 1, the light-emitting element 2, and the light-emitting element 3.
Figure 22:
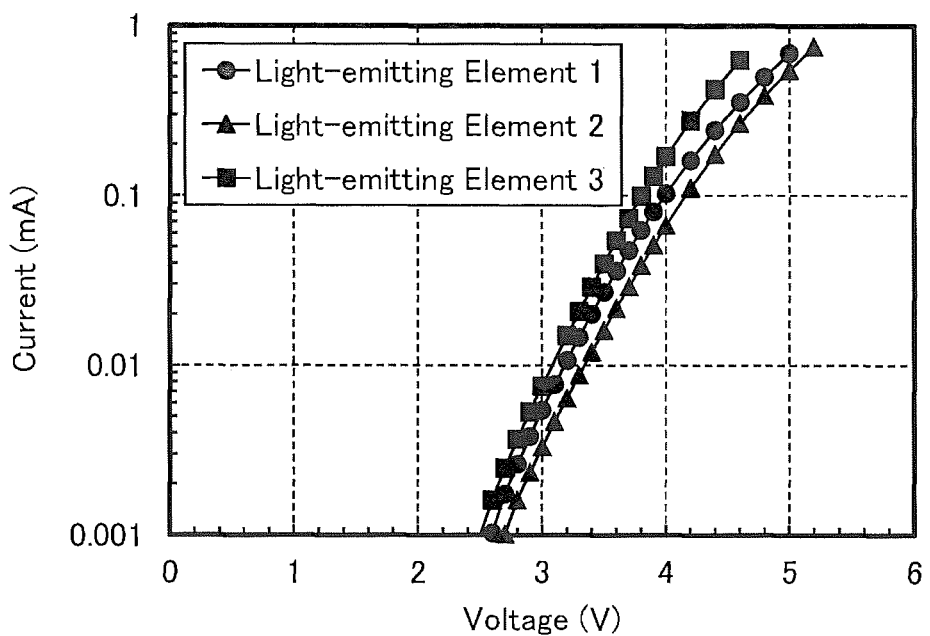
FIG. 22 shows voltage-current characteristics of the light-emitting element 1, the light-emitting element 2, and the light-emitting element 3.

Operation characteristics of the fabricated light-emitting elements were measured. Note that the measurement was performed at room temperature (in an atmosphere kept at 25° C.). As the results of the operation characteristics of the light-emitting elements 1 to 3, the current density-luminance characteristics are shown in FIG. 19, the voltage-luminance characteristics are shown in FIG. 20, the luminance-current efficiency characteristics are shown in FIG. 21, and the voltage-current characteristics are shown in FIG. 22.

Table 2 shows initial values of main characteristics of the light-emitting elements at around 1000 cd/m$^2$.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.8 | 0.062 | 1.6 | (0.45, 0.54) | 1100 | 70 | 57 | 21 |
| Light-emitting element 2 | 3.9 | 0.051 | 1.3 | (0.45, 0.54) | 920 | 72 | 57 | 22 |
| Light-emitting element 3 | 3.6 | 0.054 | 1.4 | (0.45, 0.54) | 980 | 72 | 62 | 22 |

The above results show that all the light-emitting elements fabricated in this example have excellent element characteristics.

Figure 23:
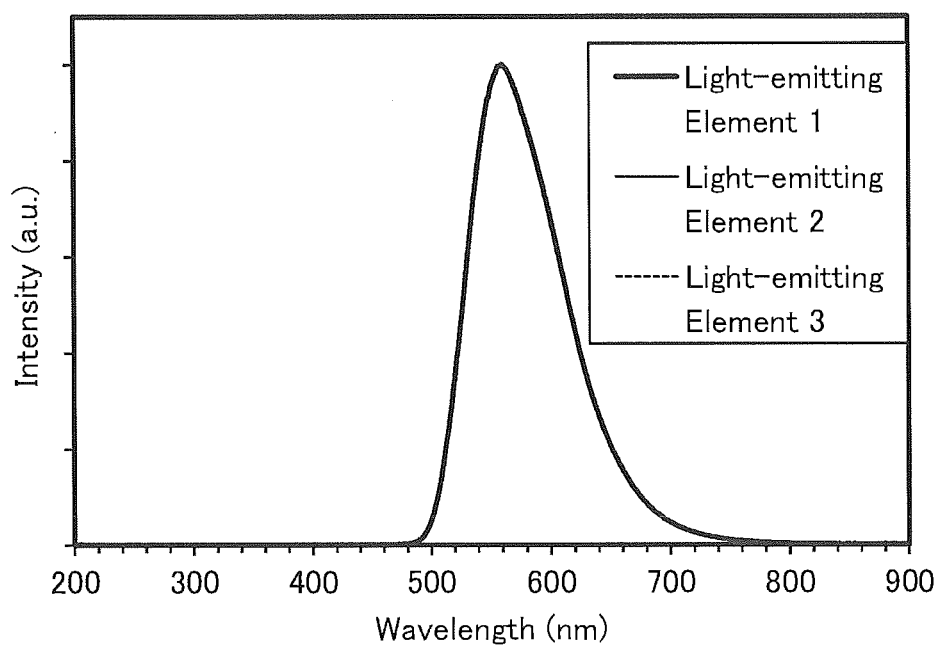
FIG. 23 shows emission spectra of the light-emitting element 1, the light-emitting element 2, and the light-emitting element 3.

FIG. 23 shows emission spectra when current at a current density of 2.5 mA/cm$^2$ was applied to the light-emitting elements. As shown in FIG. 23, the emission spectrum of each light-emitting element has a peak at around 560 nm, which is probably derived from light emission of [Ir(ppy)$_2$(4dppy)] contained in the light-emitting layer 913.

Figure 24:
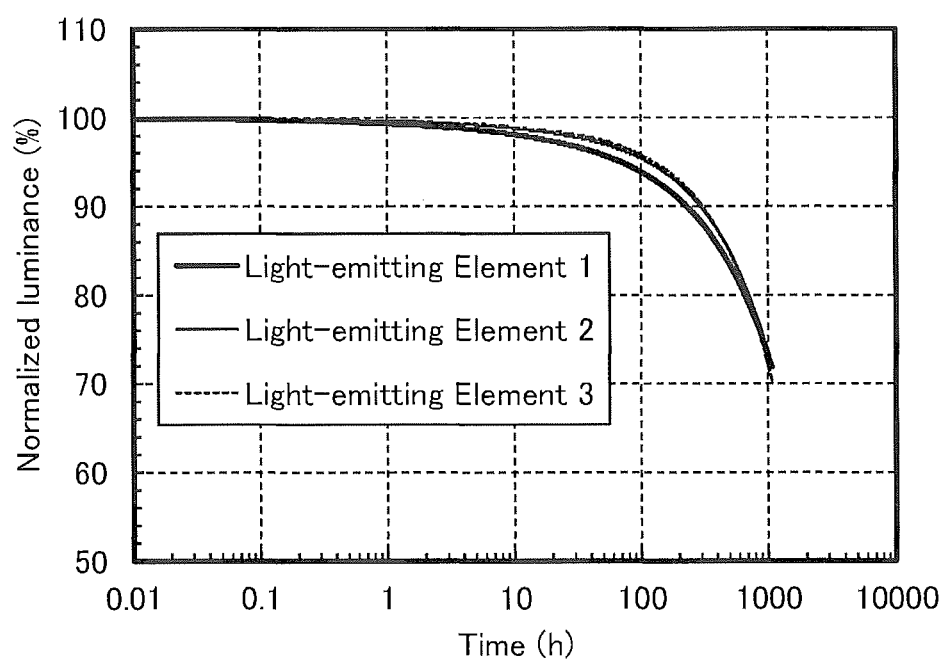
FIG. 24 shows the reliability of the light-emitting element 1, the light-emitting element 2, and the light-emitting element 3.

Next, reliability tests were performed on the light-emitting elements. FIG. 24 shows results of the reliability tests. In FIG. 24, the vertical axis represents normalized luminance (%) with an initial luminance of 100%, and the horizontal axis represents driving time (h) of the elements. Note that in the reliability tests, the light-emitting elements were driven at a constant current of 2 mA.

The reliability test results show that all the light-emitting elements fabricated in this example have excellent element characteristics.

Each of the light-emitting elements shown in this example has a structure in which an exciplex is formed in the light-emitting layer and light emission can be obtained by energy transfer from the exciplex to an emission substance, [Ir(ppy)$_2$(4dppy)] (ExTET structure). In that structure, 8Tp-4mDBtPBfpm, 8FL-4mDBtPBfpm, and 8βN-4mDBtPBfpm of embodiments of the present invention, which are used in this example, are suitable for forming an exciplex because they each have a benzofuropyrimidine skeleton and a deep LUMO level. Thus, the light-emitting elements shown in this example are also characterized by providing light emission due to ExTET and being driven at low voltage.

Example 5

Described in this example are structures, fabrication methods, and characteristics of a light-emitting element 4 of one embodiment of the present invention and a comparative light-emitting element 5. The light-emitting element 4 uses for a light-emitting layer 8βN-4mDBtPBfpm (Structural Formula (102)) described in Example 3. The comparative light-emitting element 5 uses for a light-emitting layer a comparative organic compound, 4,8-bis[3-(dibenzothiophen-4-yl)phenyl]-[1]benzofuro[3,2-d]pyrimidine (abbreviation: 4,8mDBtP2Bfpm) (Structural Formula (200)). The light-emitting elements in this example have the structure illustrated in FIG. 18. Table 3 shows specific structures of the light-emitting elements. Chemical formulae of materials used in this example are shown below.

[Chemical Formula 34]

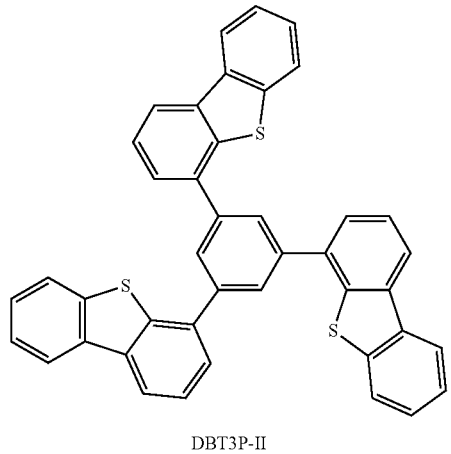

DBT3P-II

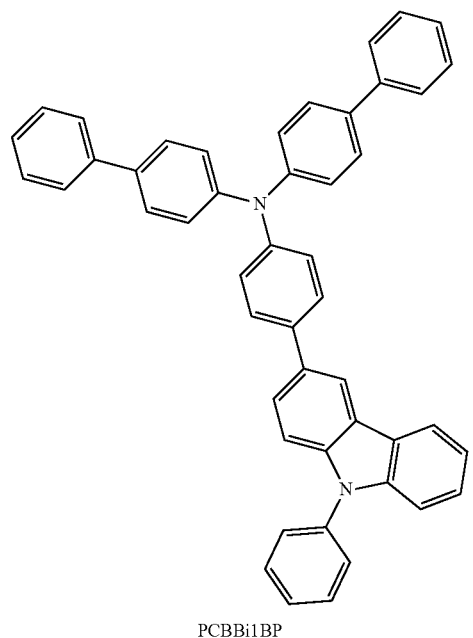

PCBBi1BP

TABLE 3

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 4 | ITSO (70 nm) | DBT3P-II:MoOx (2:1 50 nm) | PCBBi1BP (20 nm) | * | 8βN-4mDBtPBfpm (20 nm) | BPhen (15 nm) | LiF (1 nm) | Al (200 nm) |
| Comparative light-emitting element 5 | ITSO (70 nm) | DBT3P-II:MoOx (2:1 50 nm) | PCBBi1BP (20 nm) | ** | 4,8mDBtP2Bfpm (20 nm) | BPhen (15 nm) | LiF (1 nm) | Al (200 nm) |

* 8βN-4mDBtPBfpm:PCCP:Ir(ppy)$_2$(4dppy) (0.6:0.4:0.1 40 nm)
** 4,8mDBtP2Bfpm:PCCP:Ir(ppy)$_2$(4dppy) (0.6:0.4:0.1 40 nm)

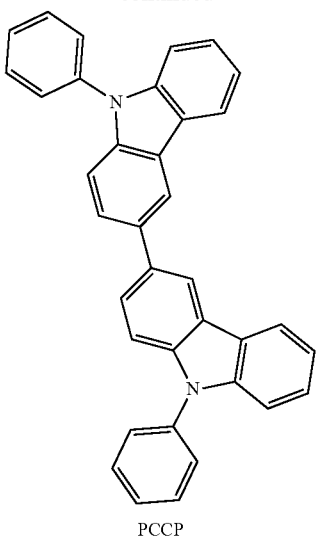

PCCP (102)

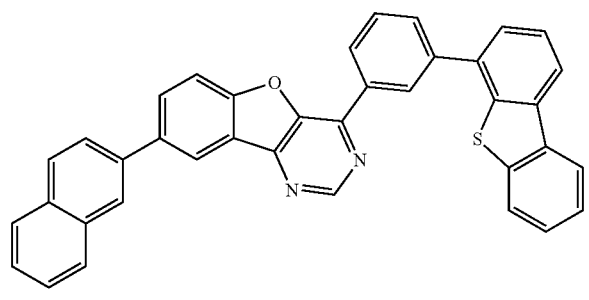

8βN-4mDBtPBfpm (200)

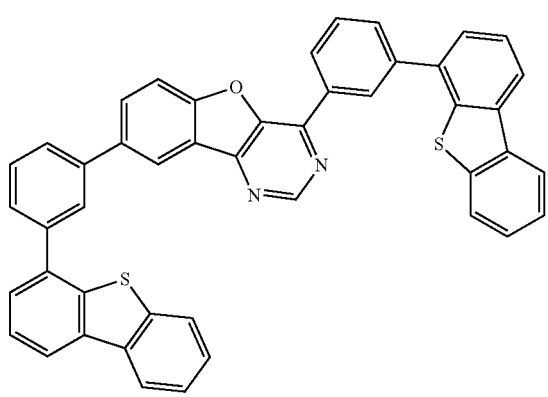

4,8mDBtP2Bfpm

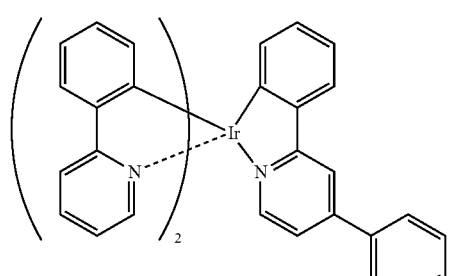

[Ir(ppy)₂(4dppy)]

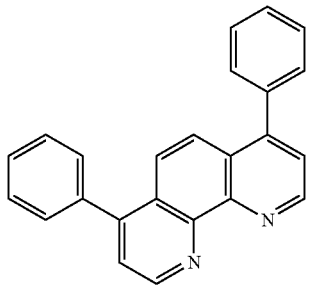

Bphen

<<Fabrication of Light-Emitting Elements>>

In each of the light-emitting elements described in this example, as illustrated in FIG. 18, the hole-injection layer 911, the hole-transport layer 912, the light-emitting layer 913, the electron-transport layer 914, and the electron-injection layer 915 are stacked in this order over the first electrode 901 formed over the substrate 900, and the second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately $10^{-4}$ Pa, and was subjected to vacuum baking at 170° C. for 60 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to $10^{-4}$ Pa, the hole-injection layer 911 was formed by co-evaporation to have a mass ratio of DBT3P-II to molybdenum oxide of 2:1 and a thickness of 50 nm.

Then, the hole-transport layer 912 was formed over the hole-injection layer 911. The hole-transport layer 912 was formed to a thickness of 20 nm by evaporation of PCBBi1BP.

Next, the light-emitting layer 913 was formed over the hole-transport layer 912.

The light-emitting layer 913 in the light-emitting element 4 was formed by co-evaporation using 8βN-4mDBtPBfpm as a host material, using PCCP as an assist material, and using [Ir(ppy)₂(4dppy)] as a guest material (a phosphorescent material) to have a weight ratio of 8βN-4mDBtPBfpm to PCCP and [Ir(ppy)₂(4dppy)] of 0.6:0.4:0.1. The thickness was set to 40 nm.

The light-emitting layer 913 in the comparative light-emitting element 5 was formed by co-evaporation using 4,8mDBtP2Bfpm as a host material, using PCCP as an assist material, and using [Ir(ppy)₂(4dppy)] as a guest material (a phosphorescent material) to have a weight ratio of 4,8mDBtP2Bfpm to PCCP and [Ir(ppy)₂(4dppy)] of 0.6:0.4:0.1. The thickness was set to 40 nm.

Next, the electron-transport layer 914 was formed over the light-emitting layer 913. The electron-transport layer 914 in the light-emitting element 4 was formed by evaporation of 8βN-4mDBtPBfpm and then BPhen to a thickness of 20 nm and 15 nm, respectively. The electron-transport layer 914 in the comparative light-emitting element 5 was formed by evaporation of 4,8mDBtP2Bfpm and then BPhen to a thickness of 20 nm and 15 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting elements each including the EL layer between a pair of electrodes were formed over the substrate 900. Note that the hole-injection layer 911, the hole-transport layer 912, the light-emitting layer 913, the electron-transport layer 914, and the electron-injection layer 915 described in the above steps are functional layers forming the EL layer in one embodiment of the present invention. Furthermore, in all the evaporation steps in the above fabrication method, evaporation was performed by a resistance-heating method.

Each of the light-emitting elements fabricated as described above was sealed using another substrate (not illustrated) in the following manner. In a glove box containing a nitrogen atmosphere, a sealant was applied so as to surround the light-emitting element formed over the substrate 900, the substrate (not illustrated) provided with a desiccant was made to overlap with a desired position over the substrate 900, and then irradiation with 365 nm ultraviolet light at 6 J/cm$^2$ was performed.

<<Operation Characteristics of Light-Emitting Elements>>

Figure 25:
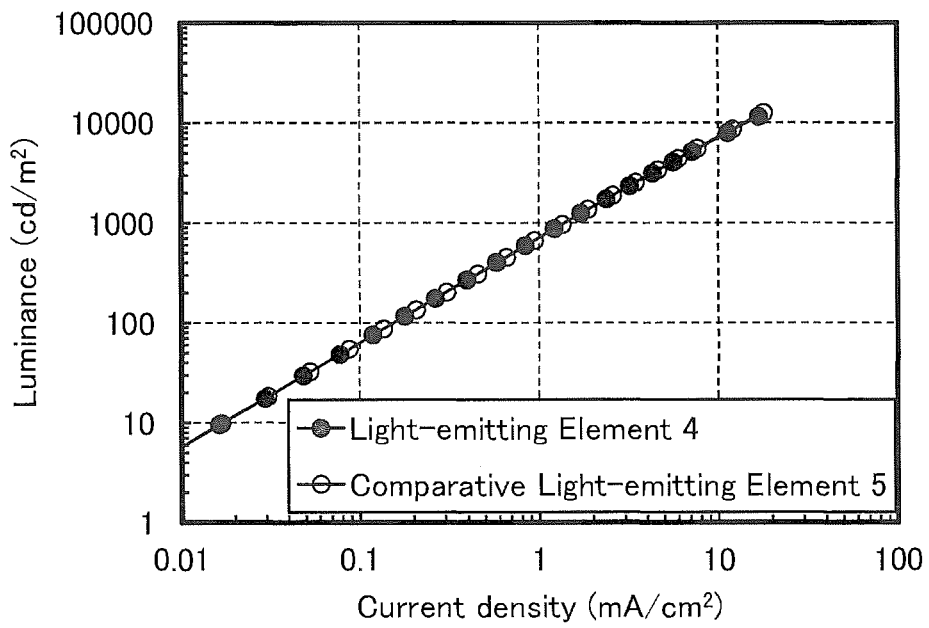
FIG. 25 shows current density-luminance characteristics of a light-emitting element 4 and a comparative light-emitting element 5.
Figure 26:
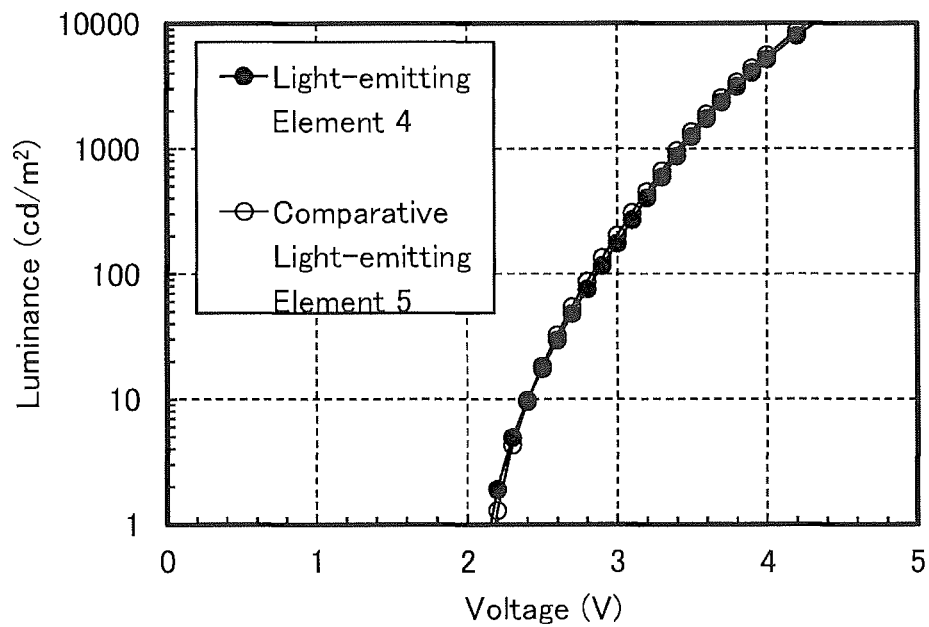
FIG. 26 shows voltage-luminance characteristics of the light-emitting element 4 and the comparative light-emitting element 5.
Figure 27:
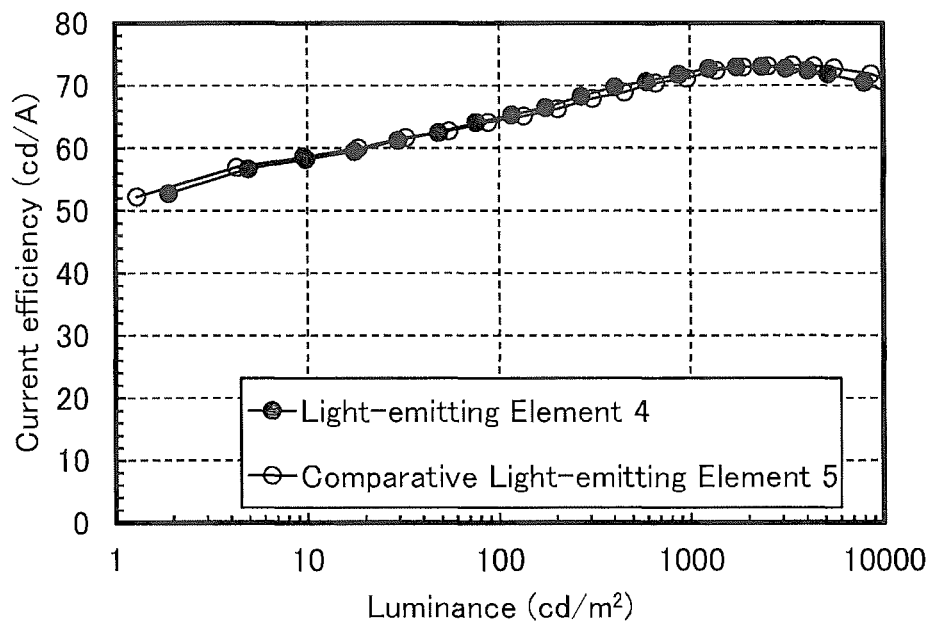
FIG. 27 shows luminance-current efficiency characteristics of the light-emitting element 4 and the comparative light-emitting element 5.
Figure 28:
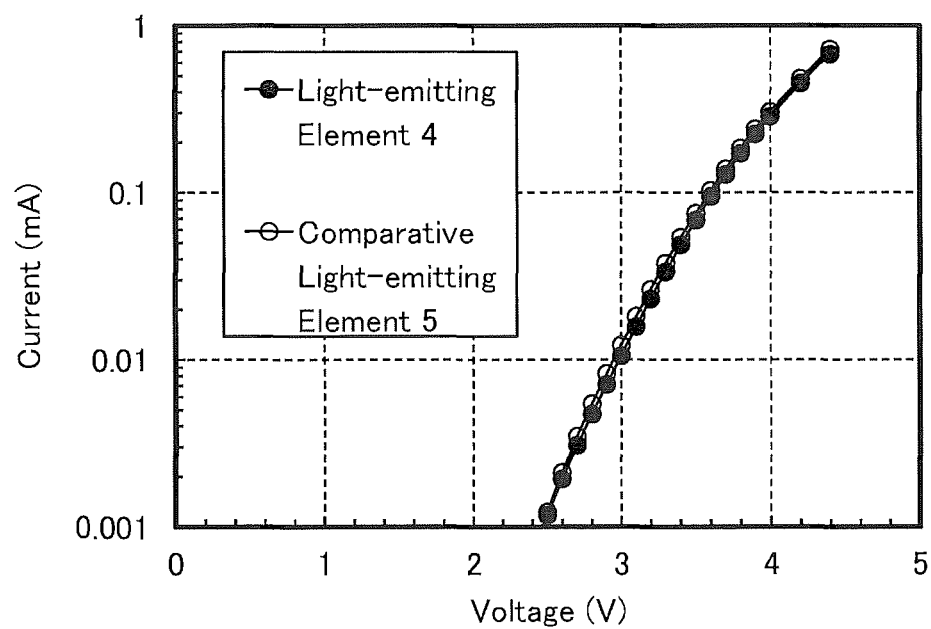
FIG. 28 shows voltage-current characteristics of the light-emitting element 4 and the comparative light-emitting element 5.

Operation characteristics of the fabricated light-emitting element 4 and comparative light-emitting element 5 were measured. Note that the measurement was performed at room temperature (in an atmosphere kept at 25° C.). As the results of the operation characteristics of the light-emitting element 4 and the comparative light-emitting element 5, the current density-luminance characteristics are shown in FIG. 25, the voltage-luminance characteristics are shown in FIG. 26, the luminance-current efficiency characteristics are shown in FIG. 27, and the voltage-current characteristics are shown in FIG. 28.

Table 4 shows initial values of main characteristics of the light-emitting element 4 and the comparative light-emitting element 5 at around 1000 cd/m$^2$.

The above results show that the light-emitting element 4 fabricated in this example have excellent element characteristics.

Figure 29:
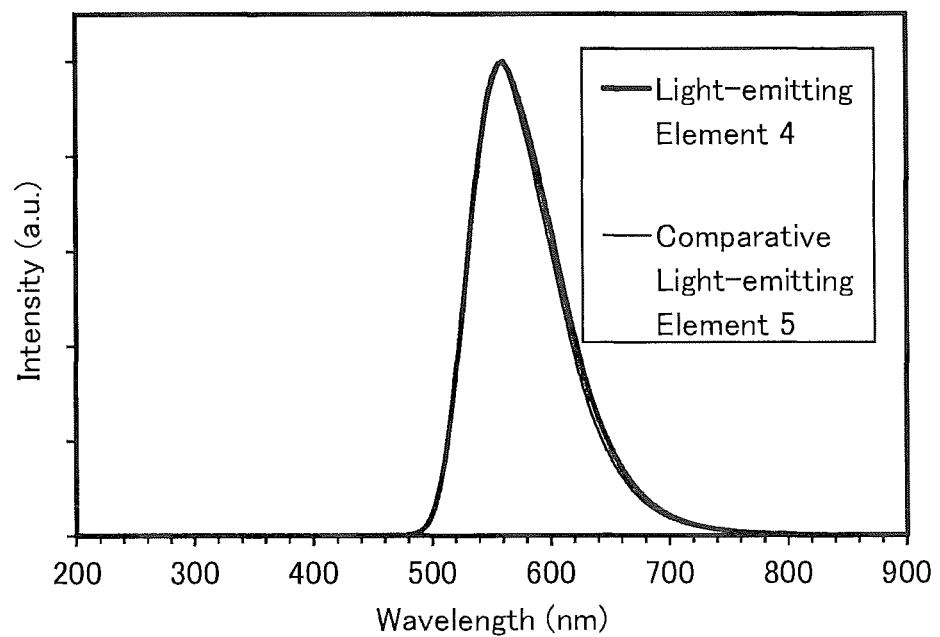
FIG. 29 shows emission spectra of the light-emitting element 4 and the comparative light-emitting element 5.

FIG. 29 shows emission spectra when current at a current density of 2.5 mA/cm$^2$ was applied to the light-emitting element 4 and the comparative light-emitting element 5. As shown in FIG. 29, the emission spectrum of each light-emitting element has a peak at around 560 nm, which is probably derived from light emission of [Ir(ppy)$_2$(4dppy)] contained in the light-emitting layer 913.

Figure 30:
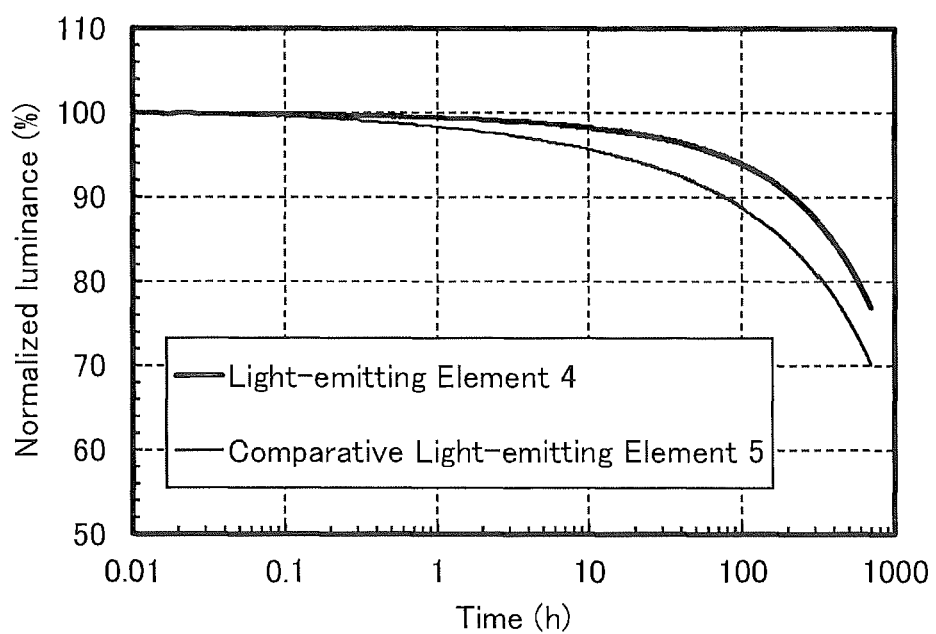
FIG. 30 shows the reliability of the light-emitting element 4 and the comparative light-emitting element 5.

Next, reliability tests were performed on the light-emitting element 4 and the comparative light-emitting element 5. FIG. 30 shows results of the reliability tests. In FIG. 30, the vertical axis represents normalized luminance (%) with an initial luminance of 100%, and the horizontal axis represents driving time (h) of the elements. Note that in the reliability tests, the light-emitting elements were driven at a constant current of 2 mA.

The reliability test results show that the light-emitting element 4 of one embodiment of the present invention has higher reliability than the comparative light-emitting element 5. Specifically, when the time (LT$_{90}$) taken for the luminance to decay to 90% of the initial luminance is compared, the LT$_{90}$ of the light-emitting element 4 is 215 hours and that of the comparative light-emitting element 5 is 78 hours, meaning that the lifetime of the light-emitting element 4 is approximately 2.8 times as long as that of the comparative light-emitting element 5. This indicates that the use of 8βN-4mDBtPBfpm (Structural Formula (102)), which is the organic compound of one embodiment of the present invention, is effective in increasing the lifetime of a light-emitting element. The results in this example also show that the condensed ring directly bonded to a benzene side of the benzofuropyrimidine skeleton or the benzothienopyrimidine skeleton directly contributes to increased lifetime of a light-emitting element.

Example 6

Synthesis Example 4

Described in this synthesis example is a method for synthesizing 8-(dibenzothiophen-4-yl)-2-[3-(dibenzothiophen-4-yl)phenyl]-[1]benzofuro[3,2-d]pyrimidine (abbreviation: 8DBt-2mDBtPBfpm), which is the organic compound of one embodiment of the present invention represented by Structural Formula (145) in Embodiment 1. Note that the structure of 8DBt-2mDBtPBfpm is shown below.

TABLE 4

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 4 | 3.4 | 0.054 | 1.3 | (0.44, 0.55) | 960 | 71 | 66 | 21 |
| Comparative light-emitting element 5 | 3.4 | 0.049 | 1.2 | (0.45, 0.54) | 870 | 72 | 66 | 21 |

[Chemical Formula 35]

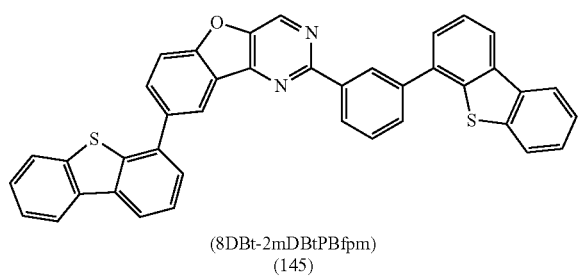

(8DBt-2mDBtPBfpm)
(145)

Step 1: Synthesis of
2-chloro-4-(dibenzothiophen-4-yl)phenol

First, 3.4 g of 4-dibenzothiophen boronic acid, 0.18 g of tris(2-methylphenyl)phosphine (abbreviation: P(o-tolyl)$_3$), 4.1 g of potassium carbonate, 56 mL of toluene, 19 mL of ethanol, and 15 ml of water were put into a three-neck flask, and degassed by being stirred with a reduced pressure. Then, the air in the flask was replaced with nitrogen. To this mixture were added 3.1 g of 4-bromo-2-chlorophenol and 67 mg of palladium(II) acetate (abbreviation: Pd(OAc)$_2$), and the mixture was stirred at 90° C. for 14 hours. After a predetermined time elapsed, water was added to the mixture and extraction with ethyl acetate was performed. The obtained organic layer was washed with water and a saturated aqueous solution of sodium chloride, and dried with magnesium sulfate. The mixture was filtered, and the obtained filtrate was concentrated to give a brown oily substance. The oily substance was dissolved in toluene and purified by silica gel column chromatography using hexane and ethyl acetate. During the purification, the proportion of hexane was gradually decreased so that the ratio of hexane to ethyl acetate changed from 5:1 to 2:1 at the end, whereby 4.3 g of a target pale yellow solid was obtained in a yield of 91%. Synthesis Scheme (d-1) of Step 1 is shown below.

[Chemical Formula 36]

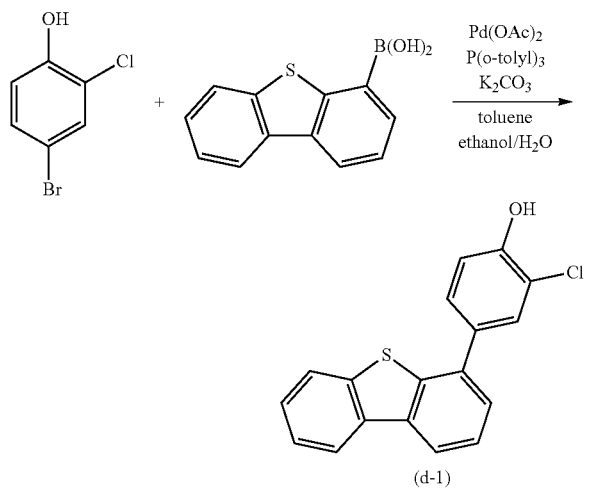

(d-1)

Step 2: Synthesis of 4-(dibenzothiophen-4-yl)-2-(4, 4,5,5-tetramethyl-1,3,2-dioxaborolan-2-yl)phenol Next, 0.31 g of 2-chloro-4-(dibenzothiophen-4-yl)phenol that was synthesized in Step 1, 0.28 g of bis(pinacolato) diboron, 0.30 g of potassium acetate (AcOK), 17 mg of 2-dicyclohexylphosphino-2',6'-dimethoxybiphenyl (S-Phos), and 2.5 mL of 1,4-dioxane were put into a two-neck flask, and degassed by being stirred with a reduced pressure. Then, the air in the flask was replaced with nitrogen.

To this mixture was added 18 mg of tris(dibenzylideneacetone)dipalladium(0) (abbreviation: Pd$_2$(dba)$_3$), and the resulting mixture was stirred at 100° C. for 7 hours. After a predetermined time elapsed, water was added to the mixture and extraction with ethyl acetate was performed. The obtained organic layer was washed with water and a saturated aqueous solution of sodium chloride, and dried with magnesium sulfate. The mixture was gravity-filtered and the filtrate was concentrated to give a brown oily substance. The oily substance was dissolved in toluene and purified by silica gel column chromatography using hexane and ethyl acetate (5:1) as a developing solvent, whereby 0.20 g of a target pale yellow solid was obtained in a yield of 50%. Synthesis Scheme (d-2) of Step 2 is shown below.

[Chemical Formula 37]

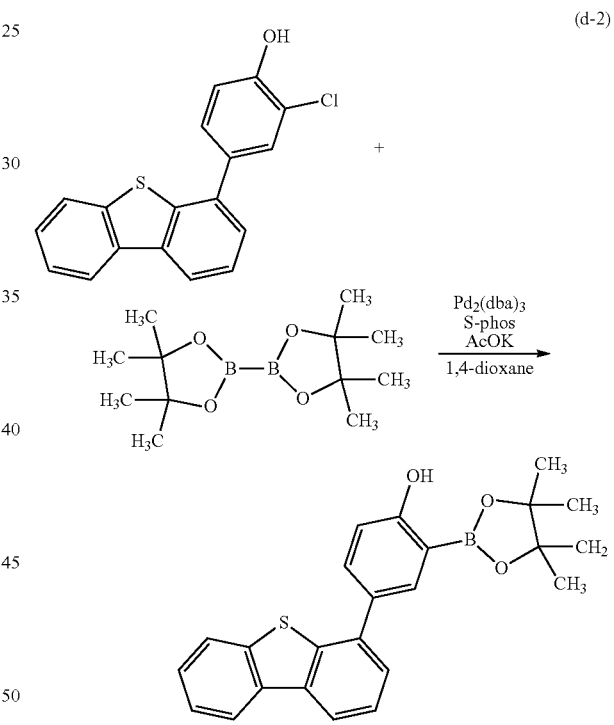

(d-2)

Step 3: Synthesis of 2,5-dichloro-4-[2-hydroxy-5-(dibenzothiophen-4-yl)phenyl]pyrimidine Next, 0.21 g of 4-(dibenzothiophen-4-yl)-2-(4,4,5,5-tetramethyl-1,3,2-dioxaborolan-2-yl)phenol that was synthesized in Step 2, 13 mg of triphenylphosphine, 0.10 g of potassium acetate, 1.9 mL of acetonitrile, and 0.48 mL of water were put into a three-neck flask, and degassed by being stirred with a reduced pressure. Then, the air in the flask was replaced with nitrogen. To this mixture were added 62 µL of 2,4,5-trichloropyrimidine and 7.0 mg of palladium (II) acetate, and the resulting mixture was stirred at room temperature for 18 hours. After a predetermined time elapsed, water was added to the mixture and extraction with ethyl acetate was performed. The obtained organic layer was washed with water and a saturated aqueous solution of sodium chloride, and dried with magnesium sulfate. The mixture was gravity-filtered, and the obtained filtrate was concentrated to give a brown oily substance. The oily substance was dissolved in toluene and purified by silica gel column chromatography using hexane and ethyl acetate (5:1) as a developing solvent, whereby 0.12 g of a target pale yellow solid was obtained in a yield of 55%. Synthesis Scheme (d-3) of Step 3 is shown below.

[Chemical Formula 38]

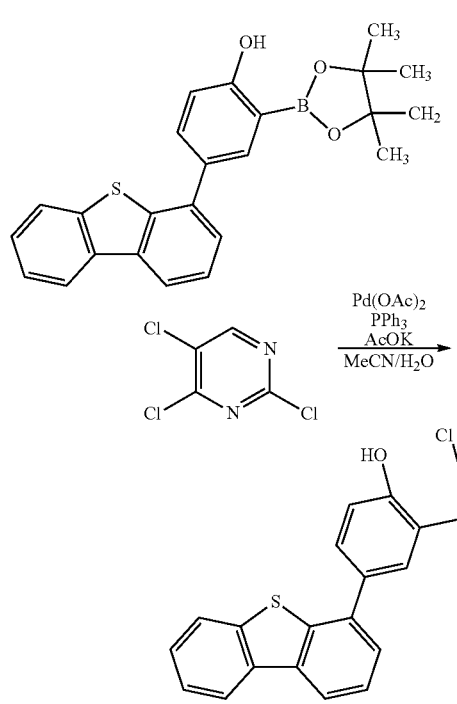

Step 4: Synthesis of 2-chloro-8-(dibenzothiophen-4-yl)-[1]benzofuro[3,2-d]pyrimidine Next, 0.36 g of 2,5-dichloro-4-[2-hydroxy-5-(dibenzothiophen-4-yl)phenyl]pyrimidine that was synthesized in Step 3, and 34 mL of dimethylacetamide (abbreviation: DMAC) were put into a two-neck flask, and degassed by being stirred with a reduced pressure. Then, the air in the flask was replaced with nitrogen. To this mixture was added 0.21 mg of copper(I) thiophene-2-carboxylate (abbreviation: CuTC), and the resulting mixture was stirred at 80° C. for 9.5 hours.

After a predetermined time elapsed, a sodium chloride solution was added to the mixture and extraction with ethyl acetate was performed. The obtained organic layer was washed with water and a saturated aqueous solution of sodium chloride, and dried with magnesium sulfate. The mixture was gravity-filtered and the filtrate was concentrated to give a yellow solid. The solid was dissolved in toluene and purified by silica gel column chromatography using hexane and ethyl acetate (5:1) as a developing solvent, whereby 0.16 g of a target white solid was obtained in a yield of 50%. Synthesis Scheme (d-4) of Step 4 is shown below.

[Chemical Formula 39]

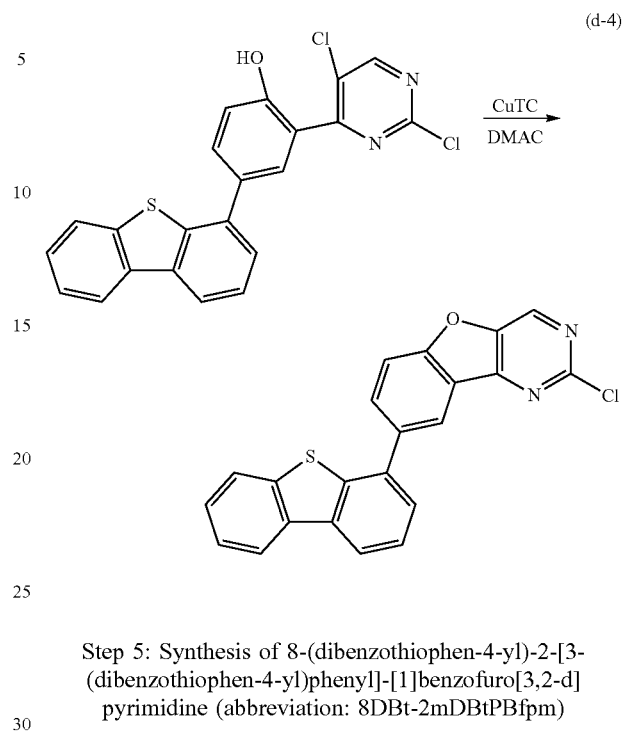

Step 5: Synthesis of 8-(dibenzothiophen-4-yl)-2-[3-(dibenzothiophen-4-yl)phenyl]-[1]benzofuro[3,2-d]pyrimidine (abbreviation: 8DBt-2mDBtPBfpm)

Next, 0.10 g of 2-chloro-8-(dibenzothiophen-4-yl)-[1]benzofuro[3,2-d]pyrimidine that was synthesized in Step 4, 99 mg of 3-(dibenzothiophen-4-yl)phenylboronic acid, 0.17 g of tripotassium phosphate, 2.7 mL of diglyme, and 6.7 mg of t-butanol were put into a three-neck flask, and degassed by being stirred with a reduced pressure. Then, the air in the flask was replaced with nitrogen. To this mixture were added 1.9 mg of palladium(II) acetate and 6.0 mg of di(1-adamantyl)-n-butylphosphine, and the resulting mixture was stirred under a nitrogen stream at 120° C. for 7.5 hours, and then at 140° C. for 1.5 hours. After a predetermined time elapsed, water was added to the mixture, the precipitate was subjected to suction filtration, and the residue was washed with ethanol.

The obtained residue was dissolved in heated toluene and filtered through a filter aid filled with Celite, alumina, and Celite in this order. The obtained solution was concentrated and dried, and then recrystallized with toluene to give 0.040 g of a white solid, 8DBt-2mDBtPBfpm (abbreviation) of the present invention, in a yield of 24%. Synthesis Scheme (d-5) of Step 5 is shown below.

[Chemical Formula 40]

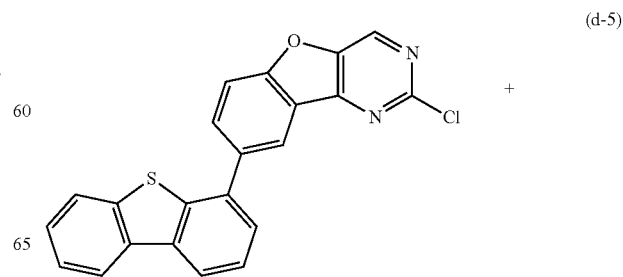

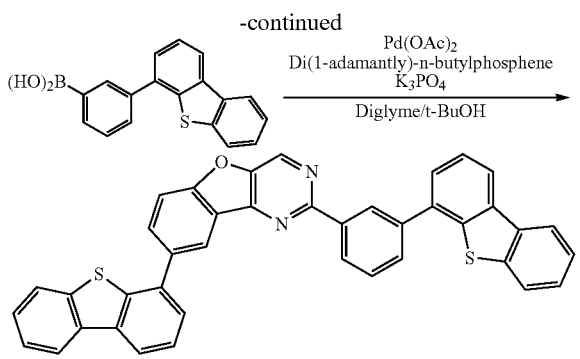

Analysis results by nuclear magnetic resonance ($^1$H-NMR) spectroscopy of the obtained white solid are shown below. The results reveal that 8DBt-2mDBtPBfpm, the organic compound represented by Structural Formula (145), was obtained in this example.

$^1$H-NMR. δ (CDCl$_3$): 7.42-7.52 (m, 4H), 7.59 (t, 3H), 7.64 (d, 1H), 7.69 (t, 1H), 7.82-7.85 (m, 3H), 7.90 (d, 1H), 8.12 (dd, 1H), 8.18-8.23 (m, 4H), 8.68 (dt, 1H), 8.70 (sd, 1H), 8.99 (st, 1H), 9.16 (s, 1H).

Reference Synthesis Example

Described in this reference synthesis example is a method for synthesizing 4,8-bis[3-(dibenzothiophen-4-yl)phenyl]-[1]benzofuro[3,2-d]pyrimidine (abbreviation: 4,8mDBtP2Bfpm) (Structural Formula (200)), which is the benzofuropyrimidine compound described in Example 5. Note that the structure of 4,8mDBtP2Bfpm is shown below.

[Chemical Formula 41]

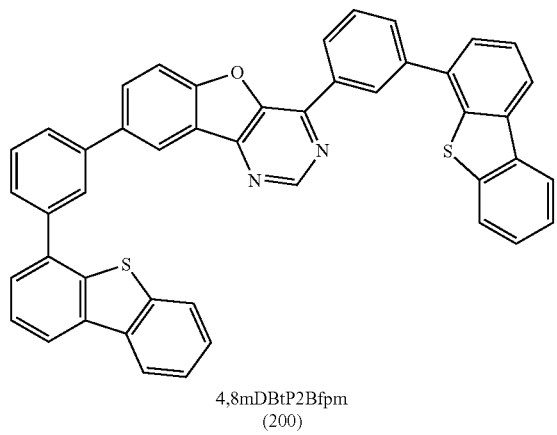

4,8mDBtP2Bfpm
(200)

Step 1: Synthesis of 8-chloro-4-[3-(dibenzothiophen-4-yl)phenyl]-[1]benzofuro[3,2-d]pyrimidine First, 1.0 g of 4,8-dichloro[1]benzofuro[3,2-d]pyrimidine, 2.6 g of 3-(dibenzothiophen-4-yl)phenylboronic acid, 1.2 g of potassium carbonate, 42 mL of toluene, 4 mL of ethanol, and 4 mL of water were put into a three-neck flask equipped with a reflux pipe. The air in the flask was replaced with nitrogen, 0.29 g of bis(triphenylphosphine)palladium(II) dichloride (abbreviation: Pd(PPh$_3$)$_2$Cl$_2$) was added, and the mixture was heated under a nitrogen stream at 80° C. for 8 hours. The obtained reaction mixture was filtered and washed with water and ethanol, so that 1.9 g of a target substance (a gray solid) was obtained in a yield of 96%. Synthesis Scheme (A-1) of Step 1 is shown below.

[Chemical Formula 42]

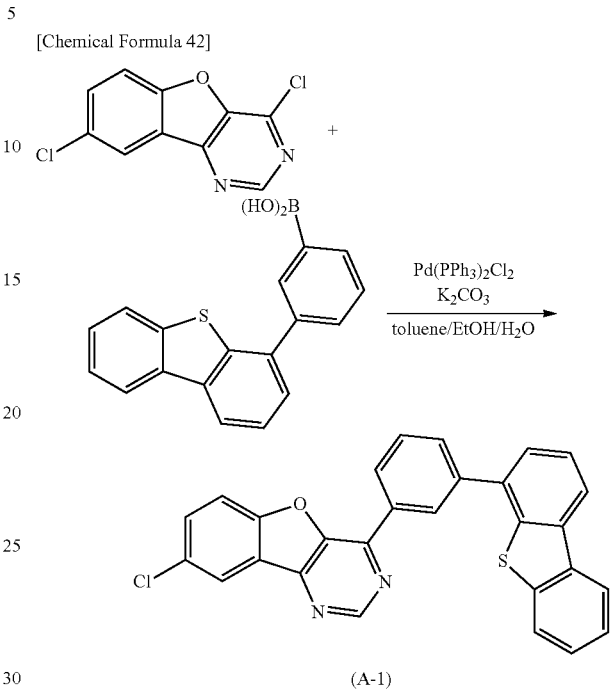

Analysis results by nuclear magnetic resonance ($^1$H-NMR) spectroscopy of the gray solid obtained in Step 1 are shown below. The results reveal that 8-chloro-4-[3-(dibenzothiophen-4-yl)phenyl]-[1]benzofuro[3,2-d]pyrimidine was obtained.

$^1$H-NMR. δ (TCE-d$_2$): 7.48-7.52 (m, 2H), 7.63-7.71 (m, 4H), 7.77-7.80 (t, 1H), 7.85 (d, 1H), 7.96 (d, 1H), 8.22-8.23 (m, 2H), 8.28 (s, 1H), 8.65 (d, 1H), 8.96 (s, 1H), 9.29 (s, 1H).

Step 2: Synthesis of 4,8-bis[3-(dibenzothiophen-4-yl)phenyl]-[1]benzofuro[3,2-d]pyrimidine (abbreviation: 4,8mDBtP2Bfpm)

Next, 1.7 g of 8-chloro-4-[3-(dibenzothiophen-4-yl)phenyl]-[1]benzofuro[3,2-d]pyrimidine synthesized in Step 1, 1.1 g of 3-(dibenzothiophen-4-yl)phenylboronic acid, 1.6 g of potassium phosphate, and 60 mL of diethylene glycol dimethyl ether (abbreviation: diglyme) were put into a flask. The air in the flask was replaced with nitrogen, 90 mg of palladium acetate and 0.29 g of di(1-adamantyl)-n-butylphosphine were added, and the mixture was heated under a nitrogen stream at 160° C. for 12 hours. The obtained reaction mixture was filtered, washed with water and then with ethanol. The obtained residue was filtered through a filter aid filled with Celite, aluminum oxide, and Celite in this order. The resulting solution was recrystallized, whereby 1.2 g of 4,8mDBtP2Bfpm was obtained in a yield of 47% (a yellowish white solid). By a train sublimation method, 1.2 g of the obtained yellowish white solid was purified by sublimation. In the purification by sublimation, the solid was heated at 330° C. under a pressure of 2.6 Pa with an argon gas flow rate of 5 mL/min. After the purification by sublimation, 0.8 g of a target yellowish white solid was obtained at a collection rate of 67%. Synthesis Scheme (A-2) of Step 2 is shown below.

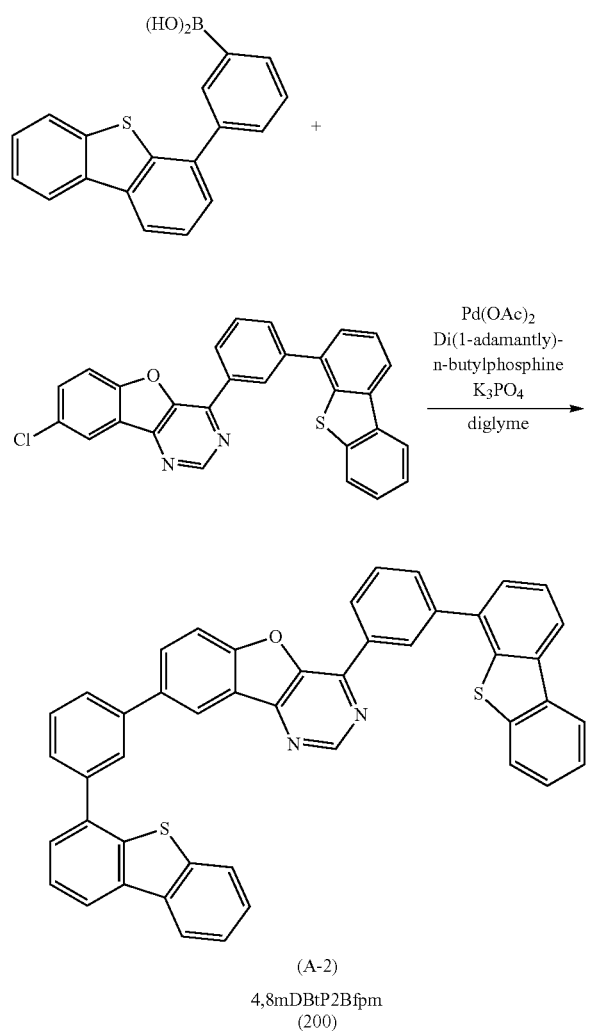

(A-2)
4,8mDBtP2Bfpm
(200)

Analysis results by nuclear magnetic resonance ($^1$H-NMR) spectroscopy of the yellowish white solid obtained in Step 2 are shown below. The results reveal that 4,8mDBtP2Bfpm was obtained.

$^1$H-NMR. δ (TCE-$d_2$): 7.48-7.52 (t, 4H), 7.60 (s, 1H), 7.61 (d, 1H), 7.65-7.69 (m, 3H), 7.79-7.83 (m, 3H), 7.86-7.89 (m, 3H), 8.00 (d, 1H), 8.07 (s, 1H), 8.10 (d, 1H), 8.19-8.24 (m, 4H), 8.69-8.72 (t, 2H), 9.02 (s, 1H), 9.32 (s, 1H).

Example 7

Synthesis Example 5

Described in this synthesis example is a method for synthesizing 4-[3-(dibenzothiophen-4-yl)phenyl]-8-(naphthalen-1-yl)-[1]benzofuro[3,2-d]pyrimidine (abbreviation: 8αN-4mDBtPBfpm), which is the organic compound of one embodiment of the present invention represented by Structural Formula (103) in Embodiment 1. The structure of 8αN-4mDBtPBfpm is shown below.

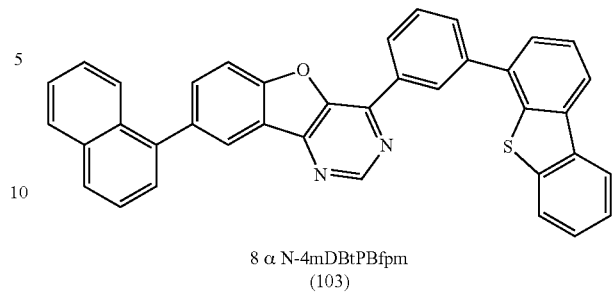

8 α N-4mDBtPBfpm
(103)

Step 1: Synthesis of 2-hydroxy-5-(naphthalen-1-yl)benzonitrile

First, 2.97 g of 6-bromo-2-hydroxybenzonitrile, 2.8 g of naphthalene-1-boronic acid, 0.184 g of tris(2-methylphenyl)phosphine (P(o-tol)$_3$), 4.15 g of potassium carbonate, 56 mL of toluene, 19 mL of ethanol, and 15 ml of water were put into a three-neck flask, and degassed by being stirred with a reduced pressure. Then, the air in the flask was replaced with nitrogen. To this mixture was added 69.3 mg of palladium (II) acetate (abbreviation: Pd(OAc)$_2$), and the mixture was stirred at 100° C. for 17.5 hours. Water was added to the obtained reaction mixture and extraction with ethyl acetate was performed. The obtained organic layer was washed with water and a saturated aqueous solution of sodium chloride, and dried with magnesium sulfate. The mixture was gravity-filtered, and the filtrate was concentrated to give a pale brown solid. The solid was dissolved in a mixed solvent of heated toluene and ethyl acetate, and purified by silica gel column chromatography using hexane and ethyl acetate as a developing solvent. During the purification, the proportion of hexane was gradually decreased so that the ratio of hexane to ethyl acetate changed from 3:1 to 1:1 at the end, whereby 3.43 g of a target pale yellow solid was obtained in a yield of 93%. Synthesis Scheme (e-1) of Step 1 is shown below.

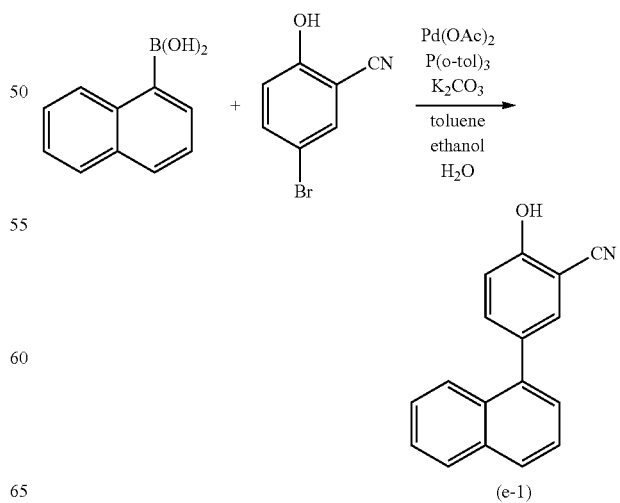

(e-1)

Step 2: Synthesis of ethyl3-amino-5-(naphthalen-1-yl)benzo[b]furan-2-carboxylate Next, 3.43 g of 2-hydroxy-5-(naphthalen-1-yl)benzonitrile synthesized in Step 1 and 3.87 g of potassium carbonate were put into a three-neck flask. The air in the flask was replaced with nitrogen. To this mixture were added 3.51 g of ethyl bromoacetate and 18 mL of N,N-dimethylformamide (abbreviation: DMF), and the mixture was stirred at 100° C. for 5 hours. The obtained reaction mixture was put into iced water, stirred for 1 hour, and subjected to suction filtration, whereby 4.97 g of a target dark brown residue was obtained. Synthesis Scheme (e-2) of Step 2 is shown below.

[Chemical Formula 46]

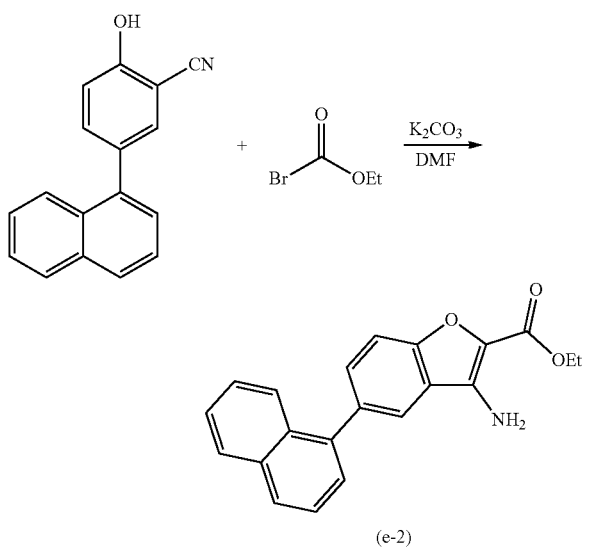

(e-2)

Step 3: Synthesis of 8-(naphthalen-1-yl)-[1]benzofuro[3,2-d]pyrimidin-4(3H)-one Into a recovery flask were put 4.97 g of the dark brown substance obtained in Step 2 and 20 mL of formamide, and the mixture was heated at 150° C. To this mixture was added 2.92 g of formamidine acetate, and the mixture was stirred at 160° C. for 6.5 hours. Water was added to the obtained reaction mixture and subjected to suction filtration to give a residue. The residue was washed with ethyl acetate and hexane, whereby 2.98 g of a target pale brown solid was obtained (the yield from Step 2 to Step 3: 68%). Synthesis Scheme (e-3) of Step 3 is shown below.

[Chemical Formula 47]

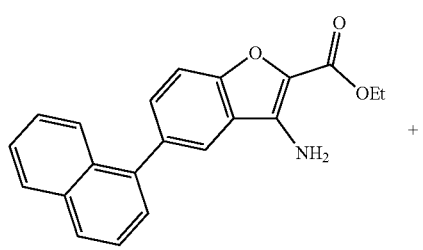

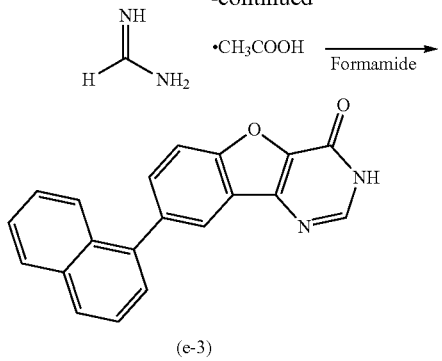

(e-3)

Step 4: Synthesis of 4-chloro-8-(naphthalen-1-yl)-[1]benzofuro[3,2-d]pyrimidine Into a three-neck flask were put 2.98 g of 8-(naphthalen-1-yl)-[1]benzofuro[3,2-d]pyrimidin-4(3H)-one synthesized in Step 3 and 74 μL of N,N-dimethylformamide (DMF), and the mixture was stirred. To this mixture was added 31.8 g of phosphoryl chloride and the mixture was stirred at 90° C. for 11 hours. Phosphoryl chloride was distilled off from the obtained reaction mixture, and the mixture was put into iced water, neutralized with a saturated aqueous solution of sodium bicarbonate, and stirred for 1 hour. The mixture was subjected to suction filtration and the residue was washed with ethanol, whereby 3.12 g of a target pale brown solid was obtained in a yield of 99%. Synthesis Scheme (e-4) of Step 4 is shown below.

[Chemical Formula 48]

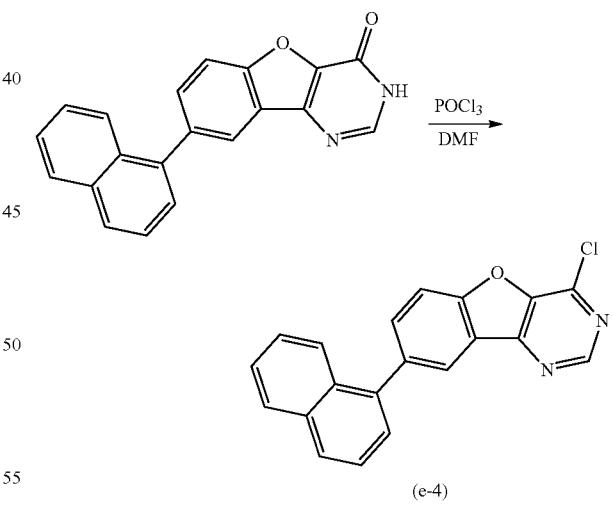

(e-4)

Step 5: Synthesis of 8αN-4mDBtPBfpm

Into a three-neck flask were put 3.12 g of 4-chloro-8-(naphthalen-1-yl)-[1]benzofuro[3,2-d]pyrimidine, 3.44 g of 3-(dibenzothiophen-4-yl)phenylboronic acid, 2.61 g of potassium carbonate, 36 mL of toluene, 12 mL of ethanol, and 9.5 ml of water. The mixture was degassed by being stirred with a reduced pressure. Then, the air in the flask was replaced with nitrogen. To this mixture was added 0.324 g of tetrakis(triphenylphosphine)palladium(II) (Pd(PPh$_4$)$_2$), and the mixture was stirred at 100° C. for 27.5 hours. Water was added to the obtained reaction mixture and subjected to suction filtration. The obtained residue was washed with water and ethyl acetate, dissolved in heated toluene, and filtered through a filter aid filled with Celite, alumina, and Celite in this order. The obtained solution was concentrated and dried, and then recrystallized with toluene to give 3.0 g of a target white solid in a yield of 57%. By a train sublimation method, 3.00 g of the white solid was purified by sublimation. In the purification by sublimation, the solid was heated at 290° C. under a pressure of 3.7 Pa with an argon gas flow rate of 15 mL/min. After the purification by sublimation, 1.86 g of a target white solid was obtained at a collection rate of 62%. Synthesis Scheme (e-5) of Step 5 is shown below.

[Chemical Formula 49]

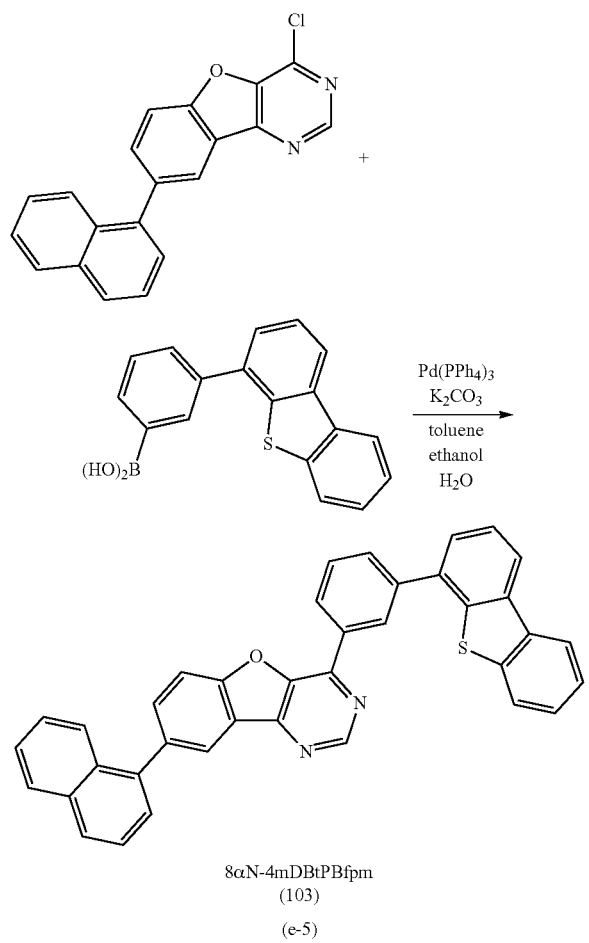

8αN-4mDBtPBfpm
(103)

(e-5)

Figure 31:
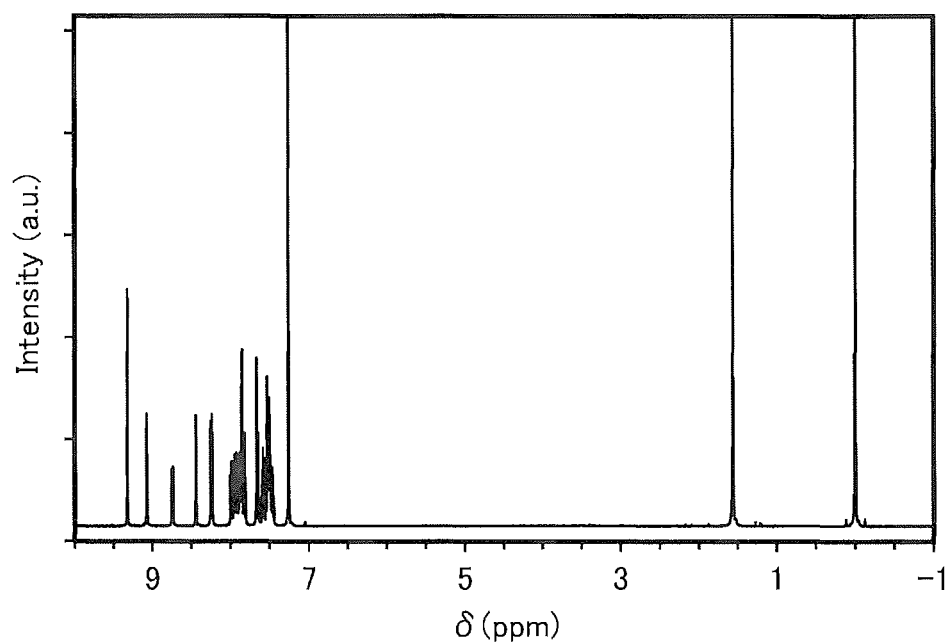
FIG. 31 is a $^1$H-NMR chart of an organic compound represented by Structural Formula (103).

Analysis results by nuclear magnetic resonance ($^1$H-NMR) spectroscopy of the white solid obtained in Step 5 are shown below. FIG. 31 is the $^1$H-NMR chart. The results reveal that 8αN-4mDBtPBfpm was obtained.

$^1$H-NMR. δ (CDCl$_3$): 7.45-7.55 (m, 5H), 7.59 (t, 1H), 7.63-7.67 (m, 2H), 7.82 (t, 1H), 7.85-8.00 (m, 7H), 8.24 (d, 2H), 8.44 (s, 1H), 8.50 (d, 1H), 9.08 (s, 1H), 9.32 (s, 1H).

Example 8

Synthesis Example 6

Described in this example is a method for synthesizing 4-[3'-(dibenzothiophen-4-yl)biphenyl-3-yl]-8-(naphthalen-2-yl)-[1]benzofuro[3,2-d]pyrimidine (abbreviation: 8βN-4mDBtBPBfpm), which is the organic compound of one embodiment of the present invention represented by Structural Formula (116) in Embodiment 1. The structural formula of 8βN-4mDBtBPBfpm is shown below.

[Chemical Formula 50]

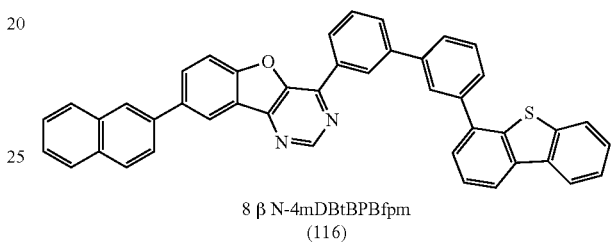

8 β N-4mDBtBPBfpm
(116)

Step 1: Synthesis of 8-chloro-4-[3'-(dibenzothiophen-4-yl)biphenyl-3-yl]-[1]benzofuro[3,2-d]pyrimidine Into a three-neck flask were put 7.65 g of 4,8-dichloro[1]benzofuro[3,2-d]pyrimidine, 17.0 g of 3'-(dibenzothiophen-4-yl)biphenyl-3-boronic acid, 12.4 g of potassium carbonate, 360 mL of toluene, 36 mL of ethanol, and 45 mL of water. The mixture was degassed by being stirred with a reduced pressure. Then, the air in the flask was replaced with nitrogen. To this mixture was added 2.25 g of bis(triphenylphosphine)palladium(II) dichloride (abbreviation: Pd(PPh$_3$)$_2$Cl$_2$) and the mixture was stirred at 80° C. for 6 hours. Water was added to the obtained reaction mixture and subjected to suction filtration. The obtained residue was washed with water and ethanol, dissolved in heated toluene, and filtered through a filter aid filled with Celite, alumina, and Celite in this order. The obtained solution was concentrated and dried, and then recrystallized with toluene to give 14.7 g of a target pale yellow solid in a yield of 85%. Synthesis Scheme (f-1) of Step 1 is shown below.

[Chemical Formula 51]

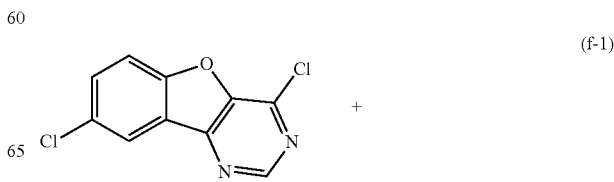

(f-1)

-continued

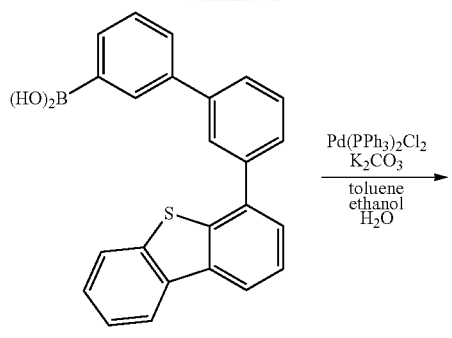

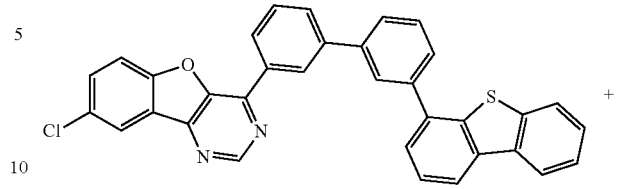

[Chemical Formula 52]

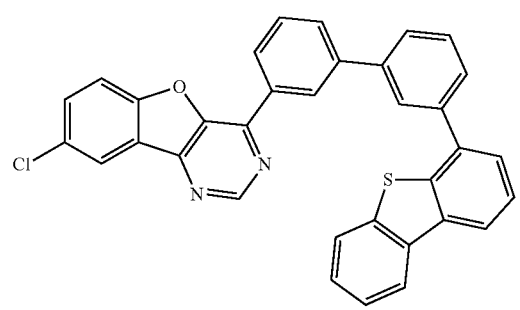

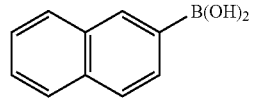
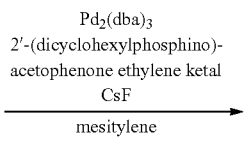

Step 2: Synthesis of 8βN-4mDBtBPBfpm

8βN-4mDBtBPBfpm
(116)

(f-2)

Next, 7.01 g of 8-chloro-4-[3'-(dibenzothiophen-4-yl)biphenyl-3-yl]-[1]benzofuro[3,2-d]pyrimidine synthesized in Step 1, 3.13 g of naphthalene-2-boronic acid, 5.93 g of cesium fluoride, and 130 mL of mesitylene were put into a three-neck flask. The mixture was degassed by being stirred with a reduced pressure. Then, the air in the flask was replaced with nitrogen. To this mixture were added 0.358 g of tris(dibenzylideneacetone)dipalladium(0) (Pd$_2$(dba)$_3$) and 0.283 g of 2'-(dicyclohexylphosphino)acetophenone ethylene ketal, and the mixture was stirred at 120° C. for 17.5 hours. To this mixture were added 0.358 g of tris(dibenzylideneacetone)dipalladium(0) and 0.283 g of 2'-(dicyclohexylphosphino)acetophenone ethylene ketal, and the mixture was stirred at 120° C. for 16 hours.

Water was added to the obtained reaction mixture and subjected to suction filtration. The obtained residue was washed with water and ethyl acetate, dissolved in heated toluene, and filtered through a filter aid filled with Celite, alumina, and Celite in this order. The obtained solution was concentrated and dried, and then recrystallized with toluene to give 6.75 g of a target white solid, 8βN-4mDBtBPBfpm (abbreviation) of the present invention, in a yield of 82%. By a train sublimation method, 2.47 g of the white solid was purified by sublimation. In the purification by sublimation, the solid was heated at 340° C. under a pressure of 3.7 Pa with an argon gas flow rate of 15 mL/min. After the purification by sublimation, 2.20 g of a target pale brown solid was obtained at a collection rate of 89%. Synthesis Scheme (f-2) of Step 2 is shown below.

Figure 32:
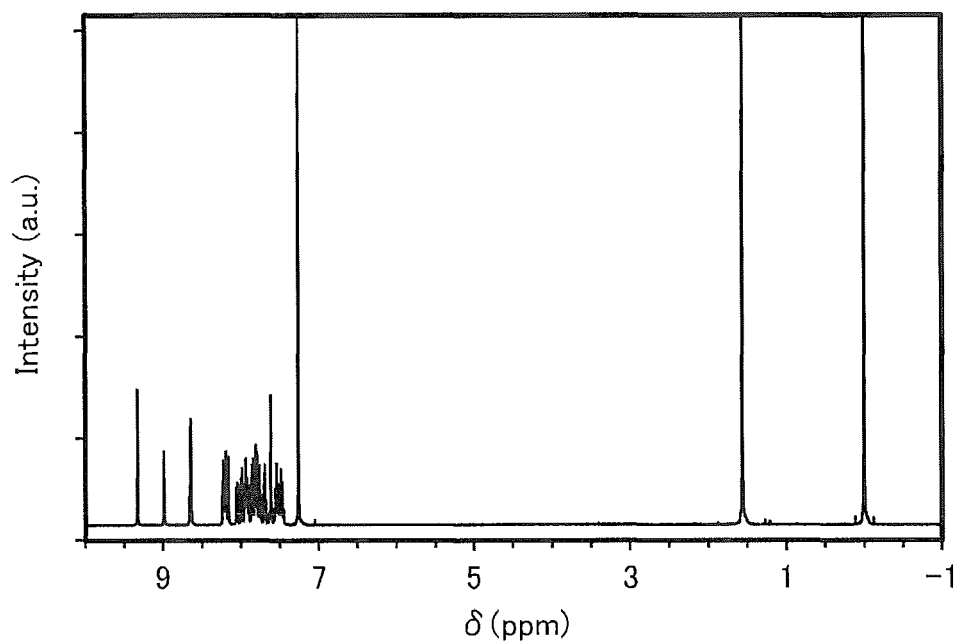
FIG. 32 is a $^1$H-NMR chart of an organic compound represented by Structural Formula (116).
Figure 33:
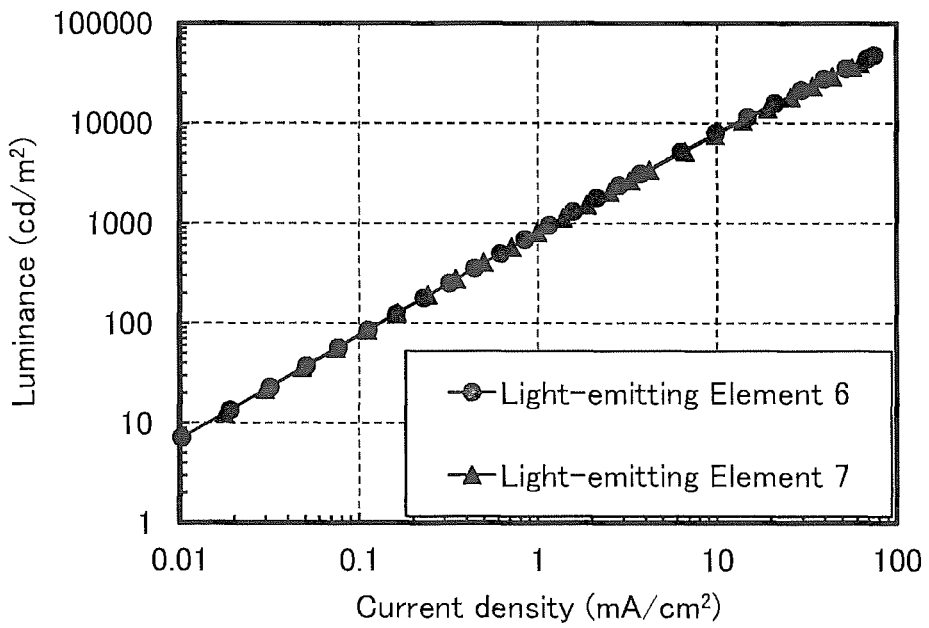
FIG. 33 shows current density-luminance characteristics of a light-emitting element 6 and a light-emitting element 7.
Figure 34:
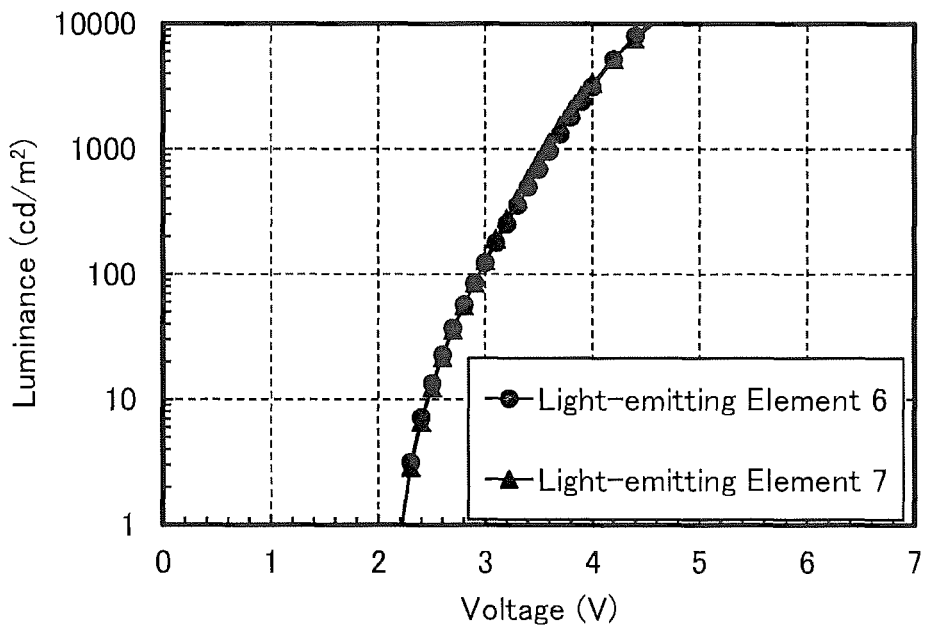
FIG. 34 shows voltage-luminance characteristics of the light-emitting element 6 and the light-emitting element 7.
Figure 35:
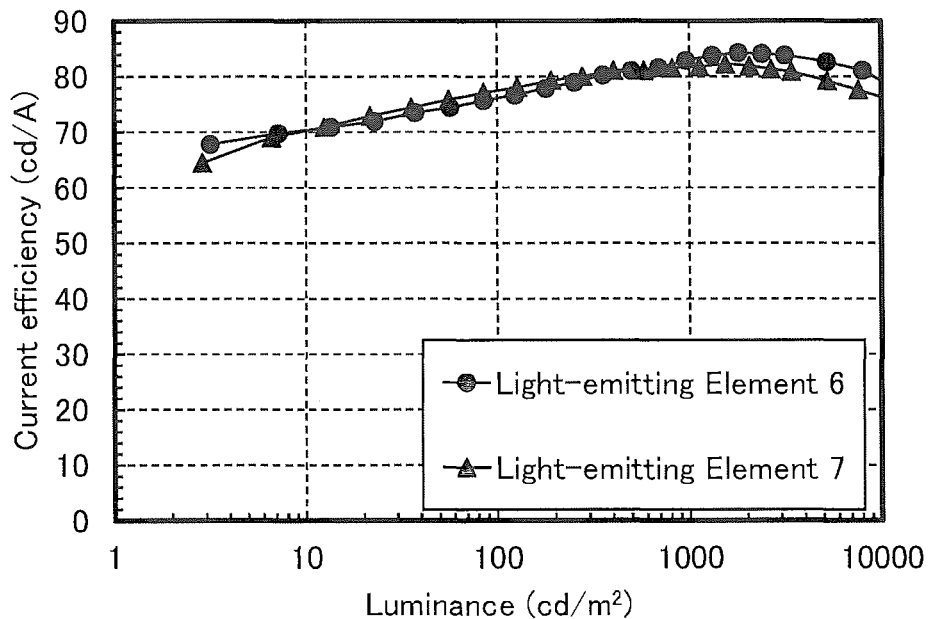
FIG. 35 shows luminance-current efficiency characteristics of the light-emitting element 6 and the light-emitting element 7.
Figure 36:
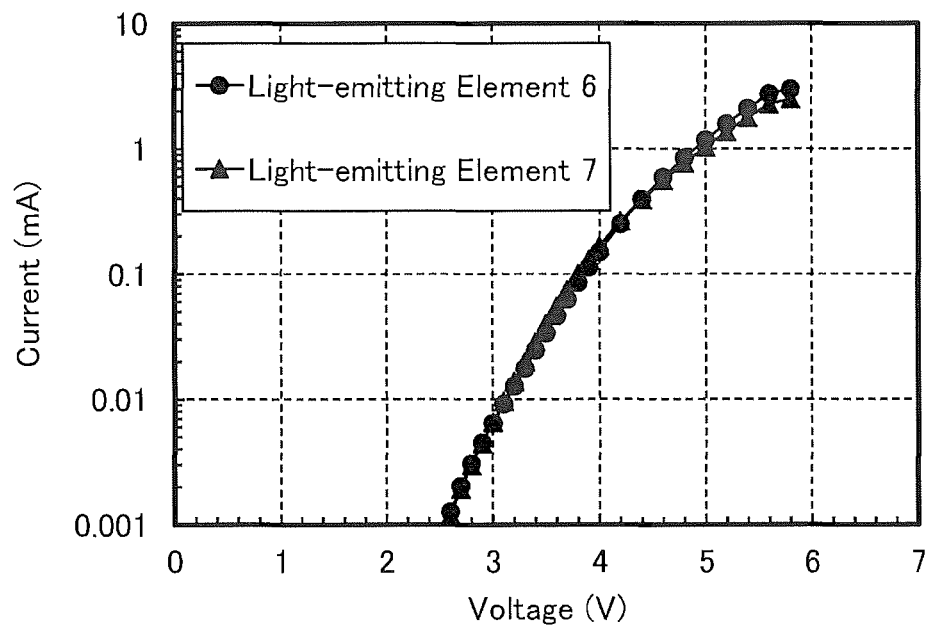
FIG. 36 shows voltage-current characteristics of the light-emitting element 6 and the light-emitting element 7.

Analysis results by nuclear magnetic resonance ($^1$H-NMR) spectroscopy of the pale brown solid obtained in Step 2 are shown below. FIG. 32 is the $^1$H-NMR chart. The results reveal that 8βN-4mDBtBPBfpm was obtained.

$^1$H-NMR. δ (CDCl$_3$): 7.46-7.57 (m, 4H), 7.61-7.63 (m, 2H), 7.70 (t, 1H), 7.76 (t, 1H), 7.79-7.83 (m, 3H), 7.86 (d, 2H), 7.91-7.95 (m, 3H), 8.00 (d, 1H), 8.05 (d, 1H), 8.18 (d, 2H), 8.21-8.24 (m, 2H), 8.65-8.66 (m, 2H), 8.99 (s, 1H), 9.33 (s, 1H).

Example 9

In this example, light-emitting elements 6 and 7 were fabricated as light-emitting elements of embodiments of the present invention. The light-emitting element 6 uses for a light-emitting layer 8αN-4mDBtPBfpm (Structural Formula (103)) described in Example 7. The light-emitting element 7 uses for a light-emitting layer 8βN-4mDBtBPBfpm (Structural Formula (116)) described in Example 8. The measured results of characteristics of the light-emitting elements 6 and 7 will be described below.

Element structures of the light-emitting elements used in this example are similar to those described in Example 4 with reference to FIG. 18. Table 5 shows specific structures of layers in the element structures. Chemical formulae of materials used in this example are shown below.

TABLE 5

| | First electrode | Hole-injection layer | Hole-transport layer | Light-emitting layer | Electron-transport layer | Electron-injection layer | Second electrode |
|---|---|---|---|---|---|---|---|
| Light-emitting element 6 | ITSO (70 nm) | DBT3P-II:MoOx (2:1 50 nm) | PCBBi1BP (20 nm) | * | 8αN-4mDBtPBfpm (20 nm) | NBPhen (15 nm) | LiF (1 nm) | Al (200 nm) |
| Light-emitting element 7 | ITSO (70 nm) | DBT3P-II:MoOx (2:1 50 nm) | PCBBi1BP (20 nm) | ** | 8βN-4mDBtBPBfpm (20 nm) | NBPhen (15 nm) | LiF (1 nm) | Al (200 nm) |

* 8αN-4mDBtPBfpm:PCCP:[Ir(ppy)$_2$(4dppy)] (0.6:0.4:0.1 40 nm)
** 8βN-4mDBtBPBfpm:PCCP:[Ir(ppy)$_2$(4dppy)] (0.6:0.4:0.1 40 nm)

15

[Chemical Formula 53]

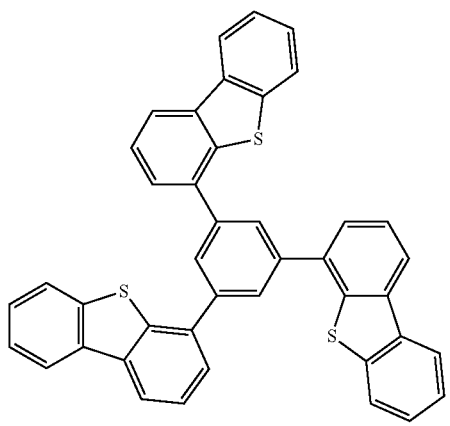

DBT3P-II

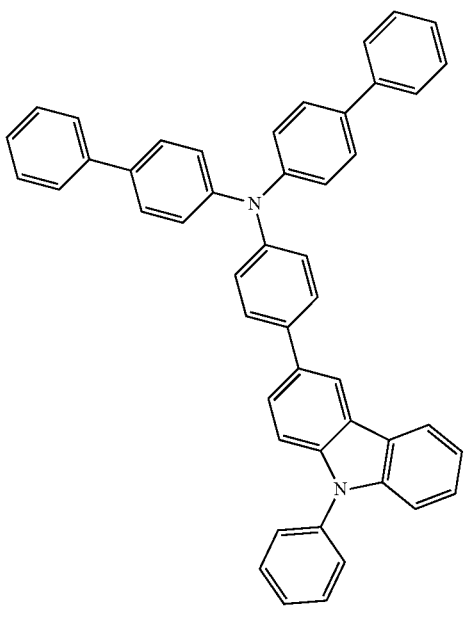

PCBBi1BP (103)

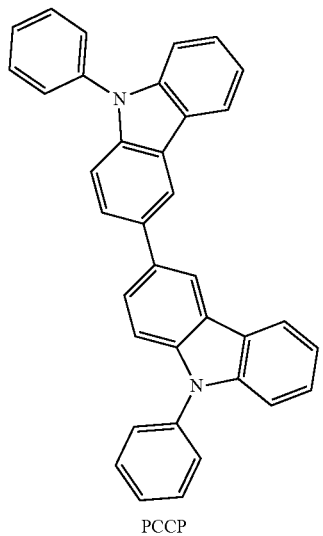

PCCP

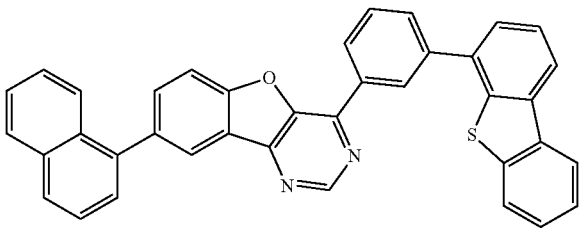

8 α N-4mDBtPBfpm

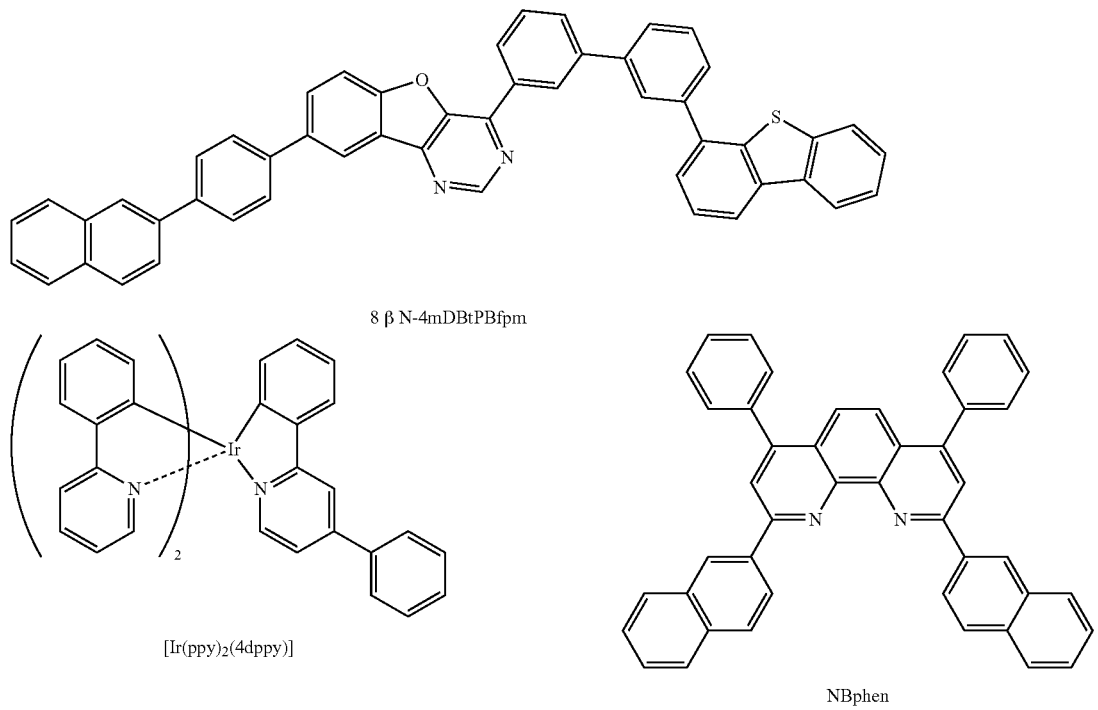

8 β N-4mDBtPBfpm

[Ir(ppy)₂(4dppy)]

NBphen

<<Operation Characteristics of Light-Emitting Elements>>

Operation characteristics of the fabricated light-emitting elements 6 and 7 were measured. Note that the measurement was performed at room temperature. The results are shown in FIG. 33 to FIG. 36.

Table 6 shows initial values of main characteristics of the light-emitting elements 6 and 7 at around 1000 cd/m².

TABLE 6

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 6 | 3.6 | 0.046 | 1.2 | (0.44, 0.55) | 960 | 83 | 72 | 24 |
| Light-emitting element 7 | 3.6 | 0.055 | 1.4 | (0.45, 0.54) | 1100 | 82 | 71 | 24 |

The above results show that the light-emitting elements fabricated in this example have excellent element characteristics.

Figure 37:
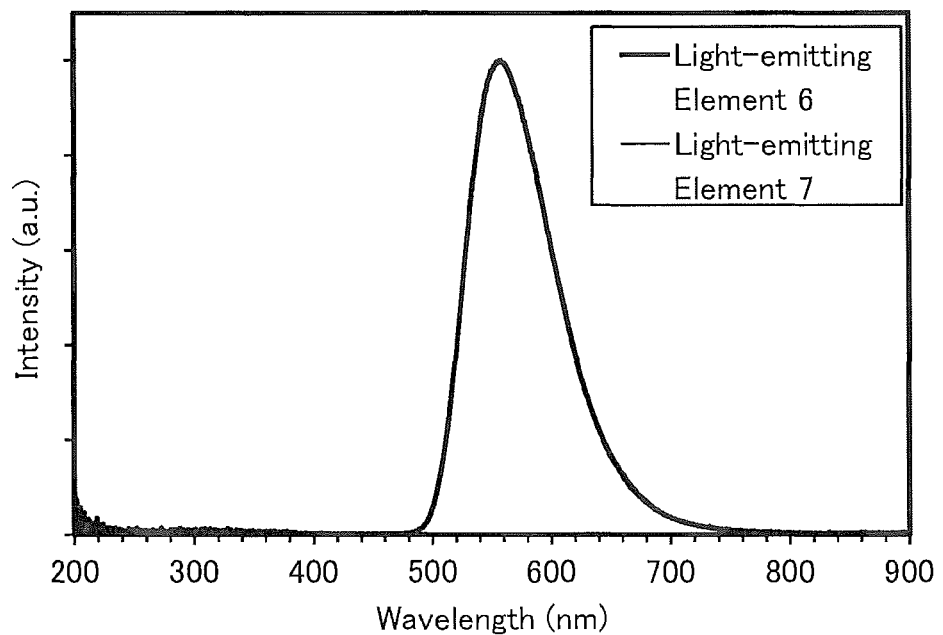
FIG. 37 shows emission spectra of the light-emitting element 6 and the light-emitting element 7.

FIG. 37 shows emission spectra when current at a current density of 2.5 mA/cm² was applied to the light-emitting elements. As shown in FIG. 37, the emission spectrum of each light-emitting element has a peak at around 558 nm, which is probably derived from light emission of [Ir(ppy)₂(4dppy)] contained in the light-emitting layer 913.

Figure 38:
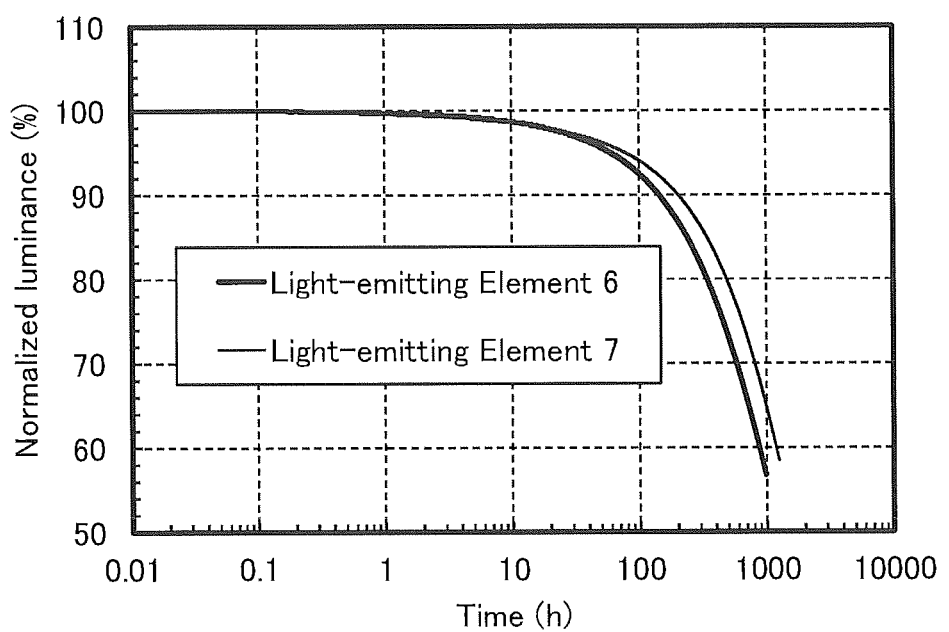
FIG. 38 shows the reliability of the light-emitting element 6 and the light-emitting element 7.
Figure 39:
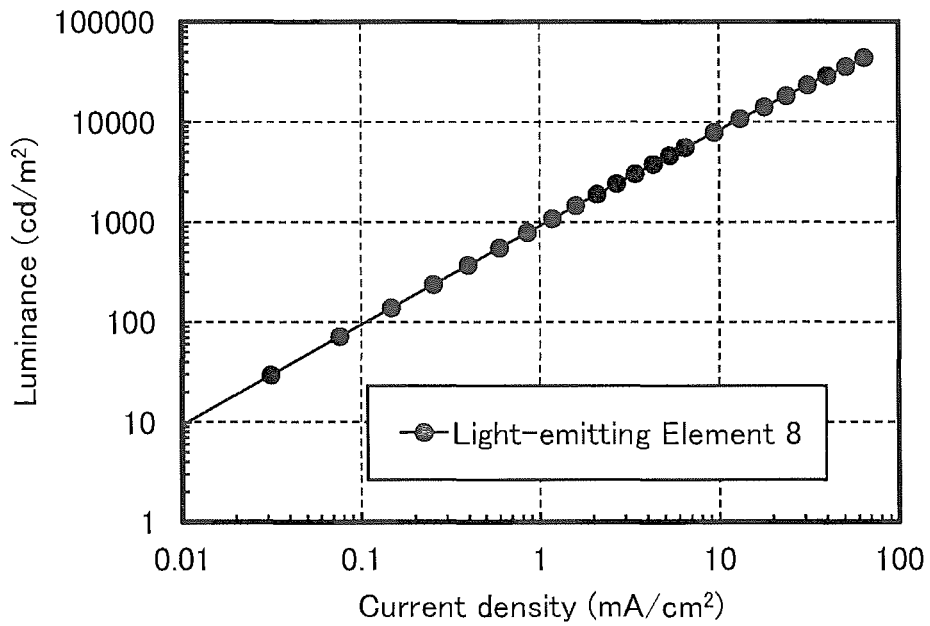
FIG. 39 shows current density-luminance characteristics of a light-emitting element 8.
Figure 40:
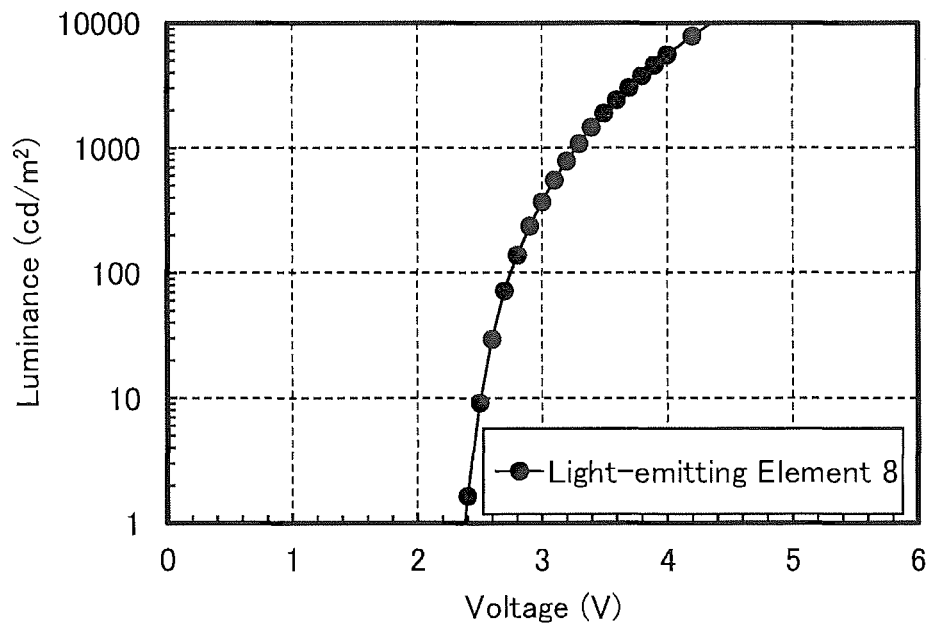
FIG. 40 shows voltage-luminance characteristics of the light-emitting element 8.
Figure 41:
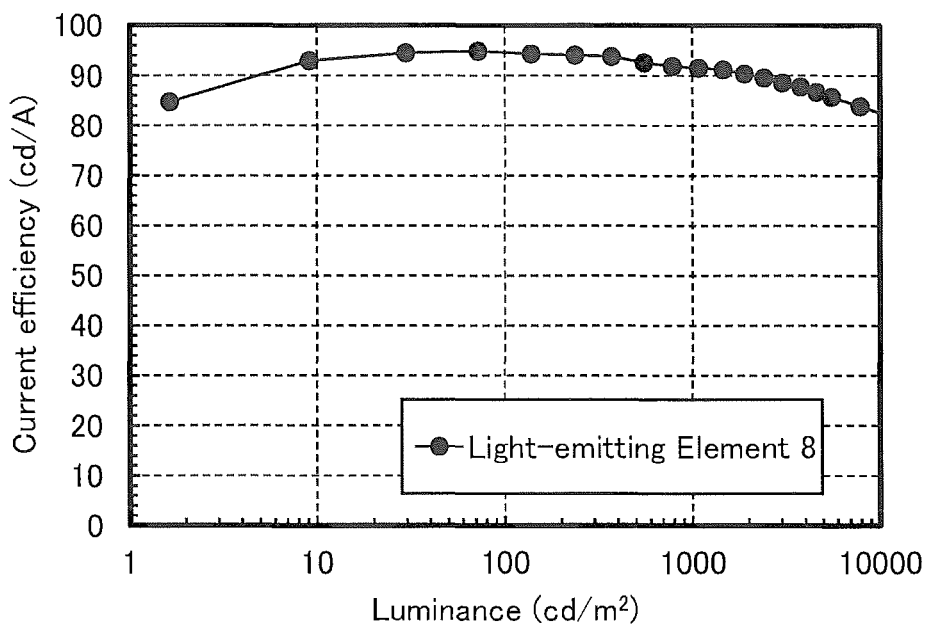
FIG. 41 shows luminance-current efficiency characteristics of the light-emitting element 8.
Figure 42:
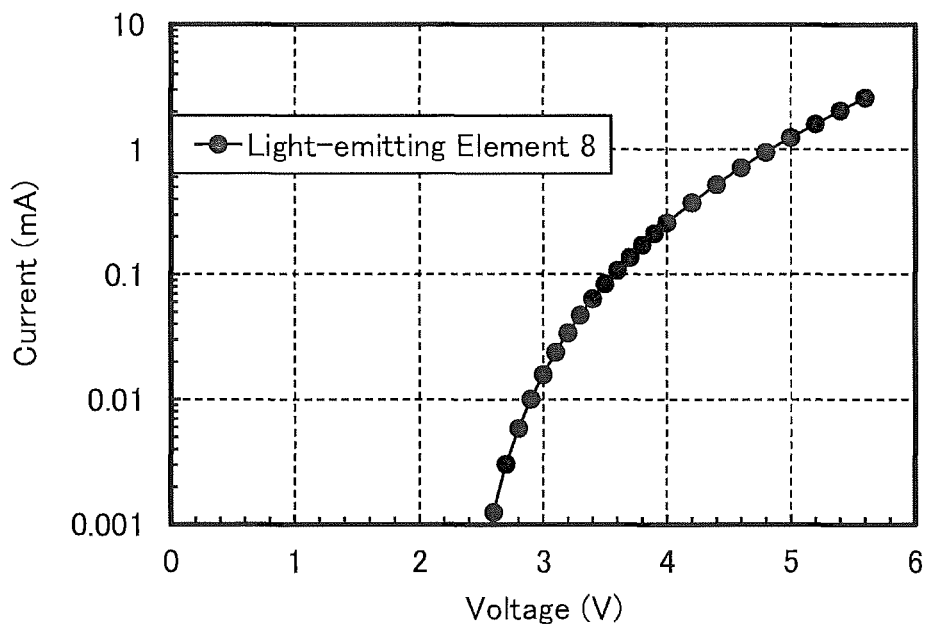
FIG. 42 shows voltage-current characteristics of the light-emitting element 8.

Next, reliability tests were performed on the light-emitting elements 6 and 7. FIG. 38 shows results of the reliability tests. In FIG. 38, the vertical axis represents normalized luminance (%) with an initial luminance of 100%, and the horizontal axis represents driving time (h) of the elements. Note that in the reliability tests, the light-emitting elements were driven at a constant current of 2 mA.

The reliability test results show that the light-emitting elements 6 and 7 of embodiments of the present invention have high reliability. This indicates that the use of 8α,N-4mDBtPBfpm (Structural Formula (103)) and 8βN-4mDBtBPBfpm (Structural Formula (116)), each of which is the organic compound of one embodiment of the present invention, is effective in increasing the lifetime of a light-emitting element. The results in this example also show that the condensed ring directly bonded to a benzene side of the benzofuropyrimidine skeleton or the benzothienopyrimidine skeleton directly contributes to increased lifetime of a light-emitting element.

Example 10

In this example, a light-emitting element 8 was fabricated as a light-emitting element of one embodiment of the present invention. The light-emitting element 8 uses for a light-emitting layer 8DBt-2mDBtPBfpm (Structural Formula (145)) described in Example 6. The measured results of characteristics of the light-emitting element 8 will be described below.

The element structure of the light-emitting element used in this example is similar to that described in Example 4 with reference to FIG. 18. Table 7 shows specific structures of layers in the element structure. Chemical formulae of materials used in this example are shown below.

TABLE 7

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 8 | ITSO (70 nm) | DBT3P-II:MoOx (2:1 45 nm) | PCBBi1BP (20 nm) | * | 8DBt-2mDBtPBfpm (20 nm) | NBPhen (10 nm) | LiF (1 nm) | Al (200 nm) |

* 8DBt-2mDBtPBfpm:PCCP:[Ir(ppy)₂(mdppy)] (0.7:0.3:0.1 40 nm)

[Chemical Formula 54]

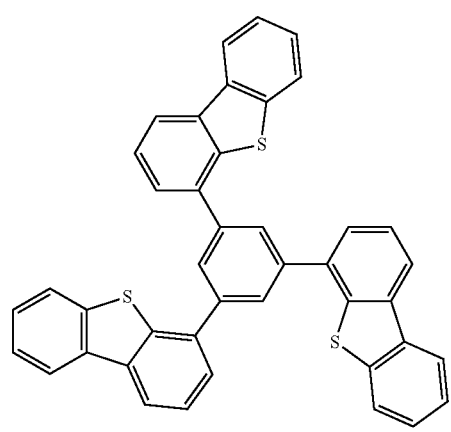

DBT3P-II

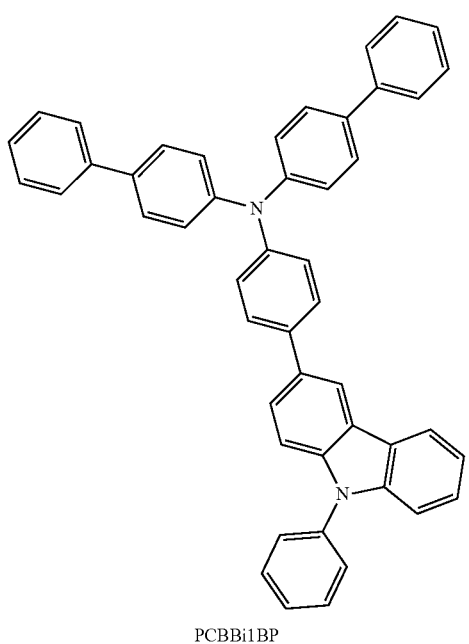

PCBBi1BP

-continued

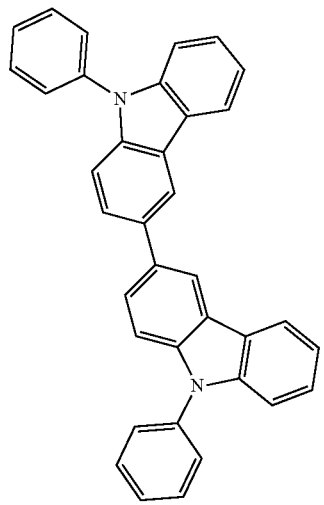

PCCP

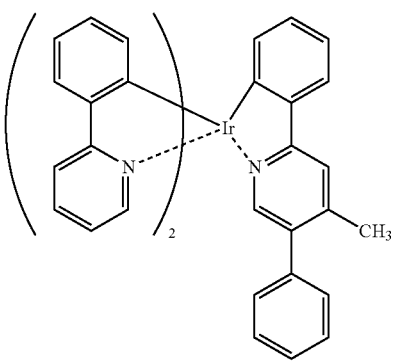

[Ir(ppy)₂(mdppy)]

(145)

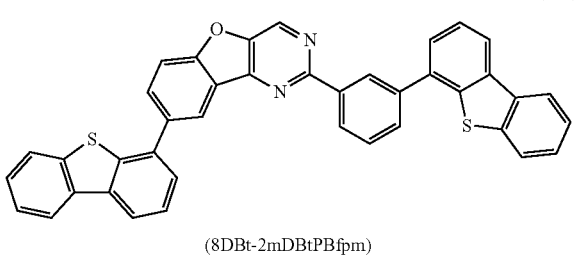

(8DBt-2mDBtPBfpm)

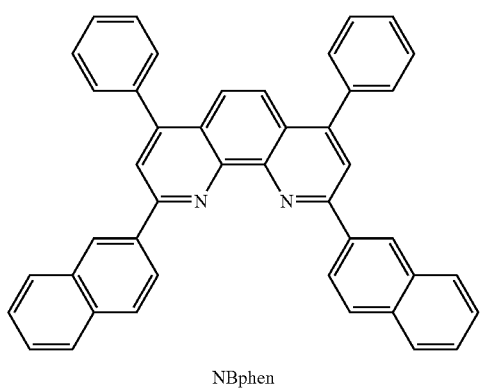

NBphen

<<Operation Characteristics of Light-Emitting Element>>

Operation characteristics of the fabricated light-emitting element 8 were measured. Note that the measurement was performed at room temperature. The results are shown in FIG. 39 to FIG. 42.

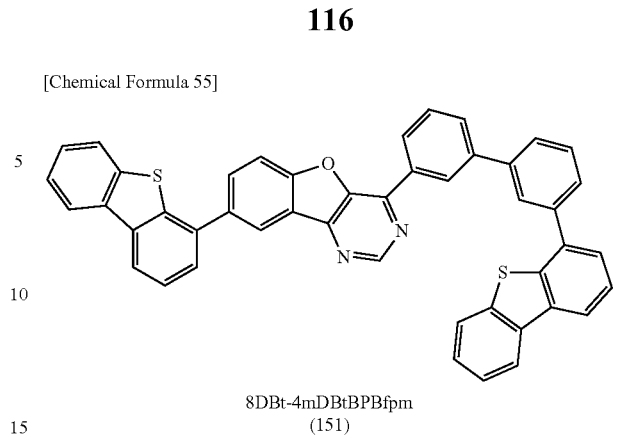

8DBt-4mDBtBPBfpm
(151)

Into a three-neck flask were put 7.00 g of 8-chloro-4-[3'-(dibenzothiophen-4-yl)biphenyl-3-yl]-[1]benzofuro[3,2-d]pyrimidine, 3.56 g of dibenzothiophene-4-boronic acid, 0.281 g of 2'-(dicyclohexylphosphino)acetophenone ethylene ketal, 6.00 g of cesium fluoride, and 65 mL of mesitylene. The mixture was degassed by being stirred with a reduced pressure. Then, the air in the flask was replaced with

TABLE 8

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 8 | 3.3 | 0.047 | 1.2 | (0.34, 0.63) | 1100 | 92 | 87 | 26 |

Table 8 shows initial values of main characteristics of the light-emitting element 8 at around 1000 cd/m$^2$.

The above results show that the light-emitting element 8 fabricated in this example has excellent element characteristics.

Figure 43:
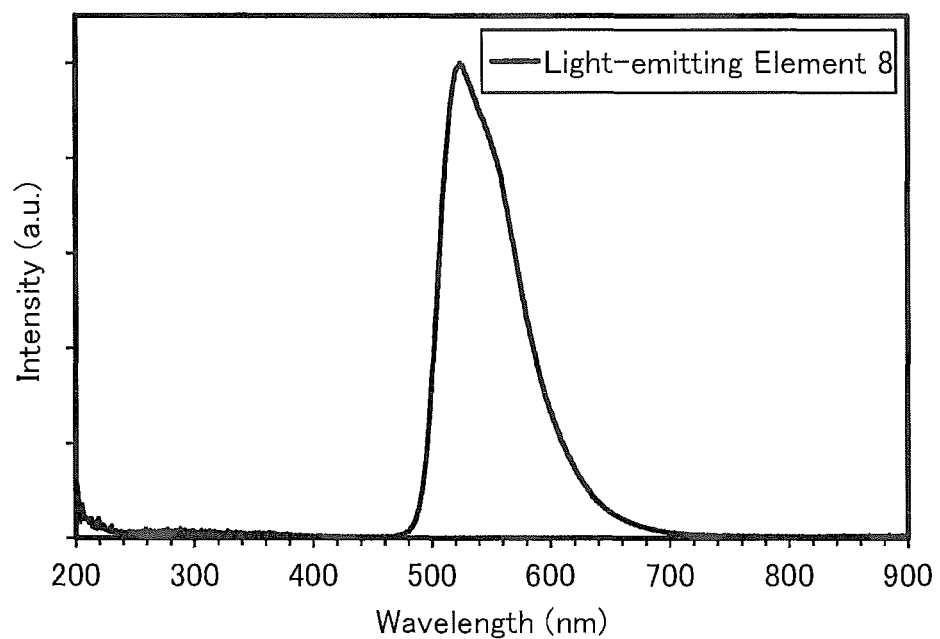
FIG. 43 shows an emission spectrum of the light-emitting element 8.

FIG. 43 shows emission spectra when current at a current density of 2.5 mA/cm$^2$ was applied to the light-emitting element 8. As shown in FIG. 43, the emission spectrum of the light-emitting element 8 has a peak at around 524 nm, which is probably derived from light emission of [Ir(ppy)$_2$(mdppy)] contained in the light-emitting layer 913.

Example 11

Synthesis Example 7

Described in this example is a method for synthesizing 8-(dibenzothiophen-4-yl)-4-[3'-(dibenzothiophen-4-yl)biphenyl-3-yl]-[1]benzofuro[3,2-d]pyrimidine (abbreviation: 8DBt-4mDBtBPBfpm), which is the organic compound of one embodiment of the present invention represented by Structural Formula (151). The structural formula of 8DBt-4mDBtBPBfpm is shown below.

nitrogen. To this mixture was added 0.359 g of tris(dibenzylideneacetone)dipalladium(0) (Pd$_2$(dba)$_3$), and the mixture was stirred at 120° C. for 1 hour. To this mixture was added 65 mL of degassed mesitylene and the mixture was stirred at 120° C. for 9.5 hours. Furthermore, 30 mL of degassed mesitylene was added to the mixture and stirred at 120° C. for 7 hours. To this mixture were added 0.360 g of Pd$_2$(dba)$_3$ and 0.284 g of 2'-(dicyclohexylphosphino)acetophenone ethylene ketal, and the mixture was stirred at 130° C. for 15 hours, and then at 140° C. for 6 hours. To this mixture were added 2.37 g of dibenzothiophene-4-boronic acid, 0.359 g of Pd$_2$(dba)$_3$, and 0.283 g of 2'-(dicyclohexylphosphino)acetophenone ethylene ketal, and the mixture was stirred at 140° C. for 40 hours. Water was added to the obtained reaction mixture and subjected to suction filtration. The obtained residue was washed with water and ethyl acetate, dissolved in heated toluene, and filtered through a filter aid filled with Celite, alumina, and Celite in this order. The obtained solution was concentrated and dried, and then recrystallized with toluene to give 5.56 g of a white solid, 8DBt-4mDBtBPBfpm (abbreviation), in a yield of 62%. By a train sublimation method, 1.95 g of the white solid was purified by sublimation. In the purification by sublimation, the solid was heated at 355° C. under a pressure of 2.8 Pa with an argon gas flow rate of 15 mL/min. After the purification by sublimation, 1.46 g of a target pale brown solid was obtained at a collection rate of 75%. Synthesis Scheme (g-1) is shown below.

[Chemical Formula 56]

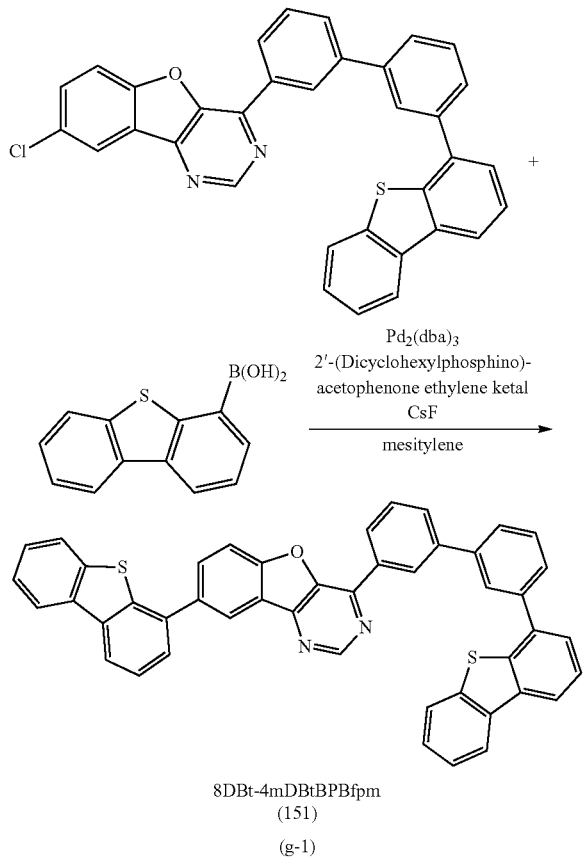

8DBt-4mDBtBPBfpm
(151)
(g-1)

Analysis results by nuclear magnetic resonance ($^1$H-NMR) spectroscopy of the pale brown solid obtained above are shown below. The results reveal that 8DBt-4mDBtBPBfpm was obtained.

$^1$H-NMR. δ (CDCl$_3$): 7.47-7.51 (m, 4H), 7.59-7.65 (m, 4H), 7.70 (t, 1H), 7.76-7.87 (m, 6H), 7.95 (d, 1H), 8.09 (d, 1H), 8.21-8.24 (m, 5H), 8.66-8.68 (m, 2H), 9.01 (s, 1H), 9.34 (s, 1H).

This application is based on Japanese Patent Application Serial No. 2017-122567 filed with Japan Patent Office on Jun. 22, 2017, the entire contents of which are hereby incorporated by reference.

REFERENCE NUMERALS

101: first electrode, 102: second electrode, 103: EL layer, 103a,103b, 103c: EL layer, 104: charge-generation layer, 111, 111a, 111b: hole-injection layer, 112, 112a, 112b: hole-transport layer, 113, 113a, 113b, 113c: light-emitting layer, 114, 114a, 114b: electron-transport layer, 115, 115a, 115b: electron-injection layer, 200R, 200G, 200B: optical path length, 201: first substrate, 202: transistor (FET), 203R, 203G, 203B, 203W: light-emitting element, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting element, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting element, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4015: diffusion plate, 4100: lighting device, 4200: lighting device, 4201: substrate, 4202: light-emitting element, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 4215: diffusion plate, 4300: lighting device, 5101: light, 5102: wheel cover, 5103: door, 5104: display portion, 5105: steering wheel, 5106: gear lever, 5107: seat, 5108: inner rearview mirror, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7012: support, 7013: earphone, 7014: antenna, 7015: shutter button, 7016: image receiving portion, 7018: stand, 7020: camera, 7019: microphone, 7021: external connection portion, 7022, 7023: operation button, 7024: connection terminal, 7025: band, 7026: clasp, 7027: icon indicating time, 7028: another icon, 8001: lighting device, 8002: lighting device, 8003: lighting device, 8004: lighting device, 9310: portable information terminal, 9311: display portion, 9312: display region, 9313: hinge, 9315: housing

The invention claimed is:

1. An organic compound represented by General Formula (G3):

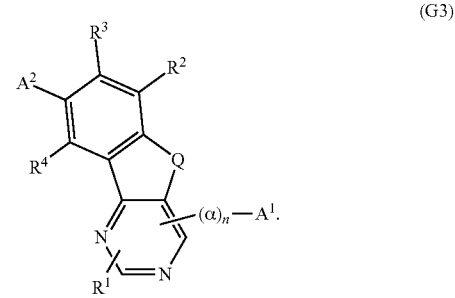

wherein:

Q represents oxygen or sulfur;

α represents a substituted or unsubstituted arylene group having 6 to 13 carbon atoms;

n represents an integer of 0 to 4;

A$^1$ represents a substituted or unsubstituted aryl group having 6 to 100 total carbon atoms or a substituted or unsubstituted heteroaryl group having 6 to 100 total carbon atoms;

R$^1$ represents hydrogen and R$^2$ to R$^4$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and A² is a condensed ring having any one of a substituted or unsubstituted triphenylene skeleton and a substituted or unsubstituted phenanthrene skeleton.

2. An organic compound represented by General Formula (G4):

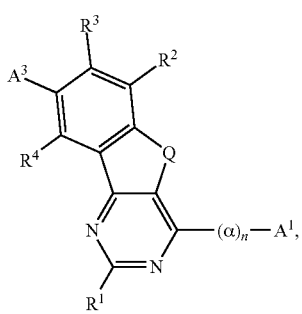

(G4)

wherein:
Q represents oxygen or sulfur;
α represents a substituted or unsubstituted arylene group having 6 to 13 carbon atoms;
n represents an integer of 0 to 4;
A¹ represents a substituted or unsubstituted aryl group having 6 to 100 total carbon atoms or a substituted or unsubstituted heteroaryl group having 6 to 100 total carbon atoms;
R¹ represents hydrogen and R² to R⁴ dependently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and
A³ is a condensed ring having any one of a substituted or unsubstituted triphenylene skeleton and a substituted or unsubstituted phenanthrene skeleton.

3. An organic compound represented by General Formula (G6):

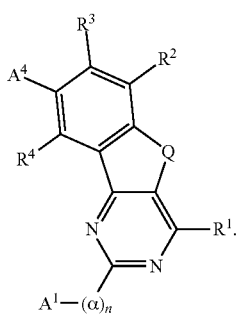

(G6)

wherein:
Q represents oxygen or sulfur; α represents a substituted or unsubstituted arylene group having 6 to 13 carbon atoms;
n represents an integer of 0 to 4;
A¹ represents a substituted or unsubstituted aryl group having 6 to 100 total carbon atoms or a substituted or unsubstituted heteroaryl group having 6 to 100 total carbon atoms;
R¹ represents hydrogen and R² to R⁴ dependently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms;
A⁴ is a condensed ring having any one of a substituted or unsubstituted triphenylene skeleton, and a substituted or unsubstituted phenanthrene skeleton; and
in the case where any of the substituted or unsubstituted aryl group having 6 to 13 carbon atoms has a substituent, the substituent includes any of an alkyl group having 1 to 7 carbon atoms, a cycloalkyl group having 5 to 7 carbon atoms and an aryl group having 6 to 12 carbon atoms.

4. The organic compound according to claim 1, wherein A¹ has any of a diarylamino group, a condensed aromatic hydrocarbon ring, and a π-electron rich condensed heteroaromatic ring.

5. The organic compound according to claim 1, wherein A¹ is a substituted or unsubstituted condensed aromatic hydrocarbon ring or a substituted or unsubstituted π-electron rich condensed heteroaromatic ring.

6. The organic compound according to claim 1, wherein A¹ is a substituted or unsubstituted condensed heteroaromatic ring having any one of a dibenzothiophene skeleton, a dibenzofuran skeleton, and a carbazole skeleton.

7. The organic compound according to claim 1, wherein A¹ is any one of General Formulae (A¹-1) to (A¹-17):

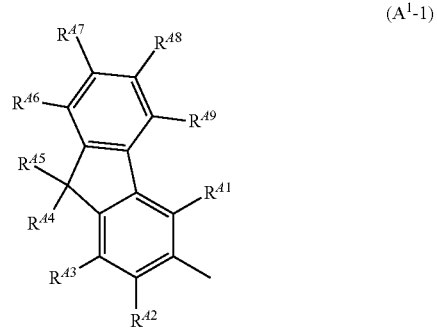

(A¹-1)

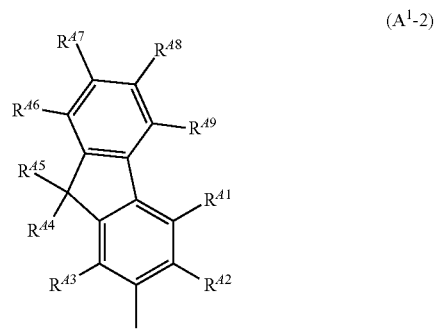

(A¹-2)

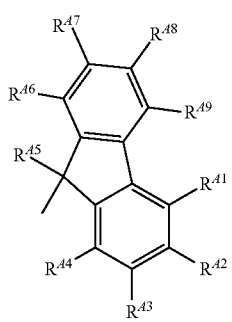
(A¹-3)
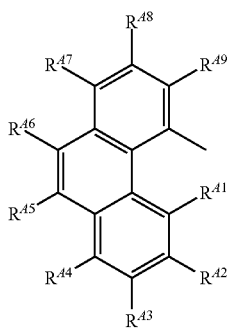
(A¹-4)
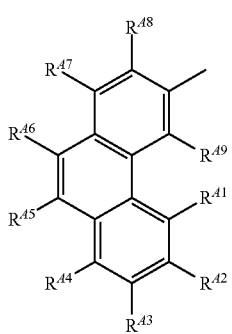
(A¹-5)
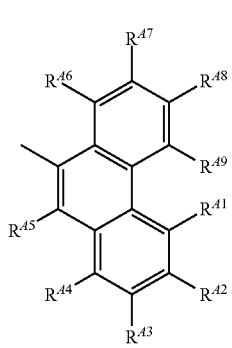
(A¹-6)
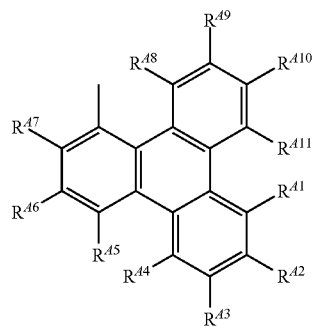
(A¹-7)
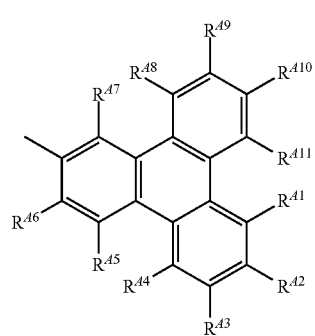
(A¹-8)
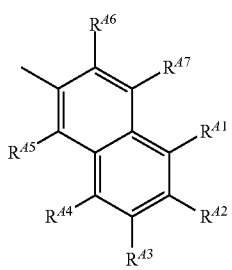
(A¹-9)
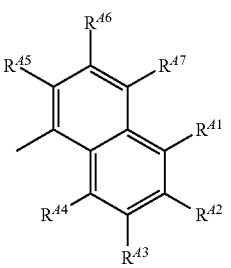
(A¹-10)
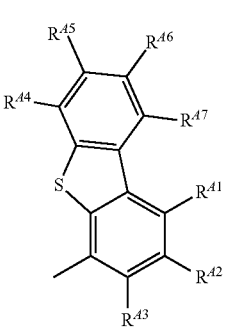
(A¹-11)

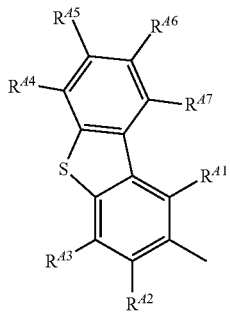 (A¹-12)

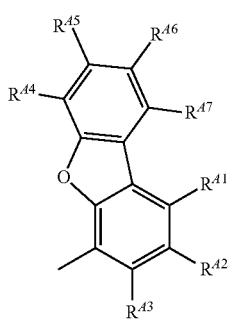 (A¹-13)

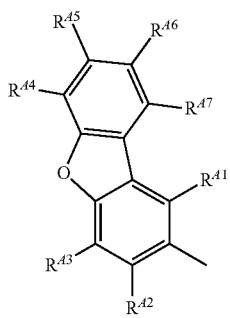 (A¹-14)

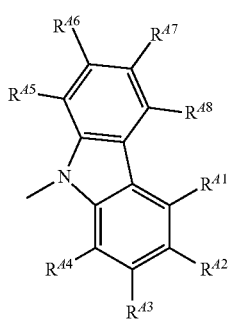 (A¹-15)

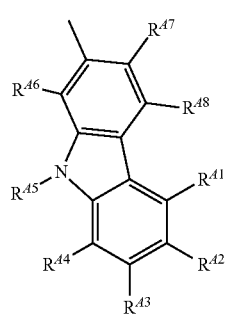 (A¹-16)

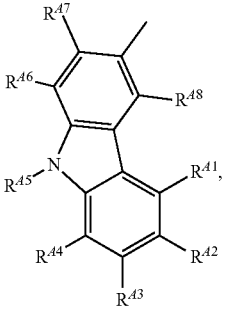 (A¹-17)

wherein $A^2$ is any one of General Formulae (A¹-4) to (A¹-8), and wherein $R^1$ to $R^{411}$ independently represent any one of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms.

8. The organic compound according to claim 1, wherein a is any one of General Formulae (Ar-1) to (Ar-18):

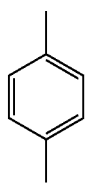 (Ar-1)

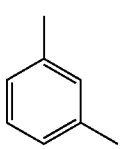 (Ar-2)

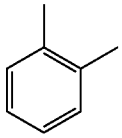 (Ar-3)

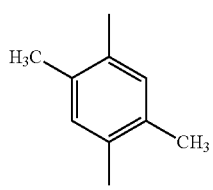 (Ar-4)

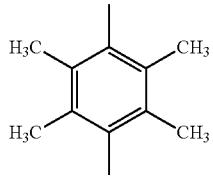 (Ar-5)

-continued
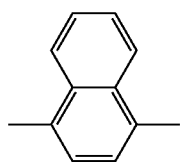 (Ar-6)
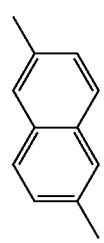 (Ar-7)
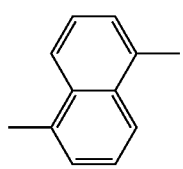 (Ar-8)
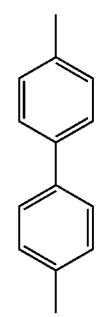 (Ar-9)
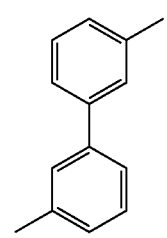 (Ar-10)
-continued
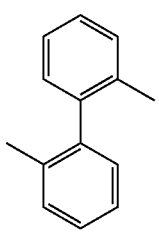 (Ar-11)
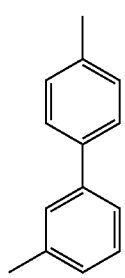 (Ar-12)
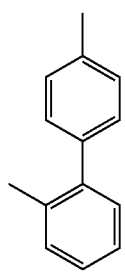 (Ar-13)
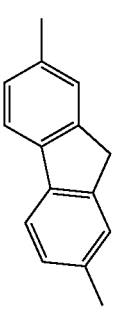 (Ar-14)
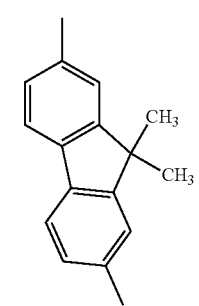 (Ar-15)

-continued (Ar-16)
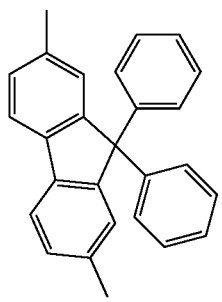

(Ar-17)
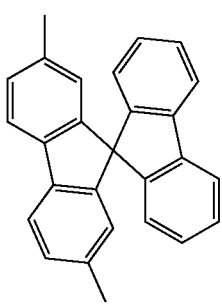

(Ar-18)
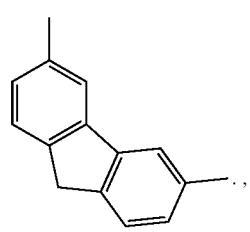

9. The organic compound according to claim 1, wherein the organic compound is represented by Structural Formula (100):

(100)
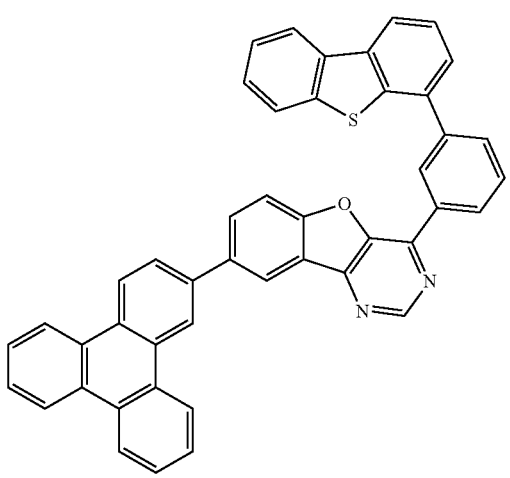

-continued (101)
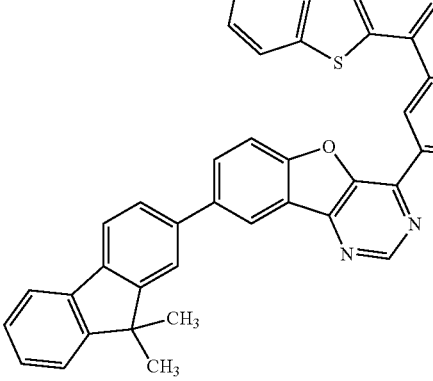

(102)
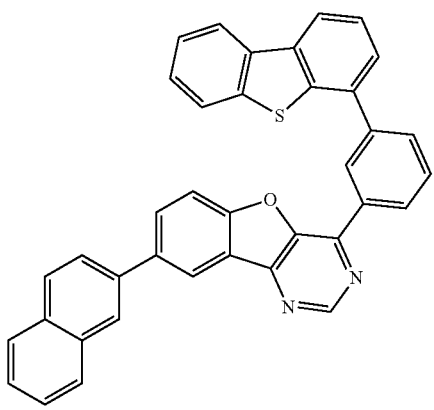

10. A light-emitting element comprising the organic compound according to claim 1.

11. A light-emitting element comprising an EL layer between a pair of electrodes,
wherein the EL layer comprises the organic compound according to claim 1.

12. A light-emitting element comprising an EL layer between a pair of electrodes,
wherein the EL layer comprises a light-emitting layer, and
wherein the light-emitting layer comprises the organic compound according to claim 1.

13. A light-emitting device comprising:
the light-emitting element according to claim 10; and
at least one of a transistor and a substrate.

14. An electronic device comprising:
the light-emitting device according to claim 13; and
at least one of a microphone, a camera, an operation button, an external connection portion, and a speaker.

15. A lighting device comprising:
the light-emitting element according to claim 10; and
at least one of a housing, a cover, and a support.

* * * * *